United States Patent
Ruhl et al.

(10) Patent No.: US 10,209,212 B2
(45) Date of Patent: Feb. 19, 2019

(54) SENSOR ARRANGEMENT FOR PARTICLE ANALYSIS AND A METHOD FOR PARTICLE ANALYSIS

(71) Applicant: Infineon Technologies AG, Neubiberg (DE)

(72) Inventors: Guenther Ruhl, Regensburg (DE); Thomas Hirsch, Regensburg (DE); Gerhard Poeppel, Duggendorf (DE); Herbert Roedig, Riemerling (DE)

(73) Assignee: Infineon Technologies AG, Neubiberg (DE)

( * ) Notice: Subject to any disclaimer, the term of this patent is extended or adjusted under 35 U.S.C. 154(b) by 395 days.

(21) Appl. No.: 15/043,701

(22) Filed: Feb. 15, 2016

(65) Prior Publication Data
US 2017/0234822 A1    Aug. 17, 2017

(51) Int. Cl.
*G01R 17/00* (2006.01)
*G01N 27/22* (2006.01)
*G01N 15/10* (2006.01)

(52) U.S. Cl.
CPC ........... *G01N 27/221* (2013.01); *G01N 15/10* (2013.01); *G01N 2015/1087* (2013.01); *G01N 2015/1093* (2013.01); *G01N 2027/222* (2013.01)

(58) Field of Classification Search
CPC .... G01R 27/2605; G01R 17/02; G01R 17/00; G01R 31/2856; G01R 15/00; G01R 15/002; G01R 19/0061; G01R 19/0084
USPC ....... 324/347, 358, 359, 370, 444–450, 515, 324/559, 660–661, 688, 679
See application file for complete search history.

(56) References Cited

U.S. PATENT DOCUMENTS

| | | | | |
|---|---|---|---|---|
| 4,157,498 A | * | 6/1979 | Johnson | G01N 15/1218 324/71.1 |
| 8,342,044 B2 | * | 1/2013 | Zhao | G01N 15/1404 73/864.21 |
| 8,941,390 B2 | * | 1/2015 | Seymour | G01R 1/06783 257/88 |
| 9,101,309 B1 | * | 8/2015 | Liu | A61B 5/1486 |
| 2009/0198117 A1 | * | 8/2009 | Cooper | A61B 5/14532 600/347 |
| 2012/0057161 A1 | * | 3/2012 | Tkachuk | G01N 21/3504 356/437 |

(Continued)

*Primary Examiner* — Jermele M Hollington
*Assistant Examiner* — Taqi Nasir
(74) *Attorney, Agent, or Firm* — Viering, Jentschaura & Partner MBB

(57) ABSTRACT

According to various embodiments, a sensor arrangement for particle analysis may include: a base electrode configured to generate an electrical field for particle attraction; a support layer disposed over the base electrode; a sensor array disposed over the support layer and including or formed from a plurality of sensor elements, wherein each sensor element of the plurality of sensor elements is configured to generate or modify an electrical signal in response to a particle at least one of adsorbed to and approaching the sensor element; and an electrical contact structure may include or be formed from a plurality of contact lines, wherein each contact line of the plurality of contact lines is electrically connected to a respective sensor element of the plurality of sensor elements, such that each sensor element of the plurality of sensor elements is addressable via the contact structure.

22 Claims, 29 Drawing Sheets

(56) References Cited

U.S. PATENT DOCUMENTS

| | | | | |
|---|---|---|---|---|
| 2012/0282594 A1* | 11/2012 | Chen | ............... | G01N 27/4146 |
| | | | | 435/5 |
| 2015/0057161 A1* | 2/2015 | Schultze | ............ | C12N 5/0645 |
| | | | | 506/2 |
| 2015/0308972 A1* | 10/2015 | Akiyama | ........... | G01N 27/128 |
| | | | | 73/31.06 |
| 2015/0349240 A1* | 12/2015 | Mizukami | ......... | H01L 41/1876 |
| | | | | 347/70 |

\* cited by examiner

FIG. 9A
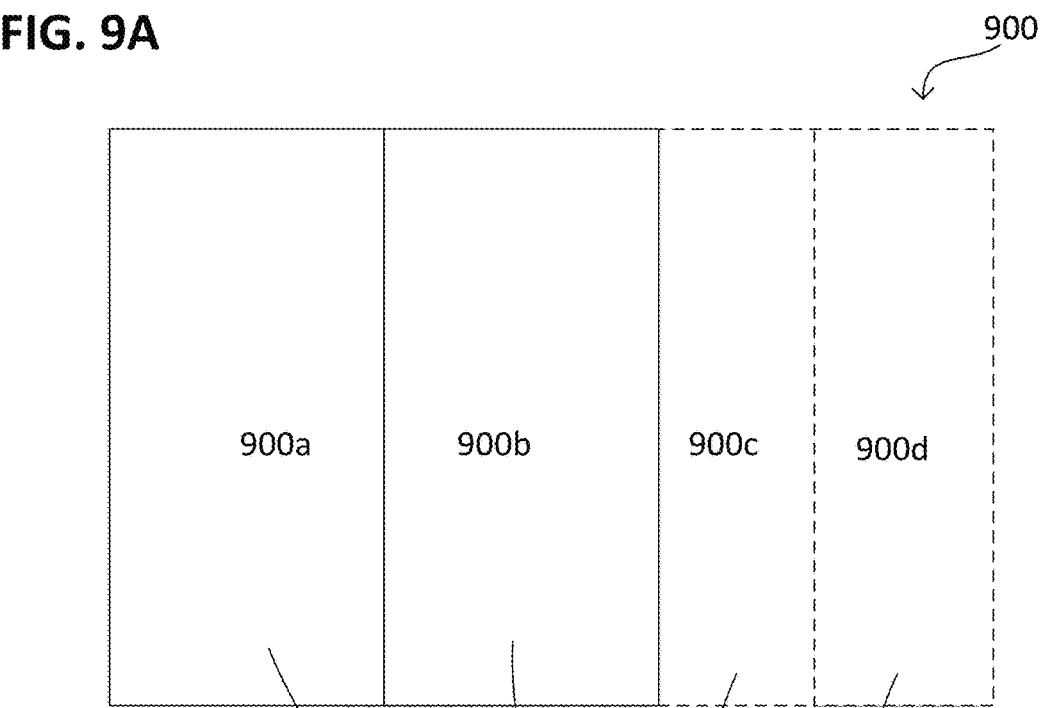
FIG. 9B
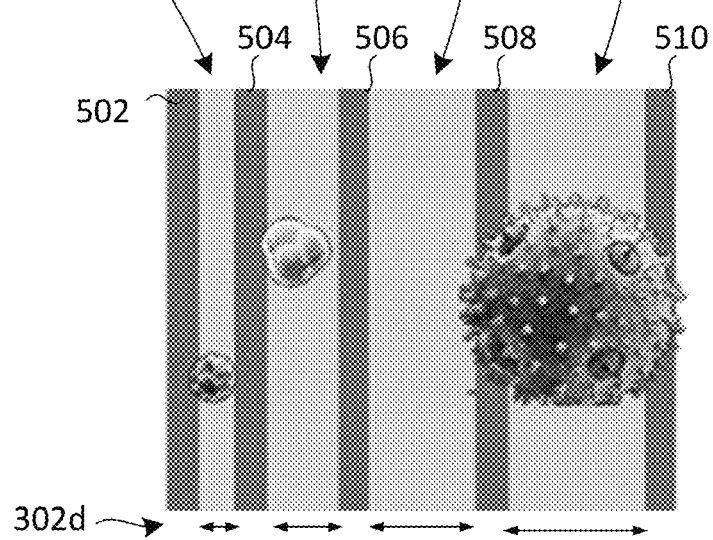
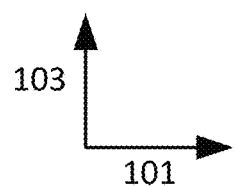

FIG. 23
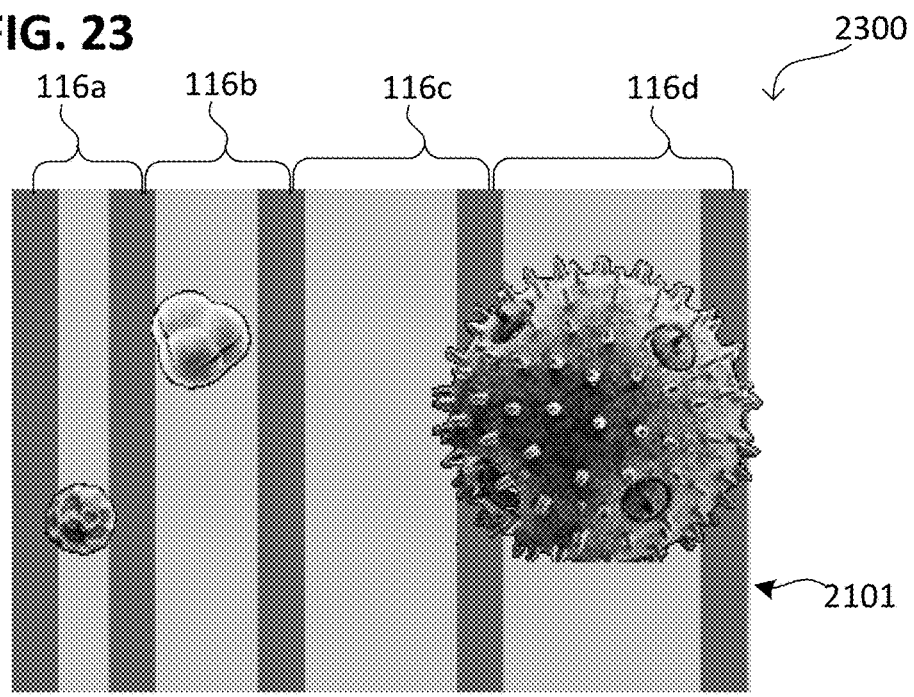
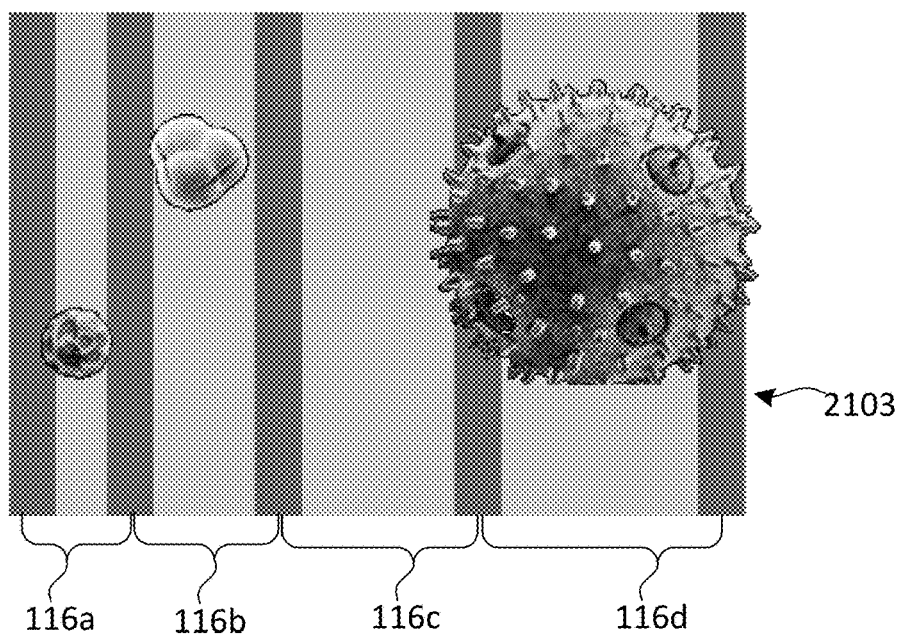

FIG. 24
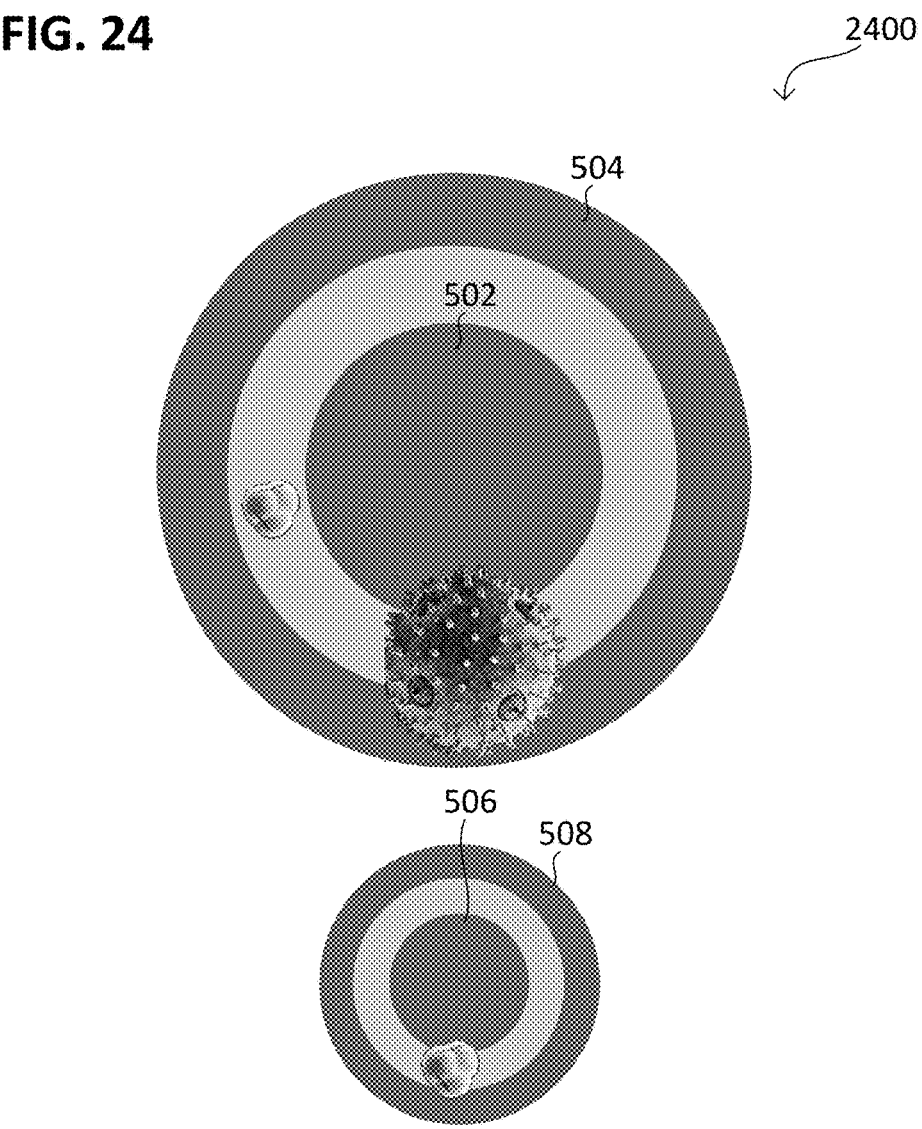
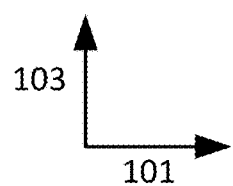

SENSOR ARRANGEMENT FOR PARTICLE ANALYSIS AND A METHOD FOR PARTICLE ANALYSIS

TECHNICAL FIELD

Various embodiments relate generally to a sensor arrangement for particle analysis and a method for particle analysis.

BACKGROUND

In general, particle sensors may be used to determine the presence and density of airborne particles. Conventional particle sensors are based on light scattering methods, which require a large form factor of the respective sensor device, e.g. in the range of several cubic centimeters. Due to the large size, conventional particle sensors may be limited in their mobile capability, for example, they may be limited in their suitability for the integration into mobile devices. Further, conventional particle sensors may be limited in their sensing capabilities, e.g. limited to a particle density analyzation. Illustratively, conventional particle sensors may fail in providing particle size information or particle sort information.

SUMMARY

According to various embodiments, a sensor arrangement for particle analysis may include: a base electrode configured to generate an electrical field for particle attraction; a support layer disposed over the base electrode; a sensor array disposed over the support layer and including or formed from a plurality of sensor elements, wherein each sensor element of the plurality of sensor elements is configured to generate or modify an electrical signal in response to a particle at least one of adsorbed to and approaching the sensor element; and an electrical contact structure including or formed from a plurality of contact lines, wherein each contact line of the plurality of contact lines is electrically connected to a respective sensor element of the plurality of sensor elements, such that each sensor element of the plurality of sensor elements is addressable via the contact structure.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 9A and FIG. 9B respectively show a sensor arrangement according to various embodiments;

FIG. 21 to FIG. 26 respectively show a sensor array according to various embodiments;

DESCRIPTION

Figure 1A:
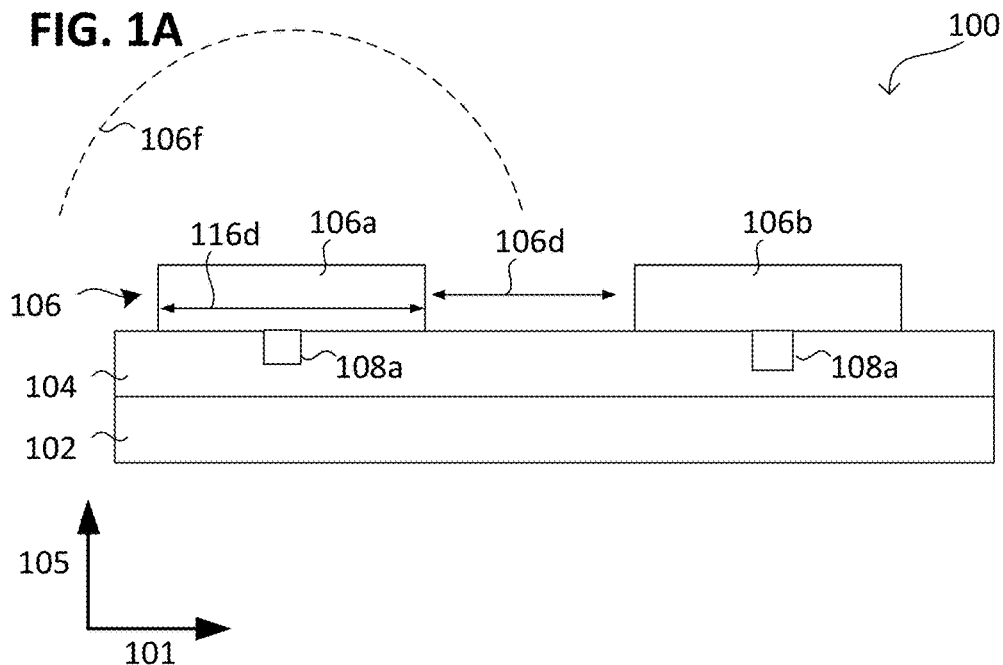
FIG. 1A and FIG. 1B respectively show a sensor arrangement according to various embodiments.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

The term "lateral" used with regards to the "lateral" extension of a structure (or of a substrate, a wafer, or a carrier) or "laterally" next to, may be used herein to mean an extension or a positional relationship along a surface of a substrate, a wafer, or a carrier. That means that a surface of a substrate (e.g. a surface of a carrier, or a surface of a wafer) may serve as reference, commonly referred to as the main processing surface of the substrate (or the main processing surface of the carrier or wafer). Further, the term "width" used with regards to a "width" of a structure (or of a structure element) may be used herein to mean the lateral extension of a structure. Further, the term "height" used with regards to a height of a structure (or of a structure element), may be used herein to mean an extension of a structure along a direction perpendicular to the surface of a substrate (e.g. perpendicular to the main processing surface of a substrate). The term "thickness" used with regards to a "thickness" of a layer may be used herein to mean the spatial extension of the layer perpendicular to the surface of the support (the material) on which the layer is deposited. If the surface of the support is parallel to the surface of the substrate (e.g. to the main processing surface) the "thickness" of the layer deposited on the support may be the same as the height of the layer. Further, a "vertical" structure may be referred to as a structure extending in a direction perpendicular to the lateral direction (e.g. perpendicular to the main processing surface of a substrate) and a "vertical" extension may be referred to as an extension along a direction perpendicular to the lateral direction (e.g. an extension perpendicular to the main processing surface of a substrate).

According to various embodiments, at least one of a substrate and a sensor element may include or be formed from a semiconductor material of various types, including a group IV semiconductor (e.g. silicon or germanium), a compound semiconductor, e.g. a group III-V compound semiconductor (e.g. gallium arsenide) or other types, including group III semiconductors, group V semiconductors or polymers, for example. In an embodiment, at least one of the substrate and the sensor element is made of silicon (doped or undoped), in an alternative embodiment, the substrate is a silicon on insulator (SOI) wafer. As an alternative, any other suitable semiconductor material can be used for at least one of the substrate and the sensor element, for example a semiconductor compound material such as gallium phosphide (GaP), indium phosphide (InP), but also any suitable ternary semiconductor compound material or quaternary semiconductor compound material such as indium gallium arsenide (InGaAs). According to various embodiments, a sensor element may be formed at least one of in and on the substrate.

According to various embodiments, a metallic material may include or be formed from at least one chemical element of the following group of chemical elements (also referred to as metals): tungsten (W), aluminum (Al), copper (Cu), nickel (Ni), magnesium (Mg), chromium (Cr), iron (Fe), zinc (Zn), tin (Sn), gold (Au), silver (Ag), iridium (Ir), platinum (Pt), indium (In), cadmium (Cd), bismuth (Bi), vanadium (V), titanium (Ti), palladium (Pd), or zirconium (Zr) or a metal alloy including at least one chemical element of the group of chemical elements. By way of example, a metal alloy may include or be formed from at least two metals (e.g. two or more than two metals, e.g. in the case of an intermetallic compound) or at least one metal (e.g. one or more than one metal) and at least one other chemical element (e.g. a non-metal or a half metal). By way of example, a metal alloy may include or may be formed from at least one metal and at least one non-metal (e.g. carbon (C) or nitrogen (N)), e.g. in the case of steel or a nitride. By way of example, a metal alloy may include or may be formed from more than one metal (e.g. two or more metals), e.g. various compositions of gold with aluminum, various compositions of copper with aluminum, various compositions of copper and zinc (e.g. "brass") or an various compositions of copper and tin (e.g. "bronze"), e.g. including various intermetallic compounds. According to various embodiments, a metallic material may be electrically conductive.

A semiconductor material, layer, region or the like may be understood as having moderate electrical conductivity, e.g. an electrical conductivity (measured at room temperature and constant electric field direction, e.g. constant electric field) in the range from about $10^{-6}$ Siemens per meter (S/m) to about $10^6$ S/m. An electrically conductive material (e.g. a metallic material), layer, region or the like may be understood as having high electrical conductivity, e.g. an electrical conductivity (measured at room temperature and constant electric field direction, e.g. constant electric field) greater than about $10^6$ S/m, e.g. greater than about $10^7$ S/m. An electrically insulating material, layer, region or the like may be understood as having a poor electrical conductivity, e.g. an electrical conductivity (measured at room temperature and constant electric field direction, e.g. constant electric field) less than about $10^{-6}$ S/m, e.g. less than about $10^{-10}$ S/m.

According to various embodiments, a method and device may be provided for the detection, sort analysis and size analysis of airborne particles. The detection, sort analysis and size analysis may be based on measuring interactions of the adsorbed particles on a chip with a structured detector area (also referred to as sensor array), e.g. by at least one of impedance changes, reduced gas adsorption and optical shading. The adsorption of the particles on the chip is generated by electrostatic force. The desorption can either be provided at least one of electrostatic force and another force (e.g. by mechanical force). Particle sensors are integral part of air quality analysis (particulate matter and allergens, e.g. pollen). Integrating particle sensors into mobile devices may enable a finer mesh of environmental air quality monitoring.

According to various embodiments, a method and device may be provided for the detection of particles adsorbed on an electrically active area (e.g. forming a plurality of sensor elements). The electrically active area may include or be formed from lines or other lateral structures and spaces of varying shapes and dimensions in the range of the particles to be detected. The presence of adsorbed particles may be detected by various measurements with optional simultaneous comparison to a non-exposed (non-particle exposed) reference device. The various measurements may include at least one of:

measuring a change of impedance (capacity and/or conductivity) between electrodes;

measuring a reduction of ambient gas adsorption (e.g. $CO_2$);

measuring a shading of light by a detector array (e.g. photodiodes or solar cells);

measuring the non-exposed reference device, which allows the consideration (e.g. correction) of ambient influences, like air humidity or provides a baseline (also referred to as reference signal) for the fluid (e.g. gas) or light shading measurement.

According to various embodiments, the adsorption of the particles may be induced via an electrostatic field (also referred to as attraction field). If necessary, a fluid (e.g. a gas or gas mixture, e.g. air) to be analyzed may be pumped through the measurement device (also referred to as sensor arrangement) by a micro-pump, e.g. a microfluidic pump.

According to various embodiments, desorption of particles from the sensor array may be induced by at least one of: an electrostatic field (also referred to as repulsion field) and an additional repulsion mechanisms. For particles (smaller than about 1 μm) van-der-Waals forces may be stronger than electrostatic forces, so the additional repulsion mechanisms may be used to support the desorption of the particles. The additional repulsion mechanisms may include at least one of an acoustical release, a mechanical release, a photochemical release, and a Lotus effect based release. For example, the van-der-Waals forces may be reduced by a surface functionalization (also referred to as anti-adhesion layer). The anti-adhesion layer may include or be formed from a coating with self-assembled monolayers, e.g. alkanethiols with specific head groups, or other 2D-materials. This functionalization may be optionally used to form or control specific chemical bonds to the particles. The specific bonds may enable to detect the particle type (also referred to as particle sort), e.g. by detecting a strength or sort of the interaction (based on the specific bonds). In other words, the anti-adhesion layer optionally may include or be formed from a bonding-control functionalization.

According to various embodiments, subsequent data processing may allow the analysis of the particle size distribution and for example, the discrimination of pollen allergens from dust.

Figure 1B:
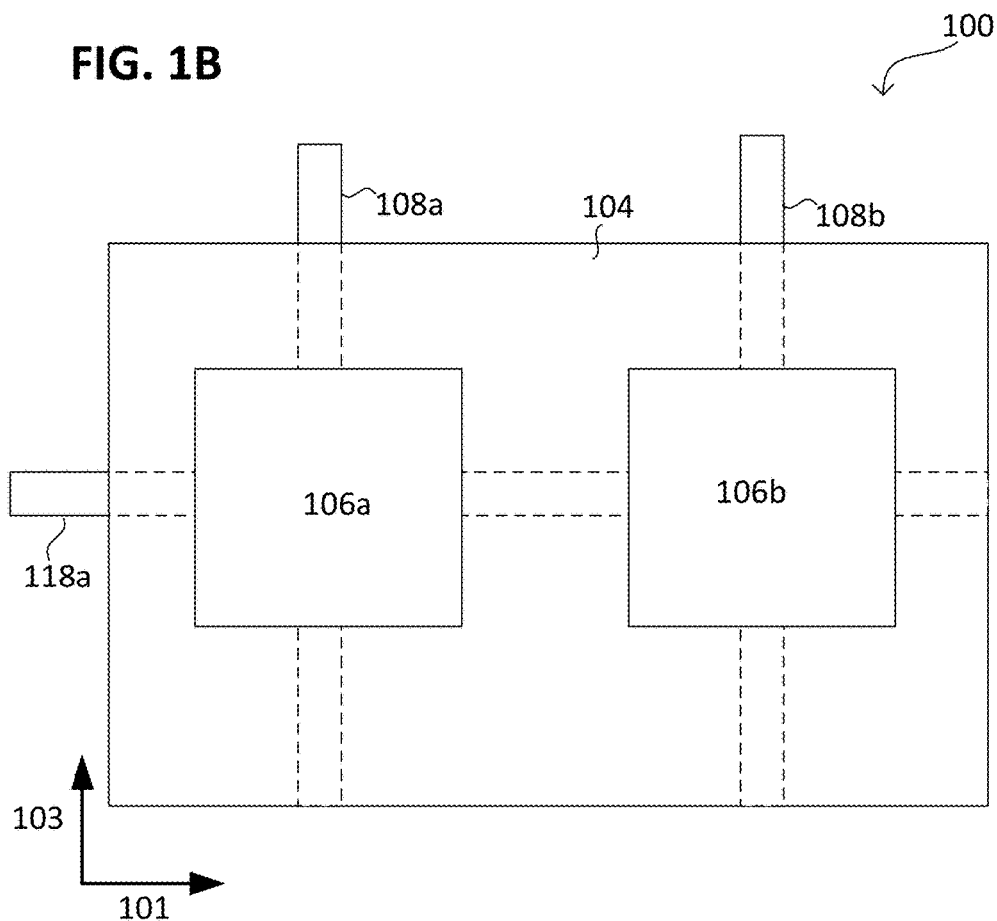

FIG. 1A illustrates a sensor arrangement 100 for particle analysis in a schematic side view or first cross sectional view (e.g. parallel to direction 103) and FIG. 1B the sensor arrangement 100 in a schematic top view or second cross sectional view perpendicular to the first cross sectional view (e.g. parallel to direction 105).

According to various embodiments, the sensor arrangement 100 (also referred to as detector arrangement 100) may include a base electrode 102. The base electrode 102 may be configured to generate an electrical field for particle attraction. The sensor arrangement 100 may further include a support layer 104. The support layer 104 may be disposed over the base electrode 102. An electrical conductivity of the support layer 104 may be less than an electrical conductivity of the base electrode 102. For example, the support layer 104 may include or be formed from an electrical insulating material, e.g. a polymer, ceramic or an oxide. Alternatively or additionally, the base electrode 102 may include or be formed from an electrical conductive material, e.g. a metallic material, e.g. including copper.

The base electrode 102 and the support layer 104 may be part of a substrate 102, 104. For example, the base electrode 102 may be buried in the substrate 102, 104. The base electrode 102 and the support layer 104 may be extended along a sensor plane 101, 103 defined by direction 101 and direction 103.

The sensor arrangement 100 may further include a sensor array 106 (also referred to as detector array 106) disposed over the support layer 104. The sensor array 106 may include or be formed from a plurality of sensor elements 106a, 106b (also referred to as detector elements). Each sensor element of the plurality of sensor elements 106a, 106b may be configured to generate or modify an electrical signal in response to a particle at least one of approaching and adsorbed to the sensor element 106a, 106b. The sensor elements of the plurality of sensor elements 106a, 106b may be disposed distant from each other, e.g. by a distance 106d. The distance 106d of two sensor elements of the plurality of sensor elements 106a, 106b may be less than about 100 micrometer (μm), e.g. less than about 50 μm, e.g. less than about 10 μm, e.g. less than 1 μm.

According to various embodiments, a lateral extension 116d of each sensor element of the plurality of sensor elements 106a, 106b may be less than about 100 μm, e.g. less than about 50 μm, e.g. less than about 10 μm, e.g. less than about 1 μm. The lateral extension 116d of a sensor element of the plurality of sensor elements 106a, 106b may define a sensing area the sensor element (along the sensor plane 103, 105, e.g. parallel thereto). According to various embodiments, the lateral distance 106d of two sensor elements of the plurality of sensor elements 106a, 106b may be less than 100 micrometer (μm), e.g. less than 50 micrometer, e.g. less than 10 micrometer, e.g. less than 1 micrometer.

Each sensor element of the plurality of sensor elements 106a, 106b may be configured to sense a particle entering a near field 106f of the sensor element (also referred to as approaching the sensor element). The near field 106 may have a maximum extension ranging away from the sensor elements 106a, 106b less than (e.g. about 75% of, e.g. about 50% of, e.g. about 25% of) the distance 106d. Alternatively or additionally, the near field 106 may have a maximum extension ranging away from the sensor elements 106a, 106b less than (e.g. about 75% of, e.g. about 50% of, e.g. about 25% of) the lateral extension 116d of the sensor elements 106a, 106b.

The sensor arrangement 100 may further include an electrical contact structure 108. The electrical contact structure 108 may include or be formed from a plurality of contact lines 108a, 108b, 118a. Each contact line of the plurality of contact lines 108a, 108b, 118a may be electrically connected to one sensor element of the plurality of sensor elements 106a, 106b. For example, each sensor element of the plurality of sensor elements 106a, 106b may be connected to at least two lines of the contact structure 108, e.g. one of a first plurality of contact lines 108a, 108b and a second contact line 118a. This may enable to address each sensor element of the plurality of sensor elements 106a, 106b via the contact structure 108.

Figure 15A:
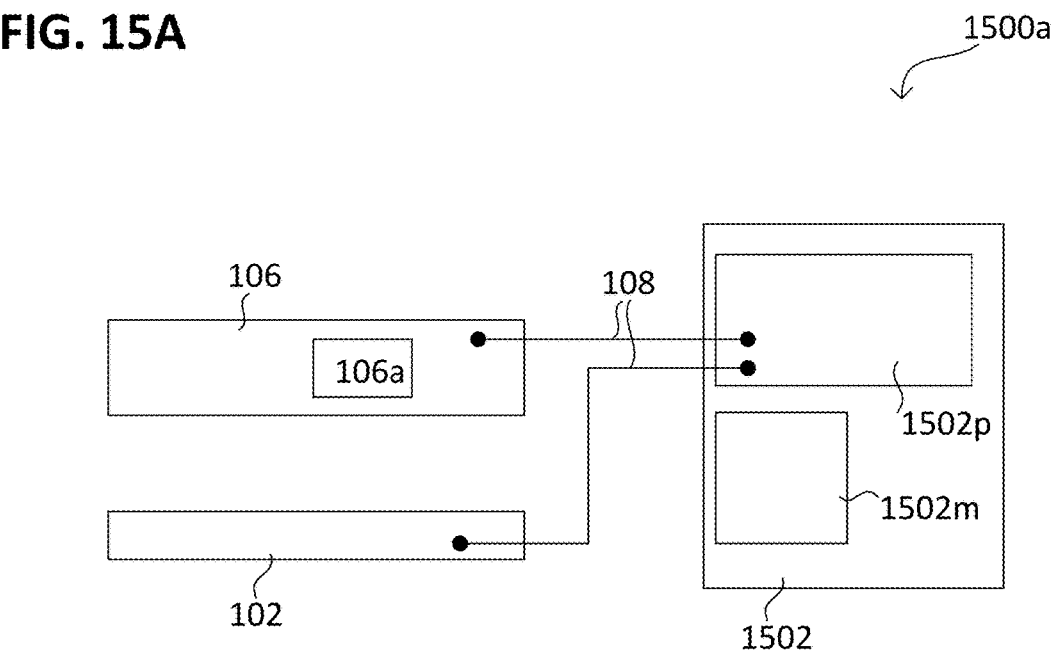
FIG. 15A shows a sensor arrangement according to various embodiments.
Figure 15B:
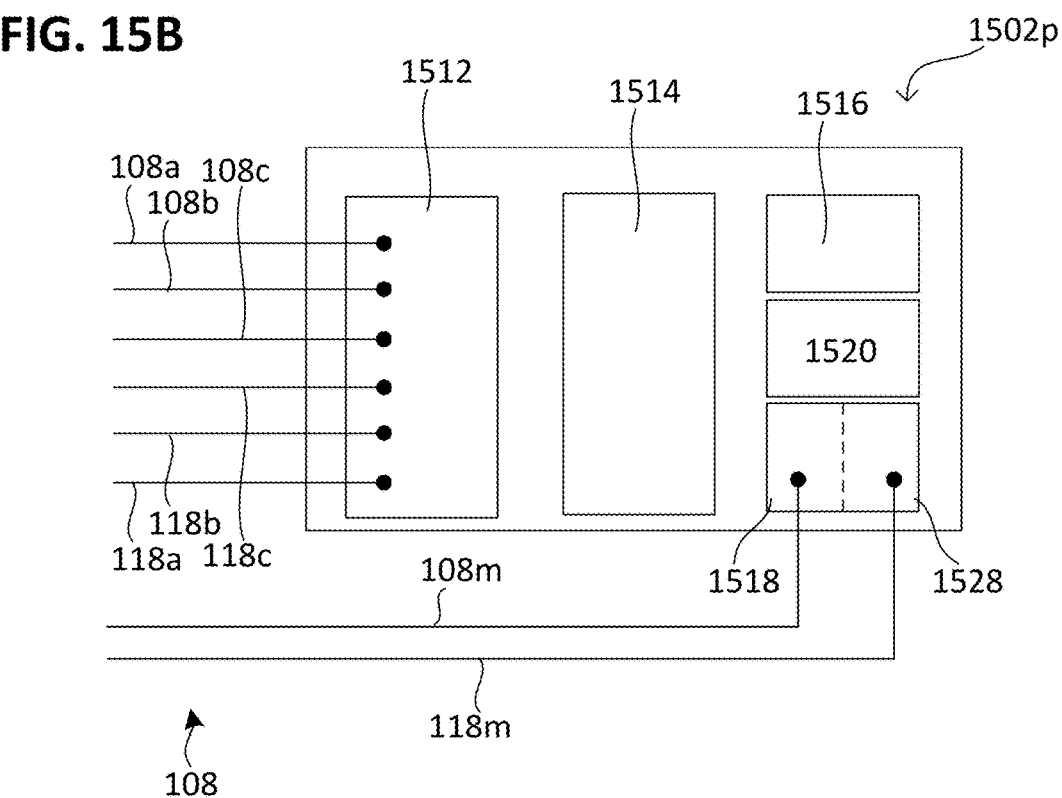
FIG. 15B shows a processing circuit according to various embodiments.

The base electrode 102 may be electrically coupled to a processing circuit (see for example, FIG. 15B). The processing circuit may be configured to provide at least one electrical potential to the base electrode 102, e.g. in accordance to one or more operation modes. The base electrode 102 may be configured to generate an electrostatic field in accordance to the respective electrical potential provided to the base electrode 102.

For example, a first electrical potential (also referred to as attraction potential) of the at least one electrical potential may be configured to attract the particles to the sensor array, e.g. by electrostatic attraction. Alternatively or additionally, a second electrical potential (also referred to as repulsion potential) of the at least one electrical potential may be configured to repulse the particles from the sensor array, e.g. by electrostatic repulsion. The electrical potentials of the at least one electrical potential may differ from each other, e.g. in at least one of: its magnitude and its polarity. The first electrical potential and the second electrical potential may differ in at least its polarity (e.g. with respect to an electrical reference potential, e.g. electrical mass).

For example, the processing circuit may be configured to provide the first electrical potential in a sensing operation mode. Alternatively or additionally, the processing circuit may be configured to provide the second electrical potential in a cleaning operation mode. The repulsion potential may be greater than a releasing potential which defines the electrical potential, at which the particles are released from the sensor arrangement 100. Alternatively or additionally, the processing circuit may be configured to provide the second electrical potential in a sensing operation mode (e.g. configured to sense at least one desorption event).

Figure 2A:
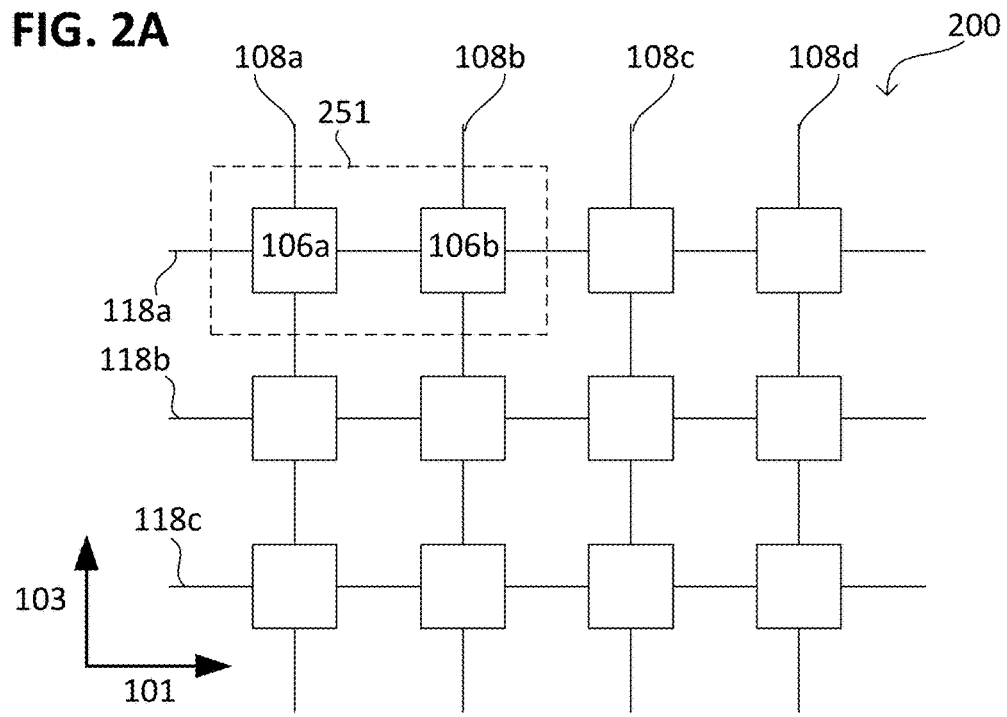
FIG. 2A and FIG. 2B respectively show a sensor arrangement according to various embodiments.
Figure 2B:
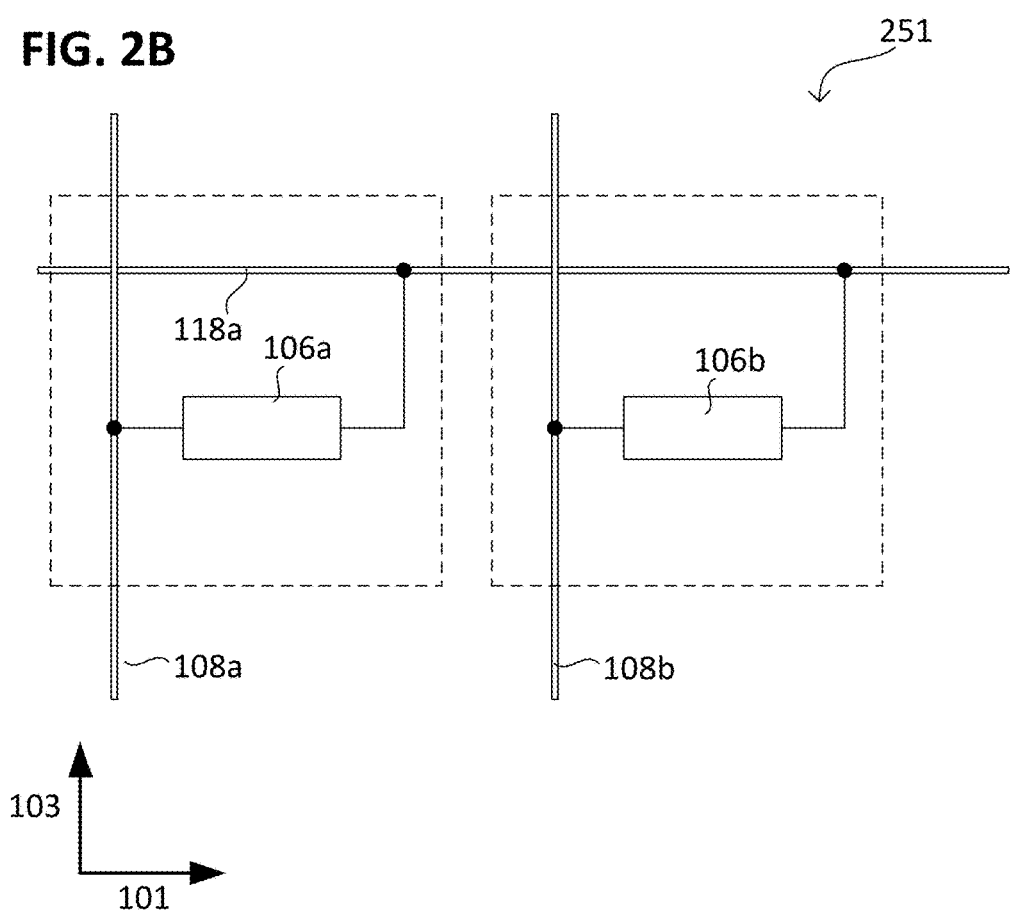

FIG. 2A illustrates a sensor arrangement 200 for particle analysis in a schematic top view or cross sectional view (e.g. parallel to direction 105) according to various embodiments and FIG. 2B the sensor arrangement 200 in a schematic circuit diagram of detailed view 251.

The electrical contact structure 108 may include a first plurality of contact lines 108a, 108b, 108c, 108d and a second plurality of contact lines 118a, 118b, 118c. The first plurality of contact lines 108a, 108b may be also referred to as plurality of word lines 108a, 108b, 108c, 108d. The second plurality of contact lines 118a, 118b, 118c may be also referred to as plurality of bit lines 118a, 118b, 118c.

Each sensor element of the plurality of sensor elements 106a, 106b may be coupled to one contact line of the first plurality of contact lines 108a, 108b and one contact line of the second plurality of contact lines 118a, 118b, 118c. In other words, each sensor element of the plurality of sensor elements 106a, 106b may couple one contact line of the first plurality of contact lines 108a, 108b and one contact line of the second plurality of contact lines 118a, 118b, 118c with each other. By sensing a contact line of the first plurality of contact lines 108a, 108b and a contact line of the second plurality of contact lines 118a, 118b, 118c exactly one sensor element of the plurality of sensor elements 106a, 106b may be read out. Illustratively, the a combination of one contact line of the first plurality of contact lines 108a, 108b and one contact line of the second plurality of contact lines 118a, 118b, 118c may be assigned to one sensor element of the plurality of sensor elements 106a, 106b (e.g. bijective).

Each sensor element of the plurality of sensor elements 106a, 106b may be configured to generate or modify an electrical signal transferred between one contact line of the first plurality of contact lines 108a, 108b and one contact line of the second plurality of contact lines 118a, 118b, 118c (in other words, the contact lines assigned thereto). For example, a first sensor element 106a of the plurality of sensor elements 106a, 106b may be assigned to a first contact line 108a of the first plurality of contact lines 108a, 108b and a first contact line 118a of the second plurality of contact lines 118a, 118b, 118c. For example, a second sensor element 106b of the plurality of sensor elements 106a, 106b may be assigned to a second contact line 108b of the first plurality of contact lines 108a, 108b and the first contact line 118a of the second plurality of contact lines 118a, 118b, 118c. By sensing the contact lines assigned to the respective sensor element of the plurality of sensor elements 106a, 106b, a signal may be sensed, which is generated or modified by the sensor element in response to a particle at least one of approaching and adsorbed to the sensor element.

Figure 3A:
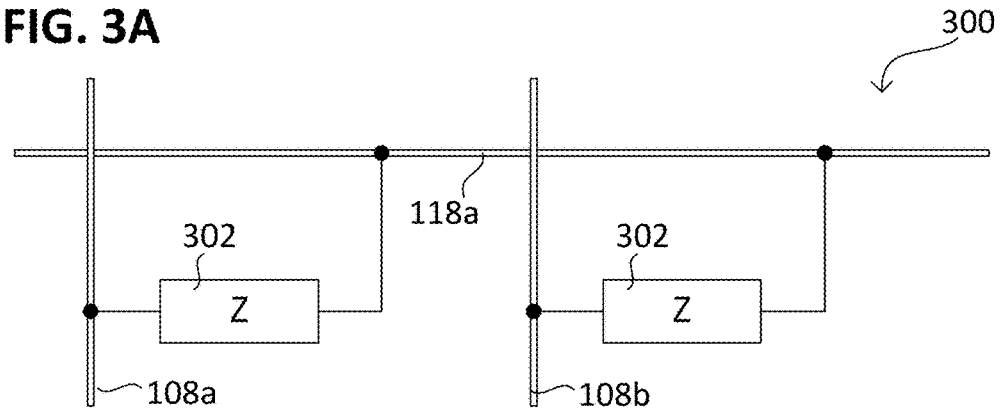
FIG. 3A to FIG. 3C respectively show a sensor arrangement according to various embodiments.
Figure 3B:
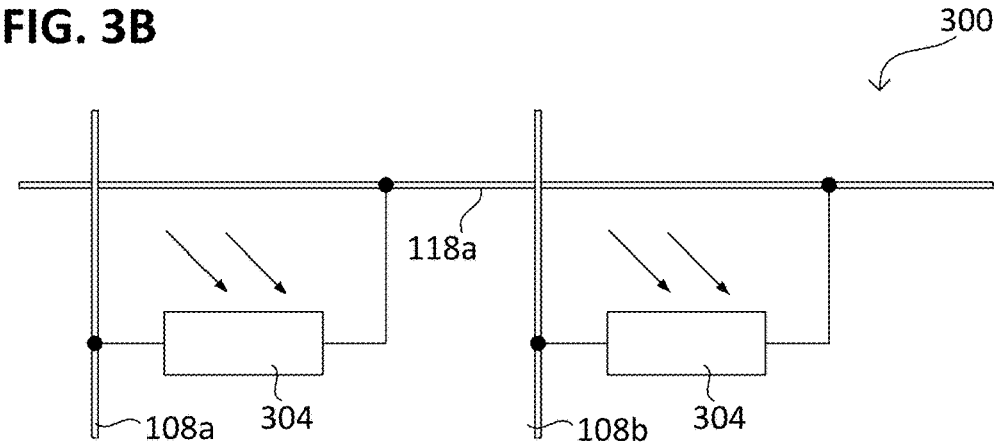
Figure 3C:
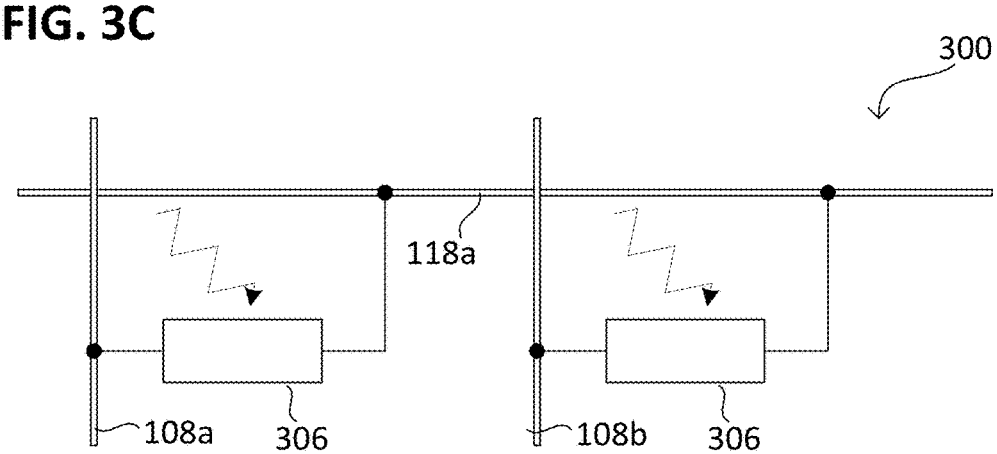

FIG. 3A, FIG. 3B and FIG. 3C respectively illustrate a sensor arrangement 300 for particle analysis in a schematic circuit diagram similar to detailed view 251 according to various embodiments.

According to various embodiments, the plurality of sensor elements 106a, 106b may include or be formed from sensor elements of at least one sensor type of the following sensor types: an electrical impedance sensor 302; a photoelectrical sensor 304; and an electrochemical fluid sensor 306. By way of example, the sensor array 106 may be a light detector array 106 including a plurality of photoelectrical sensor 304.

Figure 4A:
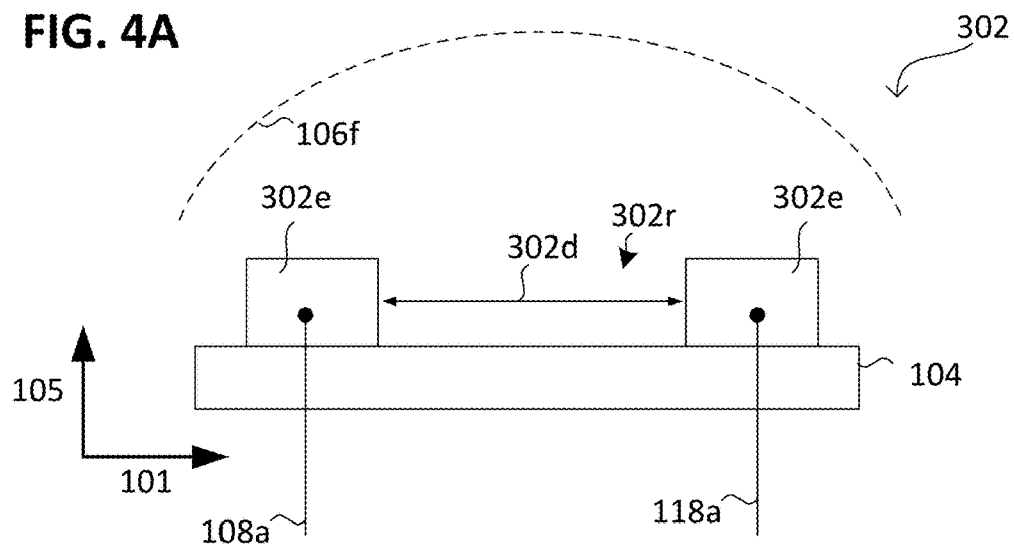
FIG. 4A to FIG. 4C shows sensor elements of various sensor types according to various embodiments.

FIG. 4A illustrates an electrical impedance sensor 302 for particle analysis in a schematic cross sectional view (e.g. parallel to direction 103).

The electrical impedance sensor 302 may include or be formed from two or more than two electrodes 302e (in other words, at least two electrodes 302e) separated from each other. The two or more than two electrodes 302e may be mounted on the support layer 104.

By way of example, at least a first electrode 302e of the two or more than two electrodes 302e may be electrically coupled to a first contact line 108a of the first plurality of contact lines 108a, 108b. Alternatively or additionally, at least a second electrode 302e of the two or more than two electrodes 302e may be electrically coupled to a first contact line 118a s of the second plurality of contact lines 118a, 118b, 118c.

The two or more than two electrodes 302e may define an electrical impedance of the electrical impedance sensor 302. The electrical impedance may include at least one of a resistive impedance (also referred to as electrical resistance) and a capacitive impedance (also referred to as capacitive reactance). It may be understood that alternatively or additionally to the resistive impedance also an electrical conductivity (e.g. between the two or more than two electrodes 302e) may be used.

The electrical impedance sensor 302 may include a recess 302d between the two or more than two electrodes 302e, e.g. defining a distance 302d of the two or more than two electrodes 302e from each other (also referred to as electrode distance 302d). The recess 302d may facilitate detecting particles having different shapes, e.g. round shaped. Illustratively, a portion of a particle may be received in the recess 302d, such that the particle physically contacts the two or more than two electrodes 302e.

The electrical impedance sensor 302 may be configured to change the electrical impedance in response to a particle having a particle size within a first particle size range defined by the electrical impedance sensor (e.g. above the distance 302d). The first particle size range may be defined by the distance 302d of adjacent electrodes of the two or more than two electrodes 302e, e.g. be more than the distance 302d. Illustratively, a particle having an extension greater than the distance 302d may physically contact adjacent electrodes of the two or more than two electrodes 302e. This physical contact may be sensed as drop in the resistive impedance. Alternatively or additionally, the first particle size range may be defined by a depth of the recess 302r (extension perpendicular to the distance 320d) between adjacent electrodes of the two or more than two electrodes 302e. Illustratively, a less deep recess 302r may just allow flatter particles (e.g. flakes) to physically contact the adjacent electrodes of the two or more than two electrodes 302e. This may enable to distinguish between the shape of the particles (also referred to as particle shape). In analogy, the area between the adjacent electrodes of the two or more than two electrodes 302e may be shaped to define a certain first particle size range or shape. Illustratively, the topography of the electrical impedance sensor 302 (e.g. the recess 302r) may limit at least one of the particle size and particle shape physically contacting adjacent electrodes of the two or more than two electrodes 302e.

The capacitive impedance may be defined by the distance 302d of the two or more than two electrodes 302e and an relative (electric) permittivity (also referred to as dielectric permittivity) between the two or more than two electrodes 302e (e.g. spatially averaged). The dielectric permittivity between the two or more than two electrodes 302e in a particle-free operation may be defined by a reference fluid (e.g. a liquid or gaseous medium) in which the electrical impedance sensor 302 is operated (also referred to as reference dielectric permittivity), e.g. the reference fluid disposed in (e.g. filling) the near field 106f.

If the reference fluid (also referred to as operation fluid) is vacuum or gaseous (e.g. including or formed from a gas), the reference dielectric permittivity may be in the range from about 0.8 to about 1.2, e.g. be substantially about 1. For example, if the reference fluid includes or is formed from air, the reference dielectric permittivity may be substantially 1. If the reference fluid is liquid (e.g. including or formed from water), the reference dielectric permittivity may be in the range from about 10 to about 100. The reference dielectric permittivity may be assigned to a reference capacitive impedance of the electrical impedance sensor 302 (e.g. in particle-free operation).

According to various embodiments, the reference fluid (e.g. an ambient fluid, e.g. an ambient gas) may include or be formed from (molecular) nitrogen, (molecular) carbon dioxide, (molecular) methane and (molecular) oxide. For example, a medium to be measured (e.g. an aerosol) may include the reference fluid. According to various embodiments, a fluid may be understood as being at least one of liquid and gaseous, e.g. including or formed from at least one of a gas of a liquid. A fluid may be understood as a substance that continually deforms (flows) under an applied shear stress. A fluid may be understood as adapting the shape of a surface it is in contact with, e.g. adapting the shape of a container it is disposed in.

The electrical impedance sensor 302 may be configured to at least one of generate and modify an electrical signal representing the actual dielectric permittivity (e.g. averaged over the near field 106f). The electrical signal representing the reference dielectric permittivity in (dielectric permittivity of the reference fluid in particle-free operation) may be also referred to as reference signal. For example, an (e.g. alternating) first electrical signal may be supplied to the electrical impedance sensor 302 via the first contact line 108a of the first plurality of contact lines 108a, 108b. The (e.g. alternating) first electrical signal (also referred to as input signal or word signal) may be modified by the electrical impedance sensor 302 in accordance to the capacitive impedance of the electrical impedance sensor 302 into a second electrical signal (also referred to as output signal or bit signal). The electrical impedance sensor 302 may output the second electrical signal via the first contact line 118a of the second plurality of contact lines 118a, 118b, 118c. The output signal may be sensed by a processing circuit and compared to the input signal. A difference of the input signal and the output signal (illustratively, the modification) may represent the actual capacitive impedance of the electrical impedance sensor 302.

A dielectric permittivity of a particle approaching (e.g. entering the near field 106f of) the electrical impedance sensor 302 may differ from the reference dielectric permittivity, thereby causing a change in the capacitive impedance of the electrical impedance sensor 302. In other words, the capacitive impedance defined by the two or more than two electrodes 302e may change in response to a particle at least one of adsorbed and approaching to the electrical impedance sensor 302.

The processing circuit may be configured to provide a parameter (also referred to as measurement result) representing a difference of the capacitive impedance of the electrical impedance sensor 302 from its reference capacitive impedance.

According to various embodiments, the resistive impedance may be defined by a distance 302d of the two or more than two electrodes 302e and a (electric) resistivity (and respective electric conductivity) between the two or more than two electrodes 302e (e.g. spatially averaged). The resistivity between the two or more than two electrodes 302e in a particle-free operation may be defined by the reference fluid in which the electrical impedance sensor 302 is operated (also referred to as reference resistivity), e.g. the reference fluid disposed in (e.g. filling) the near field 106f. The reference resistivity may be assigned to a reference resistive impedance of the electrical impedance sensor 302.

The electrical impedance sensor 302 may be configured to at least one of generate and modify an electrical signal representing the actual resistivity (e.g. averaged over the near field 106f). The electrical signal representing the reference resistivity (resistivity in particle-free operation) may be also referred to as reference signal. For example, an (e.g. direct or alternating) first electrical signal may be supplied to the electrical impedance sensor 302 via the first contact line 108a of the first plurality of contact lines 108a, 108b. The first electrical signal may be modified in accordance to the resistive impedance of the electrical impedance sensor 302 into a second electrical signal. The electrical impedance sensor 302 may output the second electrical signal via the first contact line 118a of the second plurality of contact lines 118a, 118b, 118c. The output signal may be sensed by a processing circuit and compared to the input signal. A difference of the input signal and the output signal may represent the actual resistive impedance of the electrical impedance sensor 302.

A resistivity of a particle approaching (e.g. entering the near field 106f of) the electrical impedance sensor 302 may differ from the reference resistivity, thereby causing a change in the resistive impedance of the electrical impedance sensor 302. In other words, the resistive impedance of the two or more than two electrodes 302e may change in response to a particle at least one of adsorbed and approaching to the electrical impedance sensor 302. For example, the resistive impedance of the electrical impedance sensor 302 may be defined by a particle physically contacting at least one two of the two or more than two electrodes 302e.

The processing circuit may provide a parameter representing a difference of the resistive impedance of the electrical impedance sensor 302 from its reference resistive impedance.

The electrical impedance sensor 302 may be operated in a resistive mode sensing the resistive impedance, e.g. by modifying a direct voltage. Alternatively or additionally, the electrical impedance sensor 302 may be operated in a capacitive mode sensing the capacitive impedance, e.g. by modifying an alternating voltage.

Figure 4B:
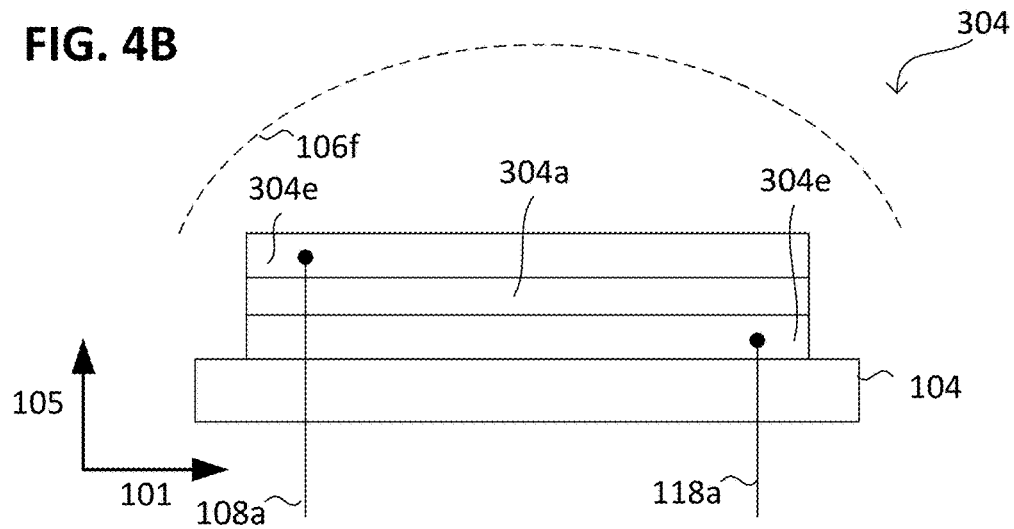

FIG. 4B illustrates a photoelectrical sensor 304 for particle analysis in a schematic cross sectional view (e.g. parallel to direction 103).

The photoelectrical sensor 304 may include the two or more than two electrodes 302e separated from each other by a photoelectrical active region 304a. The two or more than two electrodes 302e may be mounted on the support layer 104, and e.g. may be disposed over each other (alternatively, the may be disposed similarly as shown in FIG. 4A).

By way of example, at least a first electrode 302e of the two or more than two electrodes 302e may be electrically coupled to a first contact line 108a of the first plurality of contact lines 108a, 108b. Alternatively or additionally, at least a second electrode 302e of the two or more than two electrodes 302e may be electrically coupled to a first contact line 118a s of the second plurality of contact lines 118a, 118b, 118c.

The photoelectrical active region 304a may include or be formed from a light-dependent resistor (also referred to as photoresistor). The photoresistor may include or be formed from a semiconductor material (e.g. doped or undoped). A resistance of the photoresistor may decrease with increasing incident electromagnetic radiation (photons, e.g. light), e.g. its intensity. In other words, the photoelectrical active region 304a may be configured for photoconductivity. The photoelectrical active region 304a may define a resistive impedance of the photoelectrical sensor 304 through the photoelectrical active region 304a (in other words, between the two or more than two electrodes 302e).

Alternatively or additionally, the photoelectrical active region 304a may include or be formed from a light-sensitive semiconductor unipolar-junction (also referred to as photojunction). The photojunction may include or be formed from at least one interface between two semiconductor materials differing in their doping type (e.g. p-doping and n-doping), e.g. at least one light-sensitive pn-junction. By way of example, the photoelectrical active region 304a may include at least one of a phototransistor and a photodiode. The photoelectrical active region 304a may be configured to convert electromagnetic radiation energy into electrical energy (illustratively, by absorption of the electromagnetic radiation), e.g. in form of at least one of an electrical voltage and an electrical current (also referred to as photocurrent). The current and voltage generated may increase with increasing incident electromagnetic radiation (photons, e.g. light), e.g. its intensity.

The photoelectrical sensor 304 may be configured to at least one of generate and modify an electrical signal representing the incident electromagnetic radiation intensity (e.g. averaged over the near field 1060. The electric response of the photoelectrical sensor 304 (e.g. generated electric energy or electric dissipation due to the resistivity) in a particle-free operation may be defined by a background illumination in which the electrical impedance sensor 302 is operated (also referred to as reference illumination). The reference illumination may be assigned to a reference response of the photoelectrical sensor 304. The reference illumination may be defined by at least one of natural illumination (ambient illumination) and artificial illumination. The electrical signal representing the reference illumination (illumination in particle-free operation) may be also referred to as reference signal.

A particle approaching (e.g. entering the near field 106f of) the photoelectrical sensor 304 may alter the electromagnetic radiation intensity received by the photoelectrical sensor 304 (also referred to as shading), e.g. its photoelectrical active region 304a, thereby causing a change in the electric response of the photoelectrical sensor 304. In other words, the photoelectrical sensor may be configured to modify an electric charge movement capability in response to receiving electromagnetic radiation energy, such that an electrical output of the photoelectrical sensor changes in response to a particle shading the photoelectrical sensor. For example, an (e.g. alternating or direct) first electrical signal (e.g. the bias current) may be supplied to the electrical photoelectrical sensor 304 via the first contact line 108a of the first plurality of contact lines 108a, 108b. The first electrical signal may be modified in accordance to the electric response of the photoelectrical sensor 304 into a second electrical signal (also referred to as output signal or bit signal). The photoelectrical sensor 304 may output the second electrical signal via the first contact line 118a of the second plurality of contact lines 118a, 118b, 118c. The output signal may be sensed by a processing circuit and compared to the input signal. A difference of the input signal and the output signal may represent the actual illumination of the photoelectrical sensor 304.

The photoelectrical active region 304a may be operated in a photovoltaic mode (e.g. with zero bias current), in which the generated photocurrent is restricted (e.g. set to constant) such that the generated voltage increases with increasing incident electromagnetic radiation. Alternatively or additionally, the photoelectrical active region 304a may be operated in photoconductive mode (e.g. with reverse biased current), in which the generated photocurrent increases with increasing incident electromagnetic radiation. In photovoltaic mode, the input signal may be zero.

Figure 4C:
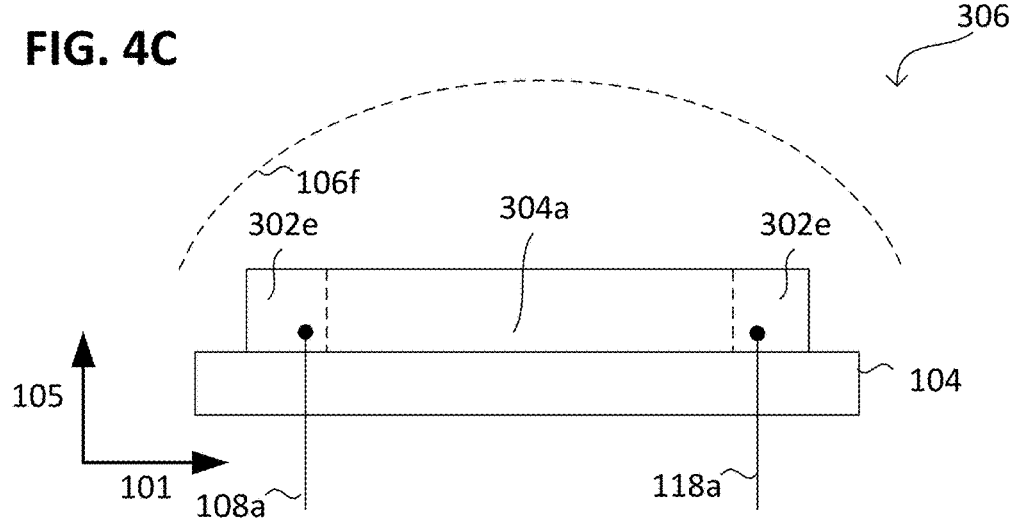

FIG. 4C illustrates an electrochemical fluid sensor 306 for particle analysis in a schematic cross sectional view (e.g. parallel to direction 103).

The electrochemical fluid sensor 306 may include an electrochemical active region 304a. The electrochemical active region 304a may be mounted on the support layer 104. The electrochemical active region 304a may optionally include two or more than two optional electrodes 302e contacting the electrochemical active region 304a.

By way of example, the electrochemical active region 304a may be electrically coupled between the first contact line 108a of the first plurality of contact lines 108a, 108b and the first contact line 118a s of the second plurality of contact lines 118a, 118b, 118c, e.g. via the two or more than two optional electrodes 302e, similar as described before.

The electrochemical active region 304a may include or be formed from a fluid-sensitive electrical impedance (e.g. at least one of resistive impedance and capacitive impedance). The electrochemical active region 304a may include or be formed from a semiconductor material (e.g. an oxide-semiconducting material like tin dioxide). An electrical impedance of the electrochemical active region 304a may change when being in contact with a reference fluid (e.g. a liquid or gaseous medium) in which the electrochemical fluid sensor 306 is operated (also referred to as reference impedance), e.g. the reference fluid disposed in (e.g. filling) the near field 106f. The change in electrical impedance may represent a (reversible) chemical change in the electrochemical active region 304a, e.g. due to the reference fluid may at least one of chemically react with and be adsorbed by the electrochemical active region 304a.

The electrochemical fluid sensor 306 may be configured to modify an electrical signal representing the presence of the reference fluid (e.g. averaged over the near field 1060. The electrical signal representing a particle-free operation may be also referred to as reference signal. For example, an (e.g. alternating or direct) first electrical signal may be supplied to the electrochemical fluid sensor 306 via the first contact line 108a of the first plurality of contact lines 108a, 108b. The first electrical signal may be modified in accordance to the electric impedance of the electrochemical fluid sensor 306 into a second electrical signal. The electrochemical fluid sensor 306 may output the second electrical signal via the first contact line 118a of the second plurality of contact lines 118a, 118b, 118c. The output signal may be sensed by a processing circuit and compared to the input signal. A difference of the input signal and the output signal may represent the presence of reference fluid at the electrochemical fluid sensor 306.

A particle approaching (e.g. entering the near field 106f of) the electrochemical fluid sensor 306 may reduce the area of the electrochemical active region 304a exposed to the reference fluid, thereby causing a change in the electric impedance of the electrochemical fluid sensor 306. In other words, the fraction of a sensing area of the electrochemical fluid sensor 306, which is exposed to the reference fluid, may be reduced due to the particle. In general, the sensing area of a sensor element may refer to as the cross sectional area of the sensor element which is configured to sense particles.

In other words, electrochemical fluid sensor 306 may be configured to generate or modify an electrical signal in response to sensing a reference fluid. The electrochemical fluid sensor 306 may be configured to sense at least one of a presence, a concentration, and a partial pressure of the reference fluid.

Figure 5A:
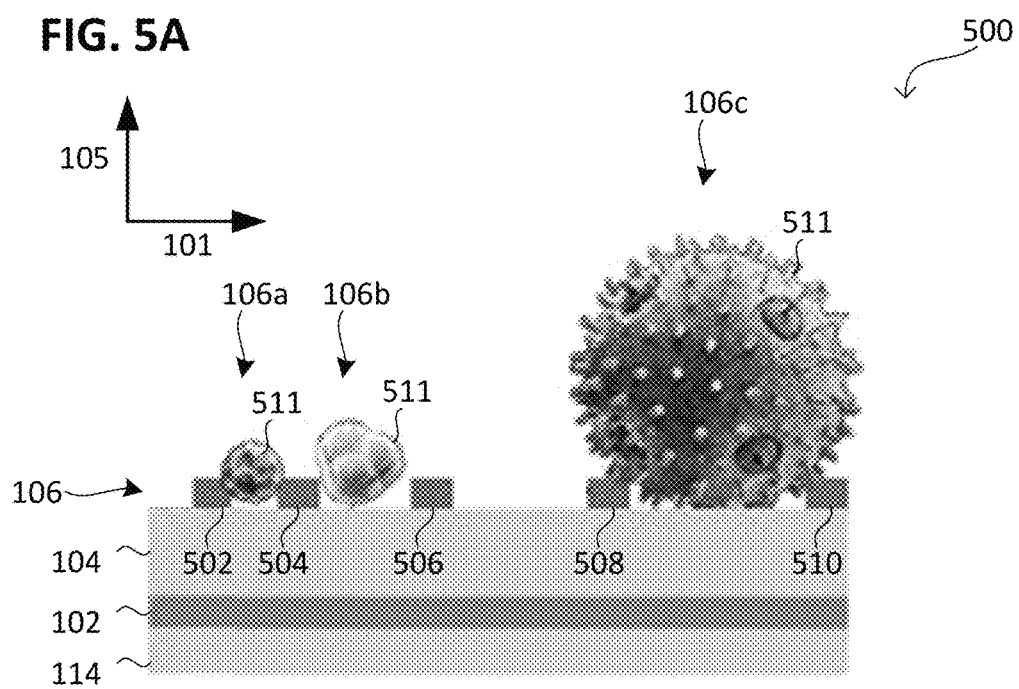
FIG. 5A and FIG. 5B respectively show a sensor arrangement according to various embodiments.
Figure 5B:
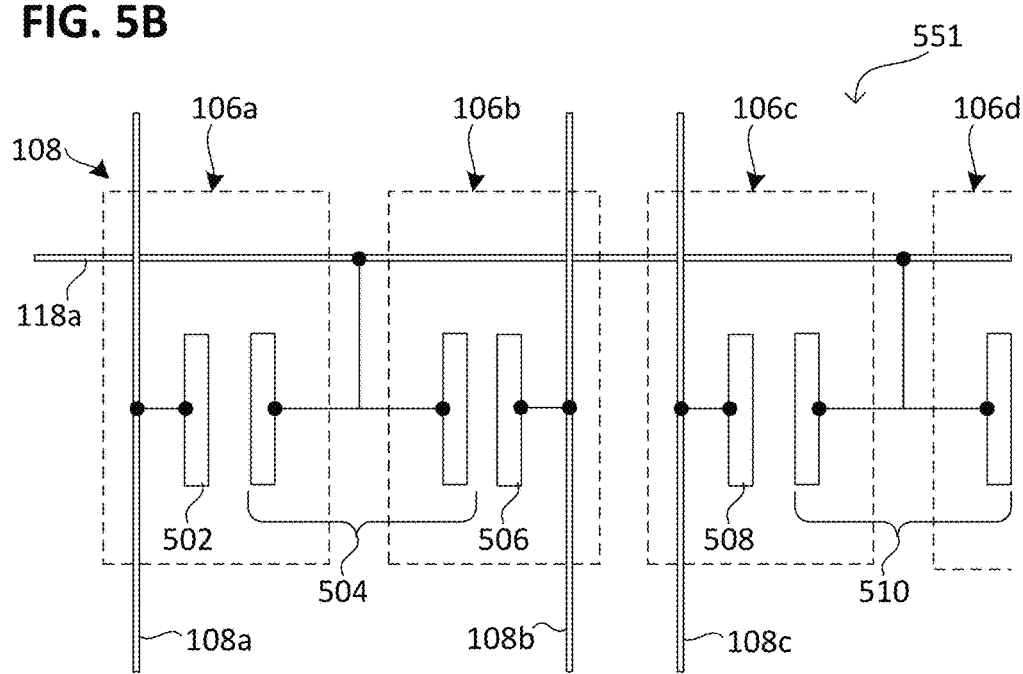

FIG. 5A illustrates a sensor arrangement 500 for particle analysis according to various embodiments in a schematic side view or first cross sectional view (e.g. parallel to direction 103) and FIG. 5B the sensor arrangement 500 in a schematic circuit diagram.

The sensor arrangement 500 may include the base electrode 102 and a first support layer 104 disposed over the support layer 104. The sensor arrangement 500 may further include a second support layer 114 disposed under the support layer 104. In other words, the base electrode 102 may be disposed between the first and second support layer 104, 114. The second support layer 114 may be part of the substrate.

The sensor arrangement 500 may further include the sensor array including a plurality of sensor elements 106a, 106b, 106c (electrical impedance sensor array 106). Exemplarily, the sensor arrangement 500 is illustrated and described for the electrical impedance sensor array 106. It may be understood, that photoelectrical sensors and electrochemical fluid sensor may be configured similar to the exemplarily described electrical impedance sensors.

According to various embodiments, two adjacent sensor elements 106a, 106b, 106c, 106d may adjoin each other. The electrodes of two adjoining sensor elements 106a, 106b, 106c, 106d may be coupled with each other (e.g. pairwise), e.g. at least one of electrically and physically (e.g. monolithically). Illustratively, two adjacent sensor element of the plurality of sensor elements 106a, 106b, 106c, 106d may include (e.g. pairwise) a common electrode 504, 510. For example, the electrode 502 of a first sensor element 106a and the electrode 502 of a second sensor element 106b may be coupled, e.g. monolithically. Alternatively or additionally, the electrode 510 of a third sensor element 106d and the electrode 510 of a fourth sensor element 106d may be coupled, e.g. monolithically.

The two adjoining sensor element of the plurality of sensor elements 106a, 106b, 106c, 106d having at least one common electrode 504, 510 may be also referred to as dual sensor element 106a, 106b (having three electrodes and two sensing areas between them). This may increase at least one of the number of sensor element per area (sensor element density) and the total area of the sensor arrangement 500 which is configured to sense particles (thereby reducing the number of undetected particles).

According to various embodiments, a distance between the electrodes of a sensor element of the plurality of sensor elements 106a, 106b, 106c, 106d may define a cross sectional area of the sensor element which is configured to sense particles. Alternatively or additionally, an extension (perpendicular to the distance) of the electrodes of a sensor element of the plurality of sensor elements 106a, 106b, 106c, 106d may define the cross sectional area of the sensor element which is configured to sense particles 511.

At least two sensor elements of the plurality of sensor elements 106a, 106b, 106c, 106d may differ in the distance between its electrodes. Alternatively or additionally, at least two sensor elements of the plurality of sensor elements 106a, 106b, 106c, 106d may differ in the extension of its electrodes. This may enable to distinguish between particles, which differ in at least one of their particle size or their shape.

Figure 6A:
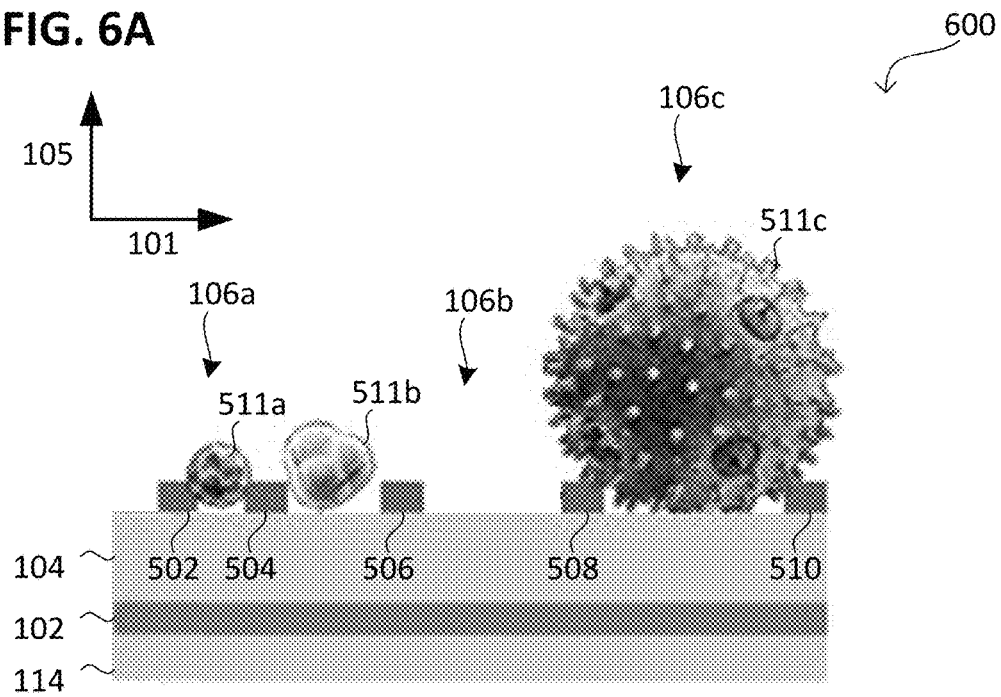
FIG. 6A and FIG. 6B respectively show a sensor arrangement according to various embodiments.
Figure 6B:
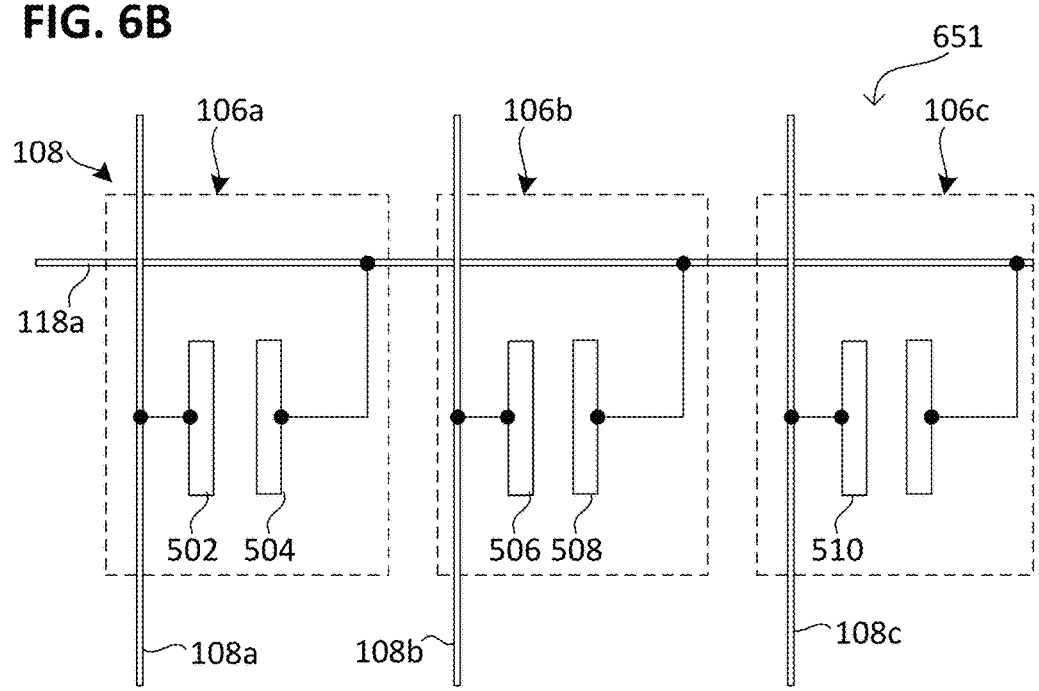

FIG. 6A illustrates a sensor arrangement 600 for particle analysis according to various embodiments in a schematic side view or first cross sectional view (e.g. parallel to direction 103) similar to the previously described sensor arrangement and FIG. 6B the sensor arrangement 600 in a schematic circuit diagram show showing an alternative configuration of the electrical contact structure 108.

The sensor arrangement 600 may include the plurality of sensor elements 106a, 106b, 106c each disposed distant from each other. This may reduce interference between the sensor elements of the plurality of sensor elements 106a, 106b, 106c. In the alternative configuration of the electrical contact structure 108 particles (e.g. particles 511b and 511c) adsorbed between adjacent sensor element of the plurality of sensor elements 106a, 106b, 106c may be not detected. This may increase a dark rate (fraction of not detected particles).

Figure 7A:
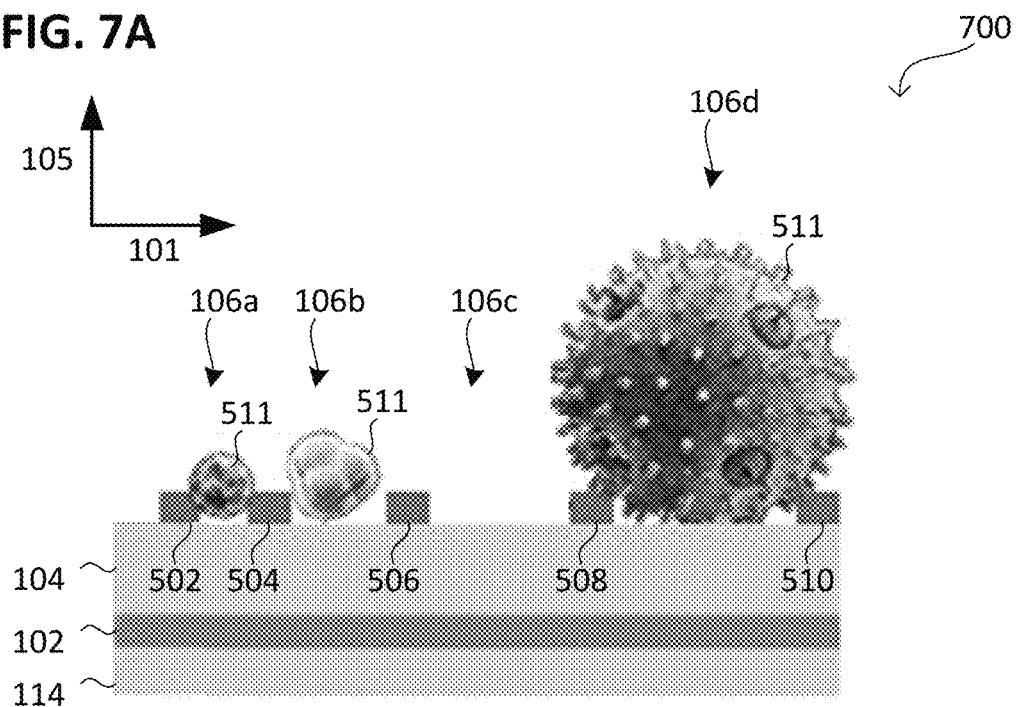
FIG. 7A and FIG. 7B respectively show a sensor arrangement according to various embodiments.
Figure 7B:
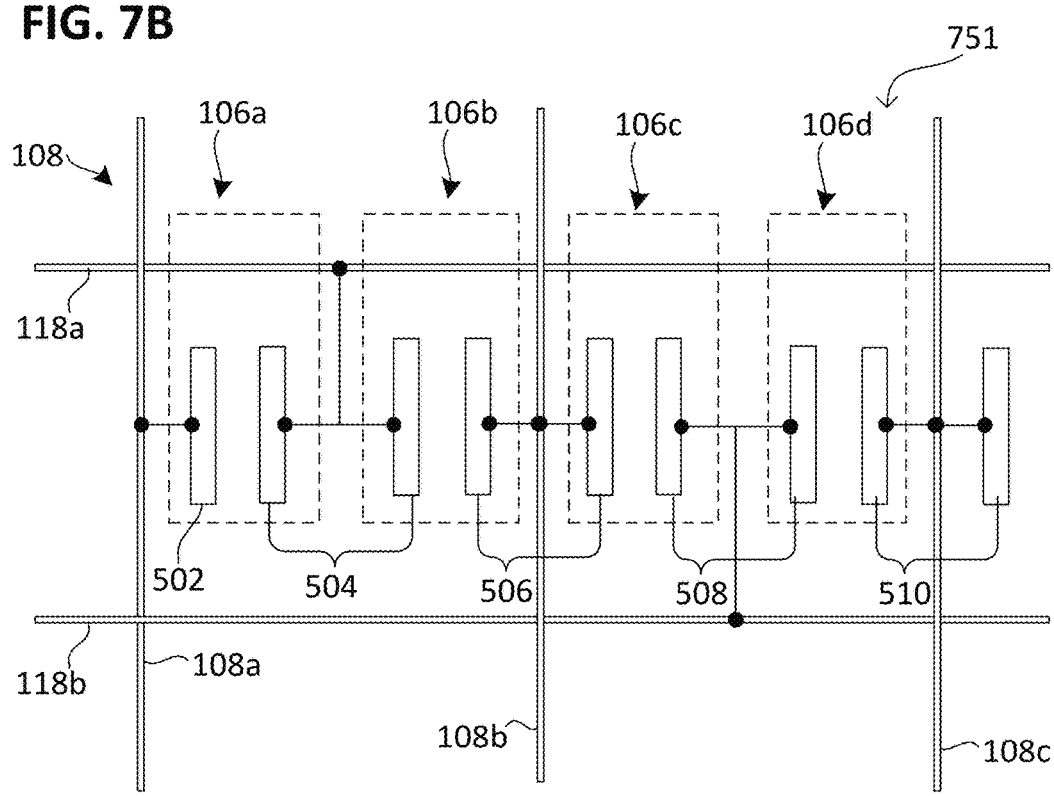

FIG. 7A illustrates a sensor arrangement 700 for particle analysis according to various embodiments in a schematic side view or first cross sectional view (e.g. parallel to direction 103) similar to the previously described sensor arrangement and FIG. 7B the sensor arrangement 700 in a schematic circuit diagram show showing a further alternative configuration of the electrical contact structure 108.

According to various embodiments, each pair of adjacent sensor elements of the plurality of sensor elements 106a, 106b, 106c, 106d may adjoin each other. The electrodes of two adjoining sensor elements 106a, 106b, 106c, 106d may be coupled with each other (e.g. pairwise), e.g. at least one of electrically and physically (e.g. monolithically). For example, each electrode 502, 504, 506, 508, 510 may be assigned to two sensor elements of the plurality of sensor elements 106a, 106b, 106c, 106d. In other words, two adjacent dual sensor elements of the plurality of sensor elements 106a, 106b, 106c, 106d may include a common (e.g. monolithically) electrode. In this configuration of the electrical contact structure 108, a first plurality of electrodes 502, 506, 510 may be contacted by the first plurality of contact lines 108a, 108b, 108c. A second plurality of electrodes 504, 508 may be contacted by the second plurality of contact lines 118a, 118b, 118c. Each electrode of the second plurality of electrodes 504, 508 may be disposed between two electrodes first plurality of electrodes 502, 506, 510. Adjacent electrodes of the second plurality of electrodes 504, 508 may differ in the contact line of the second plurality of contact lines 118a, 118b, 118c they are connected with.

In this configuration of the electrical contact structure 108, at least one of the number of sensor element per area (sensor element density) and the total area of the sensor arrangement 700 may be maximized.

Figure 8A:
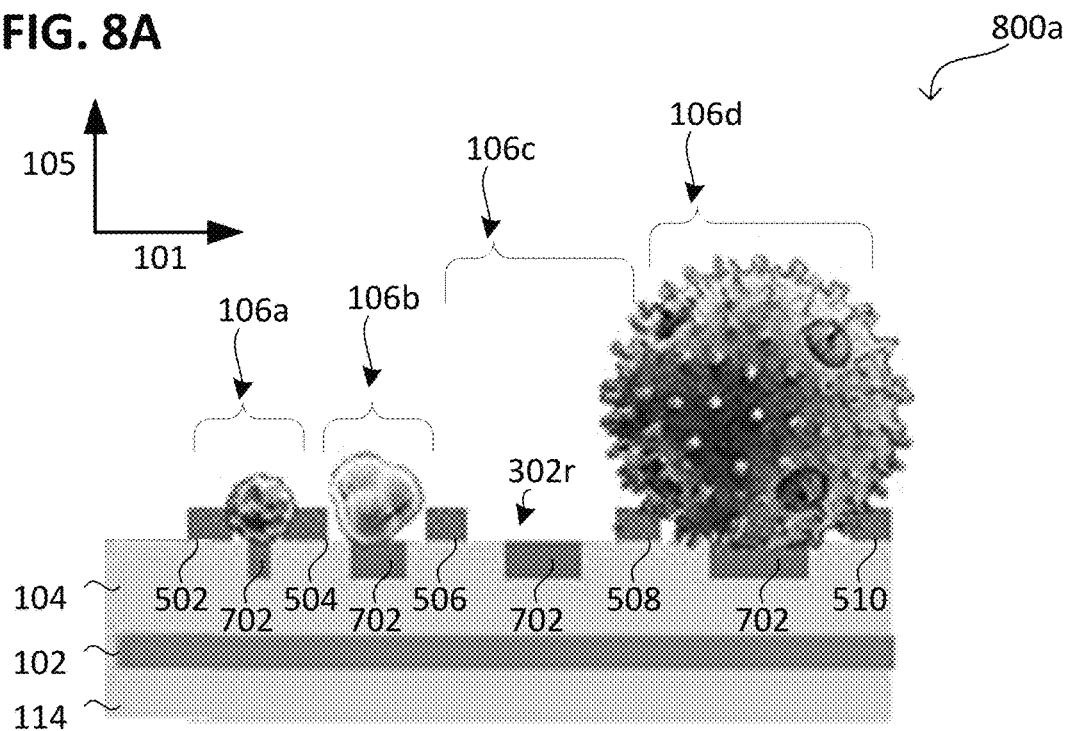
FIG. 8A to FIG. 8B respectively show a sensor arrangement according to various embodiments.

FIG. 8A illustrates a sensor arrangement 800a for particle analysis according to various embodiments in a schematic side view or first cross sectional view (e.g. parallel to direction 103) similar to the previously described sensor arrangement.

According to various embodiments, the two or more than two electrodes may include three electrodes. For example, between the two electrodes 502, 504 of the each sensor element of the plurality of sensor elements 106a, 106b, 106c, 106d, a third electrode 702 may be disposed, e.g. in the recess 302r. The three electrodes may enable a three-point contact for sensing the particle. Using a three-point contact may reveal more detailed particle information than a two-point contact. By way of example, very small particles may contact a maximum of two adjacent electrodes of the three electrodes, moderate sized particles may contact all three electrodes, and very large particles may contact a maximum of two distant electrodes of the three electrodes. This may enable to define more than one first particle size.

Each sensor element of the plurality of sensor elements 106a, 106b, 106c, 106d may be electrically coupled by (e.g.

at least two contact lines of) an electrical contact structure 108, e.g. configured similar to the electrical contact structure 108 of the sensor arrangement 700.

Figure 8B:
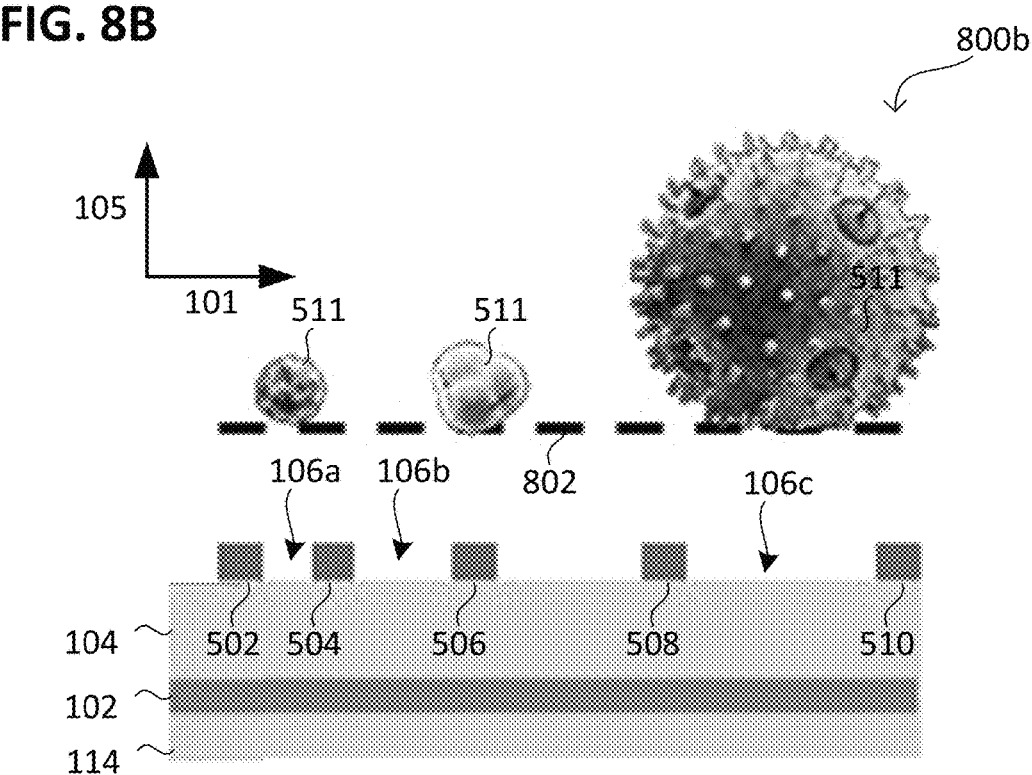

FIG. 8B illustrates a sensor arrangement 800*b* for particle analysis according to various embodiments in a schematic side view or first cross sectional view (e.g. parallel to direction 103) similar to the previously described sensor arrangement, e.g. a reference device with particle filter.

According to various embodiments, the sensor arrangement may include a filter layer 802 covering the sensor arrangement 800*b* at least partially (in other words, partially or completely). The filter layer 802 may be disposed distant from the sensor elements of the sensor arrangement 800*b*, such that a gap is formed between the filter layer 802 and the sensor elements of the sensor arrangement 800*b*. For example, the filter layer 802 may be at least one of perforated and fluid-permeable.

The filter layer 802 may be configured to filter a particle adsorption to the sensor arrangement 800*b*, e.g. by size or density. For example, the filter layer 802 may extend through the near field 106*f*.

The filter layer 802 may enable to limit the particle size adsorbed by the plurality of sensor elements 106*a*, 106*b*, 106*c*, 106*d*, thereby refining the gain of particle information. Optionally, the particles may be prevented to contact the plurality of sensor elements 106*a*, 106*b*, 106*c*, thereby facilitating to measure their dielectric properties, e.g. independent from their electrical conductivity or size.

According to various embodiments, the filter layer 802 may include or be formed from a first filter region, e.g. covering a first section (e.g. a first reference section) of the sensor array. The first filter region may be fluid-permeable and non-particle-permeable (in this case also referred to as reference filter region). In other words, the first filter region may prevent a particle contamination of the plurality of sensor elements 106*a*, 106*b*, 106*c*. This may facilitate to obtain a reference signal, e.g. during the sensing operation mode. Alternatively or additionally, this may allow reference measurements without prior cleaning, e.g. for increasing the frequency of reference measurements at constant cleaning frequency.

Alternatively or additionally, the filter layer 802 may include or be formed from a second filter region, e.g. covering a second section (e.g. a second reference section) of the sensor array. Illustratively, the second filter region may include through holes (perforation) which may allow particles fitting in the through holes by at least one of size and shape to pass through the second filter region. The second filter region may provide particle filtering configured for filtering particles attracted to the covered section of the sensor array by at least one of particle size and shape.

For example, the second filter region may define a particle size range (e.g. a second particle size range). The second filter region may be permeable for particles (e.g. by perforation) having a particle size within the particle size range (in this case also referred to as size filter region). Alternatively or additionally, the second filter region may be permeable for particles (e.g. by perforation) having a particle shape within a second particle shape range (in this case also referred to as shape filter region).

For example, the particle information may be compared between sensor elements of the plurality of sensor elements 106*a*, 106*b*, 106*c*, 106*d* differing in their coverage by a filter layer 802. Alternatively or additionally, the particle information may be compared between sensor elements of the plurality of sensor elements 106*a*, 106*b*, 106*c*, 106*d* covered by different filter regions, e.g. differing in at least one of the particle size passing through the filter region, the shape passing through the filter region, the distance from the sensor elements.

Optionally, the filter layer 802 may be electrically connected to the processing circuit. The processing circuit may be configured to provide at least one electrical potential to the filter layer 802. A first electrical potential of the at least one electrical potential may enable to clean the filter layer 802 (in other words, to remove particles 511 from the filter layer 802), e.g. by electrostatic repulsion. Alternatively or additionally, a second electrical potential at least one electrical potential may be configured to compensate the attraction potential of the base electrode 102 (also referred to as compensation potential), e.g. in order to keep the filter layer 802 free from particles 511. For example, the processing circuit may be configured to provide the first electrical potential in a cleaning operation mode. Alternatively or additionally, the processing circuit may be configured to provide the second electrical potential in a sensing operation mode (e.g. for a reference measurement).

FIG. 9A illustrates a sensor arrangement 900 for particle analysis in a schematic top view or second cross sectional view perpendicular to the first cross sectional view (e.g. parallel to direction 105) and FIG. 9B illustrates the sensor arrangement 900 in an optional detailed configuration, a capacitor device for impedance measurement.

The sensor array of the sensor arrangement 900 may include or be formed from at least two sections 900*a*, 900*b*, 900*c*, 900*d* (e.g. two, three, four, five, more than five, etc.). For example, the sensor array of the sensor arrangement 900 may include or be formed from a first section 900*a*, a second section 900*b*, an optional third section 900*c*, an optional fourth section 900*d*, and optional one or more further sections Each section at least two sections 900*a*, 900*b*, 900*c*, 900*d* may include or be formed from at least one sensor element, e.g. a plurality of sensor elements 106*a*, 106*b*, 106*c*, 106*d*.

At least two sections 900*a*, 900*b*, 900*c*, 900*d* of the sensor array may differ in the coverage by a filter layer 802. Alternatively or additionally, if the at least two sections 900*a*, 900*b*, 900*c*, 900*d* of the sensor array are covered by a filter layer 802, the at least two sections 900*a*, 900*b*, 900*c*, 900*d* of the sensor array may differ in a permeability of a filter layer 802 (e.g. in at least one of the particle size and the particle shape passing through the filter layer 802). For example, a first section 900*a* may be covered by a filter layer 802, which is non-particle permeable. The first section 900*a* may be used for reference measurements (also referred to as reference section 900*a*). Alternatively or additionally, a second section 900*b* may be non-covered by a filter layer 802 (exposed), thus receiving unfiltered particles.

Alternatively or additionally, two sections of the at least two sections 900*a*, 900*b*, 900*c*, 900*d* of the sensor array may differ in the sensor type of their sensor elements.

Alternatively or additionally, two sections of the at least two sections 900*a*, 900*b*, 900*c*, 900*d* of the sensor array may differ their particle size-sensing characteristic. As exemplarily illustrated in FIG. 9B, the sensor elements of the at least two sections 900*a*, 900*b*, 900*c*, 900*d* may be equal in their sensor type, but differ their electrode distance 302*d*. Alternatively or additionally, the sensor elements of two sections of the at least two sections 900*a*, 900*b*, 900*c*, 900*d* may be equal in their sensor type, but differ their topography.

Figure 10A:
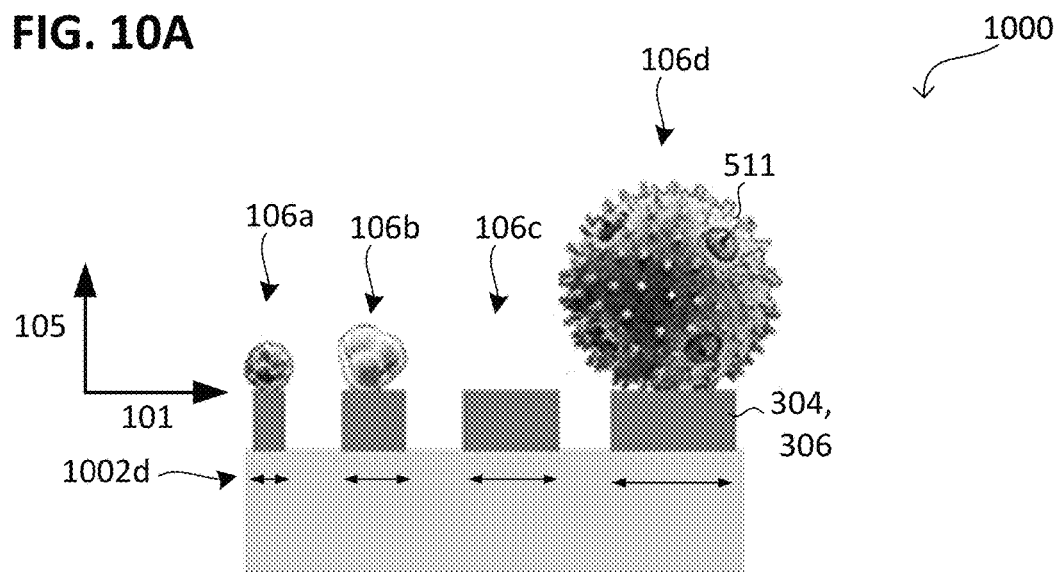
FIG. 10A and FIG. 10B respectively show a sensor arrangement according to various embodiments.
Figure 10B:
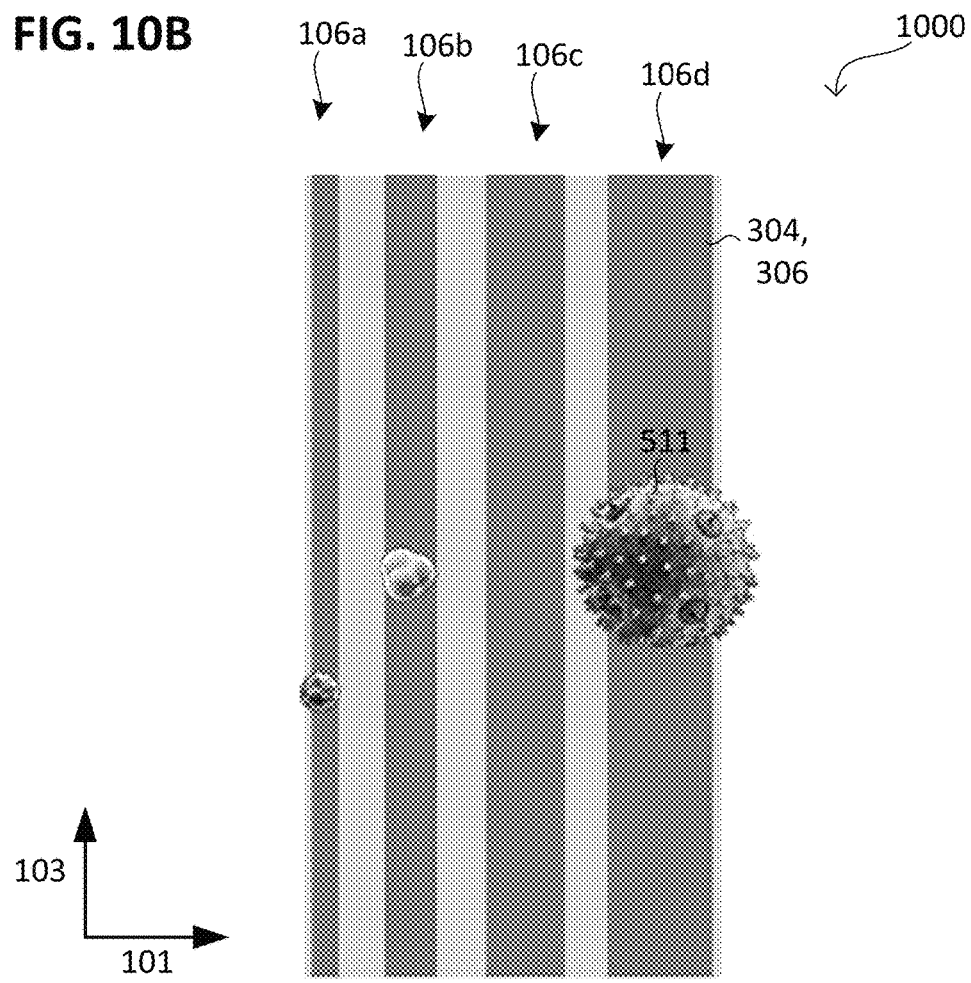

FIG. 10A illustrates a sensor arrangement 1000 for particle analysis in a schematic side view or first cross sectional view (e.g. parallel to direction 103) and FIG. 10B the sensor arrangement 1000 in a schematic top view or second cross sectional view perpendicular to the first cross sectional view (e.g. parallel to direction 105), e.g. a device for gas or light detection measurement (e.g. via shading of the light detector array).

According to various embodiments, The plurality of sensor elements 106a, 106b, 106c, 106d may include or be formed from photoelectrical sensors 304 (e.g. photodiodes, e.g. of a light detector array). According to various similar embodiments, the plurality of sensor elements 106a, 106b, 106c, 106d may include or be formed from electrochemical fluid sensors 306.

At least two sensor elements of the plurality of sensor elements 106a, 106b, 106c, 106d may differ in their particle size-sensing characteristic. For example, At least two sensor elements of the plurality of sensor elements 106a, 106b, 106c, 106d may differ in the size of their active area, e.g. defined by its expansion 1002d.

Further, the plurality of sensor elements 106a, 106b, 106c, 106d may be configured as described herein.

Figure 11:
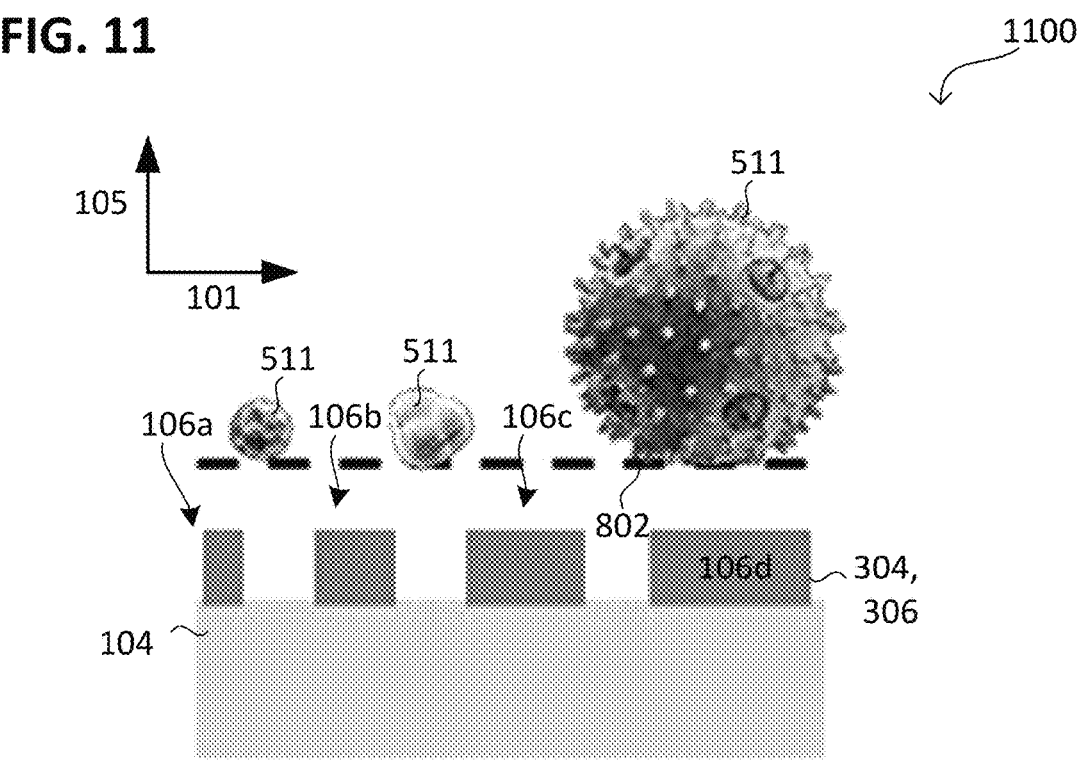
FIG. 11, FIG. 12A and FIG. 12B respectively show a sensor arrangement according to various embodiments.

FIG. 11 illustrates a sensor arrangement 1100 for particle analysis in a schematic side view or first cross sectional view (e.g. parallel to direction 103).

According to various embodiments, the plurality of sensor elements 106a, 106b, 106c, 106d may include or be formed from photoelectrical sensors 304. According to various similar embodiments, the plurality of sensor elements 106a, 106b, 106c, 106d may include or be formed from electrochemical fluid sensor 306.

The sensor arrangement 1100 may include or be formed from a section covered by the filter layer 802. The filter layer 802 may be configured as described herein. For example, the filter layer 802 may include or be formed from a reference filter region. Alternatively or additionally, the filter layer 802 may include or be formed from at least one of a shape filter region and a size filter region.

Particles 511, which are prevented from contacting the plurality of sensor elements 106a, 106b, 106c, 106d by the filter layer 802 may at least partially shade the plurality of sensor elements 106a, 106b, 106c, 106d. In case of photoelectrical sensors 304, the presence of the particles 511 may be recognized. In case of electrochemical fluid sensor 306, the fluid may completely fill the gap between the filter layer 802 and the plurality of sensor elements 106a, 106b, 106c, 106d, thereby allowing a reference measurement.

Figure 12A:
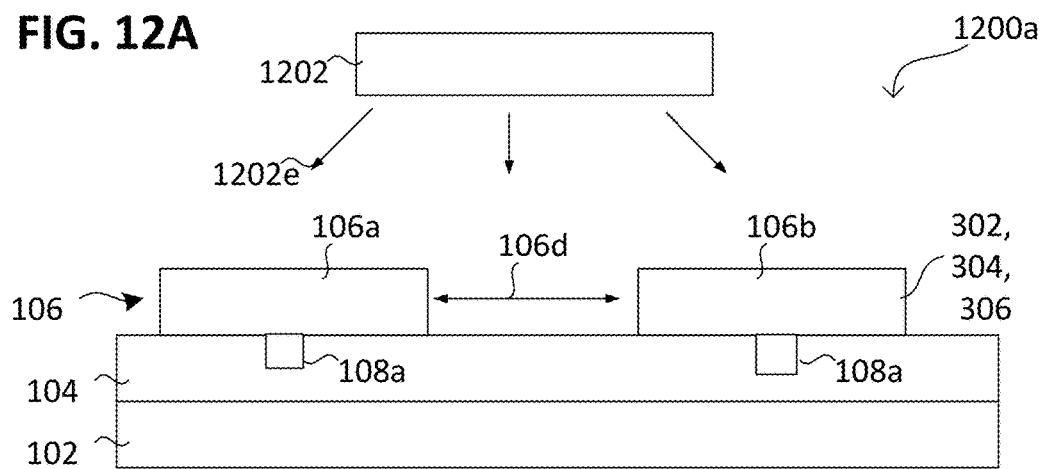

FIG. 12A illustrates a sensor arrangement 1200a for particle analysis in a schematic side view or first cross sectional view (e.g. parallel to direction 103).

The sensor elements 106a, 106b of the sensor arrangement 1200a may include or be formed from photoelectrical sensors 304. The photoelectrical sensors may define a wavelength range (also referred to as sensing range) in which the photoelectrical sensors are configured to be sensitive.

The sensor arrangement 1200a may further include an electromagnetic radiation source 1202. The electromagnetic radiation source 1202 may be configured to emit electromagnetic radiation 1202e (e.g. light) to the sensor elements 106a, 106b of the sensor arrangement 1200a, for example, at least one of the following types of electromagnetic radiation: monochromatic light (e.g. LED light); polychromatic light; continuous visible light; infrared light and ultraviolet light. A wavelength of the electromagnetic radiation 1202e emitted by the electromagnetic radiation source 1202 may be within the sensing range. The electromagnetic radiation source 1202 may enable to be independent from ambient illumination.

The sensor elements 106a, 106b of the sensor arrangement 1200a may include or be formed from photoelectrical sensors 304. The photoelectrical sensors may define a wavelength range (also referred to as sensing range) in which the photoelectrical sensors are configured to be sensitive.

In a similar embodiment, the sensor elements 106a, 106b of the sensor arrangement 1200a may include or be formed from at least one of electrical impedance sensors 302, photoelectrical sensors 304 and fluid sensors 306. The sensor arrangement 1200a may further include a micro-pump 1202, e.g. a microfluidic pump 1202. The micro-pump 1202 may be configured pump a medium to be measured 1202e (e.g. including a reference fluid) to the sensor elements 106a, 106b of the sensor arrangement 1200a. The micro-pump 1202 may enable to be independent from ambient fluid flow.

Figure 12B:
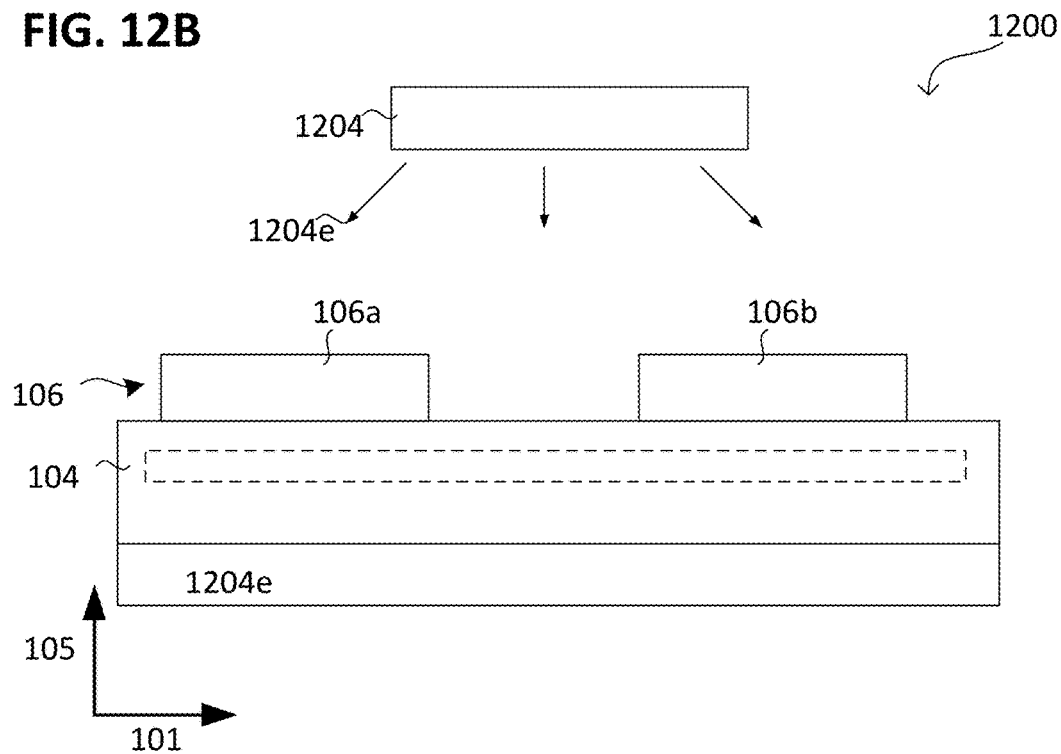

FIG. 12B illustrates a sensor arrangement 1200b for particle analysis in a schematic side view or first cross sectional view (e.g. parallel to direction 103).

The sensor arrangement 1200b may include a cleaning device 1204. The cleaning device 1204 may be configured for removing particles from the sensor array (or from a filter layer 802 if present), e.g. in a cleaning operation mode. The cleaning device 1204 may be controlled by the processing circuit.

According to various embodiments, the cleaning device 1204 may be used in a cleaning operation mode to clean the plurality of sensor elements 106a, 106b, 106c (or the filter layer 802 if present). Alternatively or additionally, the cleaning device 1204 may be configured to remove a particle in a sensing operation mode. The strength of the cleaning effect may be controlled (e.g. increased, stepwise) to determine an adhesion strength of the particle. This may enable to refine particle information.

According to various embodiments, the cleaning device 1204 may include or be formed from a cleaning fluid source. For example, the cleaning fluid source may include a microfluidic pump for emitting the fluid 1204e.

According to various embodiments, the cleaning fluid source may be configured to transfer a fluid 1204e (also referred to as cleaning fluid, e.g. a gaseous cleaning fluid and a liquid cleaning fluid. e.g. the reference fluid) to the plurality of sensor elements 106a, 106b, 106c (or to a filter layer 802 if present) in a cleaning operation mode. The emission of the fluid 1204e may be configured to release a particle from the plurality of sensor elements 106a, 106b, 106c (or from the filter layer 802 if present), e.g. by purging. In other words, the plurality of sensor elements 106a, 106b, 106c may be cleaned from particles.

Alternatively or additionally, the cleaning fluid source may be configured to transfer the fluid 1204e to the plurality of sensor elements 106a, 106b, 106c (or to the filter layer 802 if present) in a sensing operation mode. The intensity of the transfer of the fluid 1204e may be controlled (e.g. increased, stepwise) to determine an adhesion strength of the particle. This may enable to refine particle information.

Alternatively or additionally, the cleaning device 1204 may include or be formed from a heat source. The heat source may be configured to transfer thermal energy 1204e to the sensor array for releasing a particle from the plurality of sensor elements 106a, 106b, 106c (or from a filter layer 802 if present). Thermal energy 1204e may be configured to induce a thermal weakening of thermal breaking of a chemical bonding between the particle and the plurality of sensor elements 106a, 106b, 106c (or the filter layer 802 if present). The heat source may be configured to irradiate the particles (or from a filter layer 802 if present) by heat radiation. Alternatively or additionally, heat source may be thermally connected to the plurality of sensor elements 106a, 106b, 106c (or to the filter layer 802 if present), e.g. by a solid heat connection, to transfer thermal energy. For example, the heat source may be buried in the substrate 102, 104.

Alternatively or additionally, the cleaning device 1204 may include or be formed from a radiation source. The radiation source may be configured to expose the plurality of sensor elements 106a, 106b, 106c (or to a filter layer 802 if present) to radiation 1204e (e.g. at least one of thermal radiation, particle radiation or ultraviolet radiation). The radiation may be configured to release a particle from the plurality of sensor elements 106a, 106b, 106c (or from a filter layer 802 if present). The radiation may be configured to weaken or break a chemical bonding (also referred to as photochemical release) between the particle and the plurality of sensor elements 106a, 106b, 106c (or the filter layer 802 if present).

At least one of the heat source and the radiation source may be used in a cleaning operation mode to clean the plurality of sensor elements 106a, 106b, 106c (or the filter layer 802 if present). Alternatively or additionally, the at least one of the heat source and the radiation source may be configured to weaken or break the chemical bonding in a sensing operation mode. The intensity of the transfer of at least one of the heat and the radiation may be controlled (e.g. increased, stepwise) to determine an adhesion strength of the particle. This may enable to refine particle information.

Alternatively or additionally, the cleaning device 1204 may include or be formed from a repulsion electrode 1204e (e.g. identical with the base electrode or separated from the base electrode). The repulsion electrode 1204e may be electrically connected to the processing circuit (e.g. including a repulsion electrode controller unit). The processing circuit may be configured to provide an electrical potential (also referred to as repulsion potential) to the repulsion electrode 1204e. The repulsion potential may be configured for repulsing particles from the sensor array by electrostatic force. For example, the repulsion potential may be greater than a releasing potential, which defines the electrical potential needed to release particles from the sensor arrangement 1200a.

The repulsion electrode 1204e may be used in a cleaning operation mode to clean the plurality of sensor elements 106a, 106b, 106c (or the filter layer 802 if present). Alternatively or additionally, the repulsion electrode 1204e may be configured to remove a particle in a sensing operation mode. The magnitude of the electrical potential may be controlled (e.g. increased, stepwise) to determine an adhesion strength of the particle. This may enable to refine particle information.

Figure 13A:
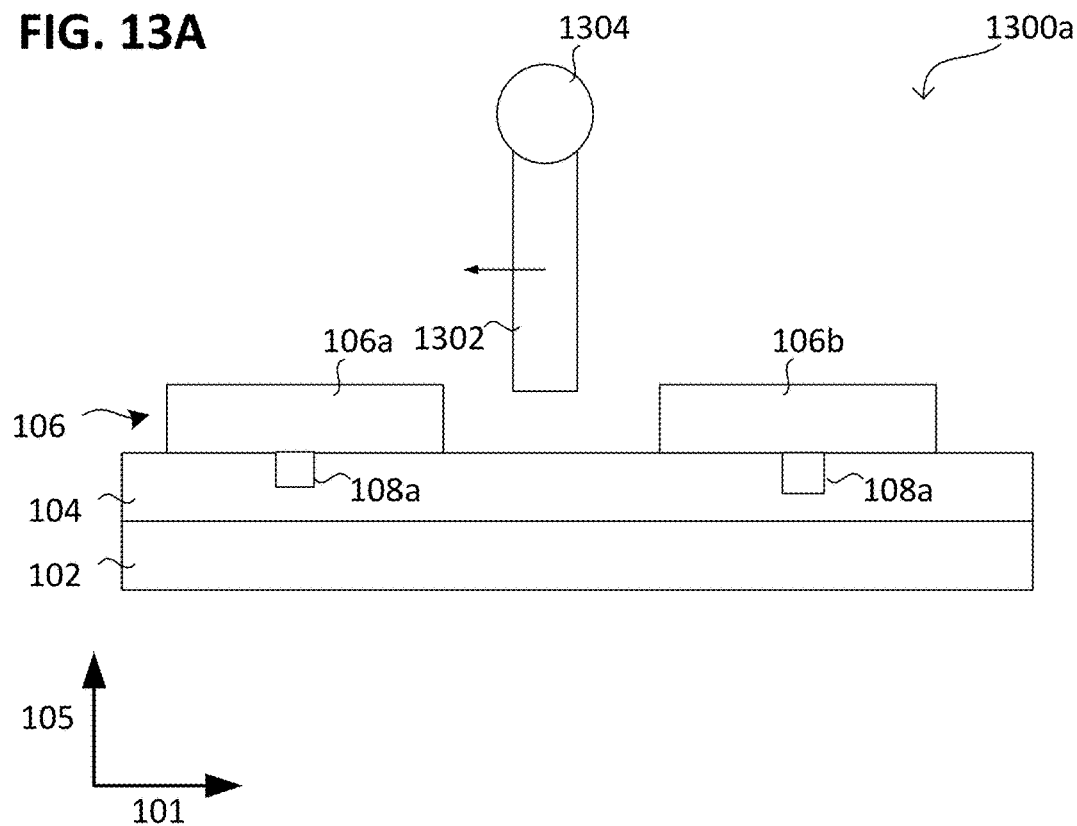
FIG. 13A and FIG. 13B respectively show a sensor arrangement according to various embodiments.

FIG. 13A illustrates a sensor arrangement 1300a for particle analysis in a schematic side view or first cross sectional view (e.g. parallel to direction 103).

According to various embodiments, the cleaning device may include a mechanical wiper 1302 mounted on an actuator 1304. The actuator may be configured to actuate the mechanical wiper 1302 over the plurality of sensor elements 106a, 106b, 106c (or the filter layer 802 if present). The mechanical wiper 1302 may be configured to release a particle from the plurality of sensor elements 106a, 106b, 106c (or the filter layer 802 if present), e.g. by mechanical force.

Figure 13B:
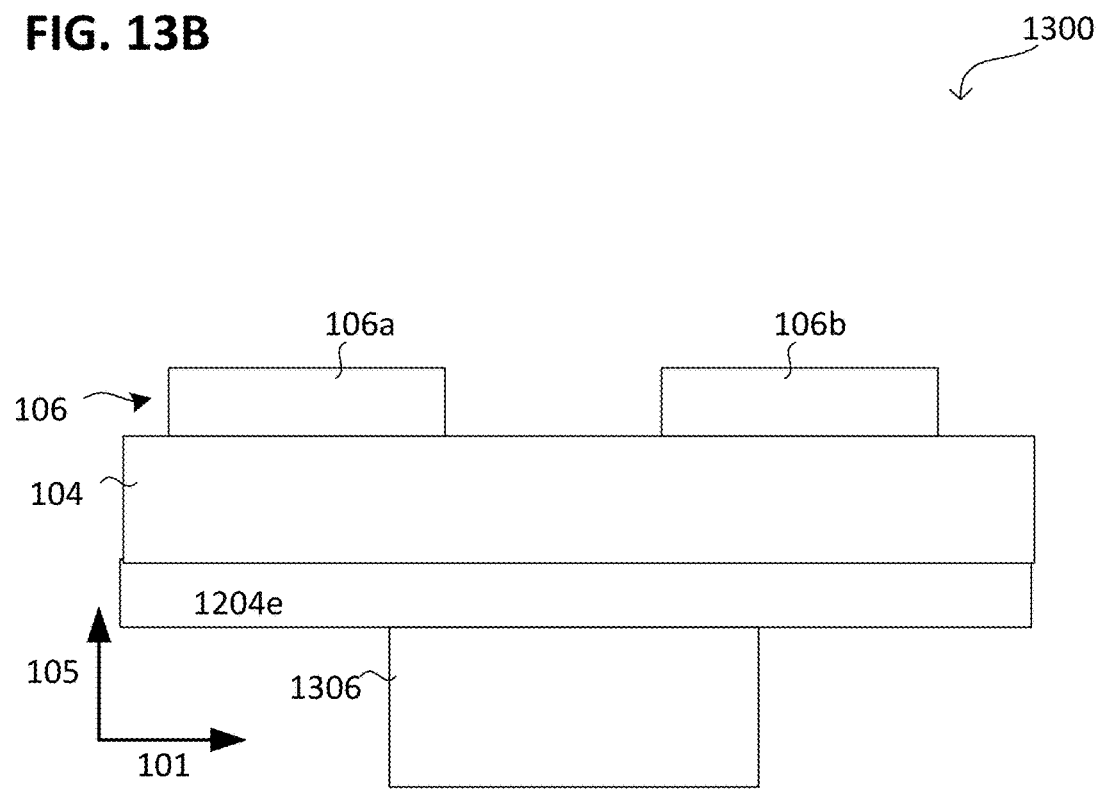

FIG. 13B illustrates a sensor arrangement 1300b for particle analysis in a schematic side view or first cross sectional view (e.g. parallel to direction 103).

According to various embodiments, the cleaning device may include an electromechanical vibrator 1306 (e.g. an acoustical source). The electromechanical vibrator 1306 may be configured to transform electrical energy into mechanical vibration energy. The electromechanical vibrator 1306 may be coupled to the plurality of sensor elements 106a, 106b, 106c (or the filter layer 802 if present) for transferring the mechanical vibration energy. Illustratively, the electromechanical vibrator 1306 may be configured to transfer an alternating mechanical force (mechanical vibration) to the plurality of sensor elements 106a, 106b, 106c (or the filter layer 802 if present). The mechanical vibration may be configured to release a particle from the plurality of sensor elements 106a, 106b, 106c (or the filter layer 802 if present).

The electromechanical vibrator 1306 may be used in a cleaning operation mode to clean the plurality of sensor elements 106a, 106b, 106c (or the filter layer 802 if present). Alternatively or additionally, the electromechanical vibrator 1306 may be configured to remove a particle in a sensing operation mode. The strength of the mechanical vibration may be controlled (e.g. increased, stepwise) to determine an adhesion strength of the particle. This may enable to refine particle information.

Figure 14A:
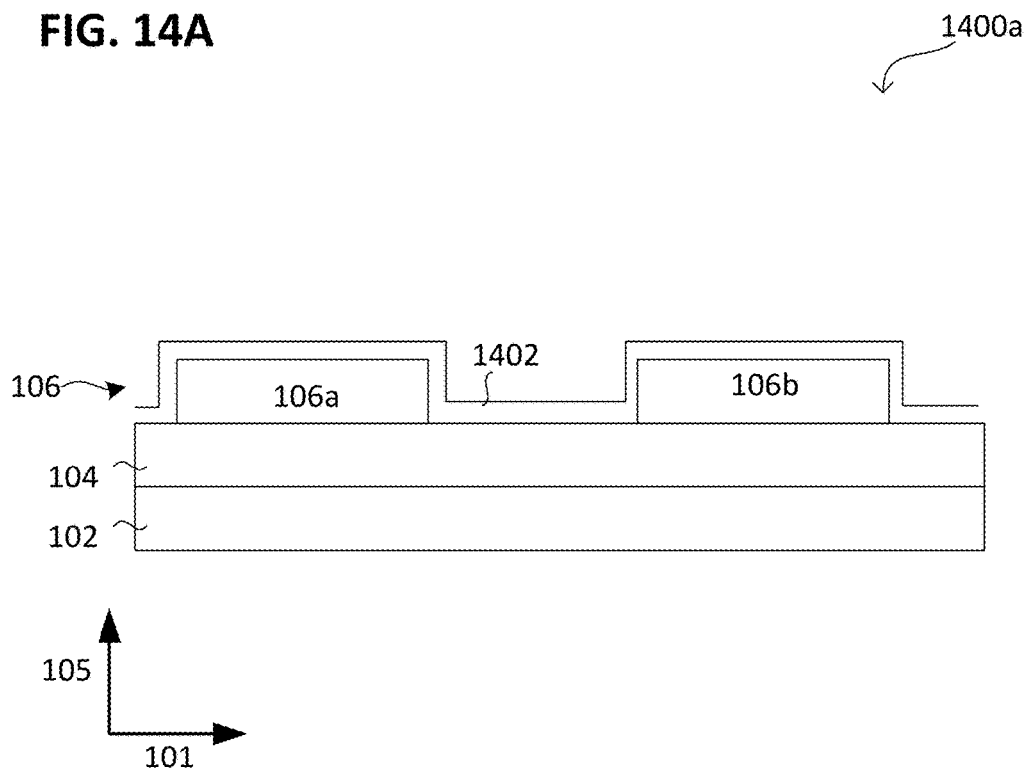
FIG. 14A and FIG. 14B respectively show a sensor arrangement according to various embodiments.

FIG. 14A illustrates a sensor arrangement 1400a for particle analysis in a schematic side view or first cross sectional view (e.g. parallel to direction 103).

The sensor arrangement 1400a may include an anti-adhesion layer 1402 disposed over the plurality of sensor elements 106a, 106b, 106c. The anti-adhesion layer 1402 may be configured to reduce an adhesion force of particles to the plurality of sensor elements 106a, 106b, 106c. For example, an adhesion coefficient of the anti-adhesion layer 1402 may be less than an adhesion coefficient of the plurality of sensor elements 106a, 106b, 106c, e.g. with regard to a particle, e.g. a dielectric material of a particle. The anti-adhesion layer 1402 may include or be formed from a Lotus-effect material and/or Lotus-effect topography. Alternatively or additionally, the anti-adhesion layer 1402 may include or be formed from self-assembled monolayers, alkanethiols with specific head-groups, and other 2D-materials.

Figure 14B:
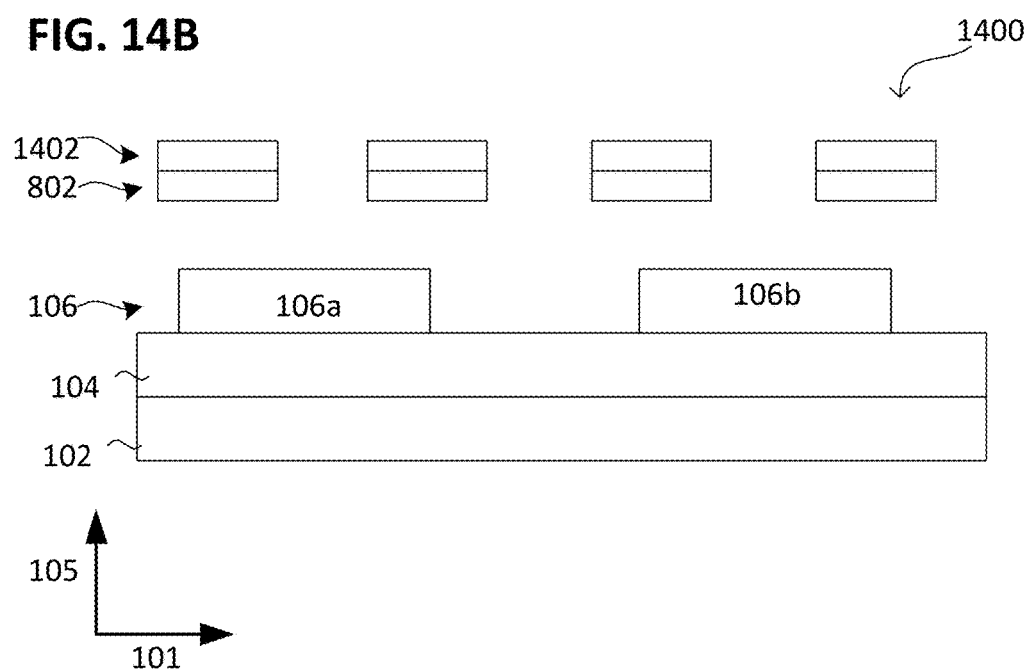

FIG. 14B illustrates a sensor arrangement 1400b for particle analysis in a schematic side view or first cross sectional view (e.g. parallel to direction 103).

The sensor arrangement 1400a may include an anti-adhesion layer 1402 disposed over the filter layer 802. The anti-adhesion layer 1402 may be configured to reduce an adhesion force of particles to the filter layer 802. For example, an adhesion coefficient of the anti-adhesion layer 1402 may be less than an adhesion coefficient of the filter layer 802, e.g. with regard to a particle, e.g. a dielectric material of a particle.

FIG. 15A illustrates a sensor arrangement 1500 for particle analysis in a schematic diagram.

The sensor arrangement 1500 may include a process controller 1502. The process controller 1502 may include a processing circuit 1502p. The processing circuit 1502p may be electrically coupled to the sensor array 106 via the contact structure 108. The processing circuit 1502p may be configured for processing at least one electrical signal generated or modified by the sensor array 106. The processing circuit 1502p may be further configured to address an individual sensor element 106a of the sensor array 106 via the contact structure 108. The processing circuit 1502p may be configured to assign an individual address to each sensor element of the sensor array 106 and provide address data representing the individual address.

The processing circuit 1502p may be configured to operate the sensor array 106 in more than one operation mode, e.g. at least one sensing operation mode and/or the cleaning operation mode. The at least one sensing operation mode may include at least one of the following operation modes: a first operation mode for determining an adhesion strength; a second operation mode for determining an adsorption event; a third operation mode for determining an desorption event; a fourth operation mode for determining a particle mobility; a fifth operation mode for rearranging particles; and a sixth operation mode for determining particle information.

The processing circuit 1502p may be further coupled the base electrode 102 via the contact structure 108. The processing circuit 1502p may be configured to provide at least one electrical potential to the base electrode 102, e.g. based on the operation mode.

The processing circuit 1502p may be further configured to read out each sensor element of the sensor array 106, e.g. serially. For reading out a sensor element 106a of the sensor array 106, the processing circuit 1502p may be configured to sense (in other words, detect) an output signal of the sensor element 106a. The sensor element 106a may be configured to generate the output signal in response to a particle at least one of approaching to and adsorbed by the sensor element 106a. Alternatively or additionally, may be configured to provide the output signal in response to an input signal. Therefore, the processing circuit 1502p may be configured to generate the input signal and supply the input signal to a sensor element 106a of the sensor array 106.

The processing circuit 1502p may be configured to process the output signal. The processing circuit 1502p may be configured to determine a set of particle information by processing the output signal. The processing circuit 1502p may be configured to determine the presence of particles by processing the output signal. For example, the processing circuit 1502p may be configured to determine at least one of density, amount, and absorption rate (adsorbed particles per time) of the presence particles.

According to various embodiments, the set of particle information may include or be formed from at least one of (e.g. a combination of at least two, e.g. three or four) the following types of information: electrostatic charge information; particle size information; particle shape information; and/or particle material information.

The processing circuit 1502p may be configured to compare the set of (determined) particle information with a plurality of predefined particle characteristics each representing a particle sort so as to determine the presence of at least one particle sort. The set of particle information may be assigned to the at least one particle sort by comparing the set of particle information with a plurality of predefined particle characteristics each representing a particle sort.

The process controller 1502 may include a storage medium 1502m. The storage medium 1502m may be an electronic semiconductor storage medium 1502m, e.g. a read only memory (ROM) or a random access memory (RAM), e.g. a (M, S, D, F)-RAM or a (P, E, EE, Flash-EE)-ROM storage medium), a memory card, a Flash-memory, a universal serial bus (USB)-Stick, a solid state drive (SSD), a hard disc drive (HDD), a memory disc (MD), an exchangeable storage medium, a holographic storage medium, an optical storage medium, a compact-disc (CD), a digital-versatile-disc (DCV), a magneto-optical disk or another storage medium (also referred to as memory). The storage medium 1502m may include or be formed from a computer readable storage medium. Alternatively or additionally, the storage medium 1502m may include or be formed from a non-transitory storage medium.

The plurality of predefined particle characteristics may be stored in the storage medium 1502m, e.g. via a database. The processing circuit 1502p may be configured to read the plurality of predefined particle characteristics from the storage medium 1502m.

According to various embodiments, the process controller 1502 may be configured to carry out a method according to various embodiments, e.g. via the processing circuit 1502.

FIG. 15B illustrates a processing circuit 1502p for particle analysis in a schematic circuit diagram.

The processing circuit 1502p may include an acquiring unit 1512 configured to acquire the output signal (generated or modified by a sensor element 106a), e.g. by sensing the output signal. The acquiring unit 1512 may be configured to provide (e.g. digital) signal data representing the output signal. The acquiring unit 1512 may include a switchable interface coupled to each contact line the contact structure 108.

The signal data may optionally include temporal information of the output signal. For example, the signal data may include a time stamp representing an adoption event. Alternatively or additionally, the signal data may include a time stamp representing a desorption event.

The signal data may optionally include address data (also referred to as identification data). The processing circuit 1502p may further include an identification unit 1514 (also referred to as addressing unit 1514). The addressing unit 1514 may be configured to provide the address data. The address data may be assigned to the sensor element 106a of the sensor array 106, which generated or modified the output signal represented by the signal data.

The processing circuit 1502p may optionally include a memory 1516. The memory 1516 may be configured to store a size-sensing characteristic for each sensor element of the sensor array 106. The processing circuit 1502p may be configured to determine particle information using the size-sensing characteristic stored in the first memory. For example, the processing circuit 1502p may correlate the size-sensing characteristic with the signal data representing a particle size. Illustratively, the processing circuit 1502p may refine the particle size information obtained by using the size-sensing characteristic. For example, the size-sensing characteristic may include a range of particle size for which the respective sensor element 106a provides an output signal (e.g. when a particle contacts at least two electrodes of the sensor element 106a).

The size-sensing characteristic of a sensor element 106 of the sensor array 106 may include or be formed from at least one of the following characteristic: at least one first particle size range defined by the sensor element (e.g. by its topography, electrode distance and/or recess depth), and a particle size range defined by a filter layer covering the sensor element 106a (if present). For example, the at least one first particle size range and the second particle range may overlap each other. The overlap may obtain information about the particle size of a particle, which is detected.

The processing circuit 1502p may optionally include a base electrode controller unit 1518. The base electrode controller unit 1518 may be coupled to the base electrode via a base electrode line 108m of the contact structure 108. The base electrode controller unit 1518 may be configured to control the at least one electrical potential provided to the base electrode 102. The at least one electrical potential provided to the base electrode 102 may be dependent on the operation mode. For example, the base electrode controller unit 1518 may be configured to provide the attraction potential in a sensing operation mode. Alternatively or additionally, the base electrode controller unit 1518 may be configured to provide the repulsion potential in a cleaning operation mode.

The processing circuit 1502p may optionally include a repulsion electrode controller unit 1528. The repulsion electrode controller unit 1528 may be coupled to the repulsion electrode via a repulsion electrode line 118m of the contact structure 108. The repulsion electrode controller unit 1528 may be configured to control an electrical potential provided to the repulsion electrode. The electrical potential provided to the repulsion electrode may be dependent on the operation mode. For example, the repulsion electrode controller unit 1528 may be configured to provide at least one of the compensation potential and a reference potential in a sensing operation mode. Alternatively or additionally, the repulsion electrode controller unit 1528 may be configured to provide the repulsion potential in a cleaning operation mode.

The processing circuit 1502p may be configured to detect an adsorption event (representing a particle adsorbed at the sensor element 106a). Alternatively or additionally, the processing circuit 1502p may be configured to detect a desorption event (representing a particle desorbed from the sensor element 106a). The processing circuit 1502p may be configured to determine a strength of the repulsing potential at the desorption event (or a respective electric field strength).

The signal data may optionally include at least one of adsorption event data and desorption event data. The desorption event data may include information representing the strength of the repulsing potential (or a respective electric field strength) at the desorption event. Alternatively or additionally, the desorption event data may include information representing the rate of particle desorption. Optionally, the desorption event data may include time information of the desorption event (e.g. a time stamp). The adsorption event data may include information representing the strength of the attraction potential (or a respective electric field strength) at the adsorption event. Alternatively or additionally, the adsorption event data may include information representing the rate of particle adsorption. Optionally, the adsorption event data may include time information of the adsorption event (e.g. a time stamp).

The processing circuit 1502p may be configured to determine electrostatic charge information, e.g. by sensing at least one of the desorption event and the adsorption event (e.g. for an identified sensor). The electrostatic charge information may include information about an inherent charge of the particle detected. At least one of the desorption event and the adsorption event may be sensed in dependency on at least one of a magnitude and a polarity of the electrical potential (or a respective electric field strength), e.g. provided to the base electrode 102 (e.g. a desorption event representing an adhesion strength). The electrostatic charge information may represent an adhesion strength of the particle to the sensor array. The signal data may optionally include adhesion strength information. The adhesion strength information may represent an adhesion strength of the particle to the sensor array.

According to various embodiments, the processing circuit 1502p may be configured to determine at least one of particle size information, particle shape information and electrostatic charge information by correlating electrical signals generated or modified by adjacent sensor elements. Illustratively, a particle may overlap more than one sensor element 106a of the sensor array 106. This information may be used to obtain or refine at least one of particle size information and particle shape information. Alternatively or additionally, a particle may move between more than one sensor elements 106a of the sensor array 106. This information may be used to obtain or refine electrostatic charge information. A particle movement may be induced by at least one of mechanical, acoustical, or electrical vibrations.

The signal data may optionally include particle material information. The processing circuit 1502p may be configured to determine the particle material information. The particle material information may represent at least one of a chemical composition and electric properties (e.g. at least one of resistance, electrical conductivity and dielectric permittivity) of a particle. I The particle material information may be obtained by sensing a change in the electrical impedance of a sensor element 106 response, for example, to at least one of a particle adsorption event and a particle desorption event. Alternatively or additionally, the particle material information may be obtained by sensing a change in the electrical impedance of a sensor element 106 response to a particle approaching event. Optionally, the particle material information may be obtained by sensing spectral information representing the particle.

The processing circuit 1502 may be configured to assign the set of particle information to at least one particle sort by comparing the set of particle information with the plurality of predefined particle characteristics. Illustratively each particle may have a fingerprint represented by the predefined particle characteristics. The processing circuit 1502p may be configured to identify a fingerprint representing the obtained particle information best. The predefined particle characteristics may optionally include at least one of seasonal information and regional information for each particle sort (illustratively, information when and where a particle sort occurs).

The processing circuit 1502p may optionally include a tagging unit 1520 (configured for at least one of chronological tagging and geological tagging). The tagging unit 1520 may be configured to assign a time stamp (temporal coordinates) to the at least one electrical signal, as described before. The processing circuit 1502p may be configured to compare the time stamp to the seasonal information so as to determine the presence of at least one particle sort (e.g. for assigning the set of particle information to at least one particle sort).

Alternatively or additionally, the tagging unit 1520 may be configured to assign a location stamp (spatial coordinates) to the at least one electrical signal. The location stamp may represent a location of the sensor arrangement during operating. Therefore, the processing circuit 1502p may be configured to determine the location of the sensor arrangement during operating. The processing circuit 1502p may be configured to compare the location stamp to regional information so as to determine the presence of at least one particle sort (e.g. for assigning the set of particle information to at least one particle sort).

Optionally, the processing circuit 1502p may be configured to determine a particle density, e.g. by sensing a rate of at least one of a particle adsorption event and a particle desorption event.

According to various embodiments, the processing circuit 1502p may be configured for array signal processing, e.g. in order to correlate electrical signals generated or modified by more than one sensor element 106a of the sensor array 106, e.g. by adjacent sensor elements 106a of the sensor array 106.

Figure 16:
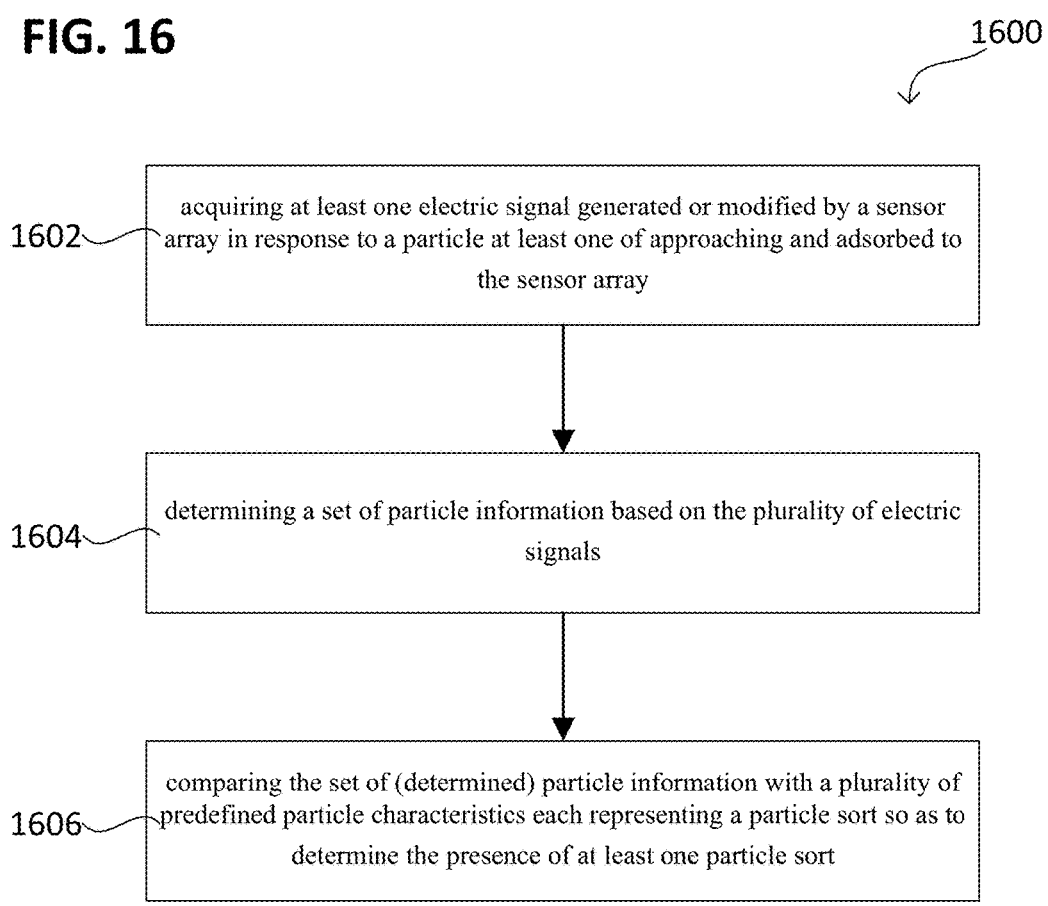
FIG. 16 illustrates a method according to various embodiments.

FIG. 16 illustrates a method 1600 for particle analysis in a schematic flow diagram.

The method may include in 1602: acquiring at least one electrical signal generated or modified by a sensor array in response to a particle at least one of approaching and adsorbed to the sensor array.

The method may further include in 1604: determining a set of particle information based on the plurality of electrical signals. The set of particle information may include or be formed from at least one of (e.g. a combination of at least two, e.g. three, or four) the following types of information: electrostatic charge information; particle size information; particle shape information; and/or particle material information.

The method may further include in 1606: comparing the set of (determined) particle information with a plurality of predefined particle characteristics each representing a particle sort so as to determine the presence of at least one particle sort.

Figure 17A:
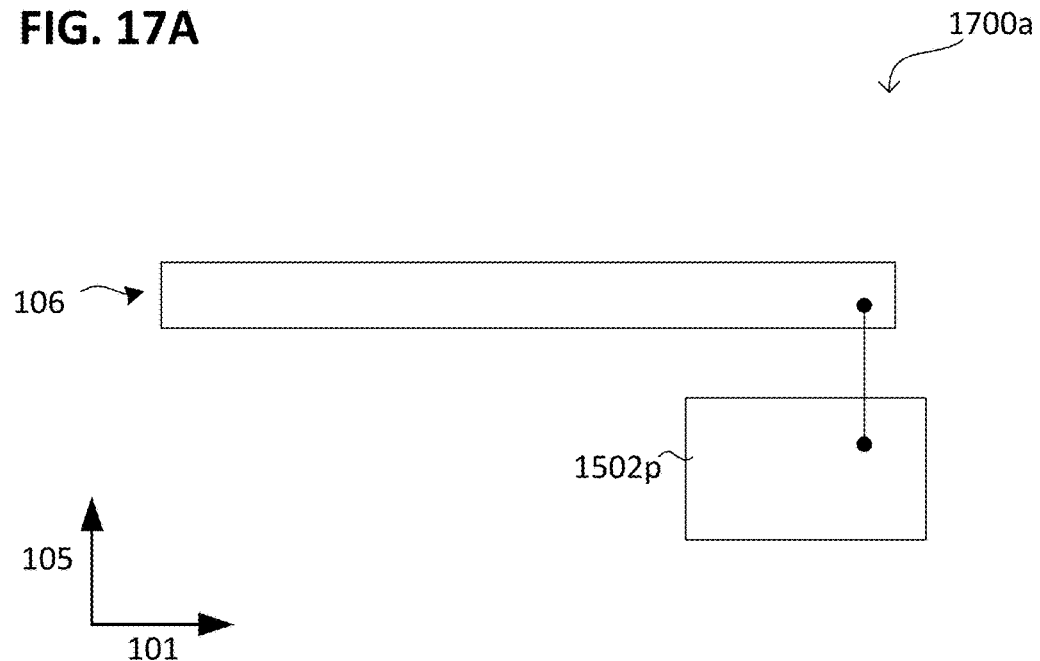
FIG. 17A shows a sensor arrangement according to various embodiments.

FIG. 17A illustrates a sensor arrangement 1700a for particle analysis in a schematic side view or first cross sectional view (e.g. parallel to direction 103).

The sensor arrangement 1700 may include a sensor array 106. The sensor array may be configured to generate or modify at least one electrical signal in response to a particle at least one of approaching and adsorbed to the sensor array 106. The at least one electrical signal may include or be formed from a plurality of electrical signals.

The sensor arrangement 1700 may further include a processing circuit 1502p. The processing circuit 1502p may be configured to sense the at least one electrical signal. The processing circuit 1502p may be further configured to determine a set of particle information based on the at least one electrical signal. The set of particle information may include or be formed from at least one of (e.g. a combination of at least two, e.g. three or four) the following types of information: electrostatic charge information; particle size information; particle shape information; and/or particle material information.

The processing circuit 1502p may be further configured to compare the set of (determined) particle information with a plurality of predefined particle characteristics each representing a particle sort so as to determine the presence of at least one particle sort. For example, the processing circuit 1502p may be configured to assign the set of particle information to at least one particle sort by comparing the set of particle information with a plurality of predefined particle characteristics each representing a particle sort. The sensor array 106 may be configured similar to any of the sensor arrays described herein.

Figure 17B:
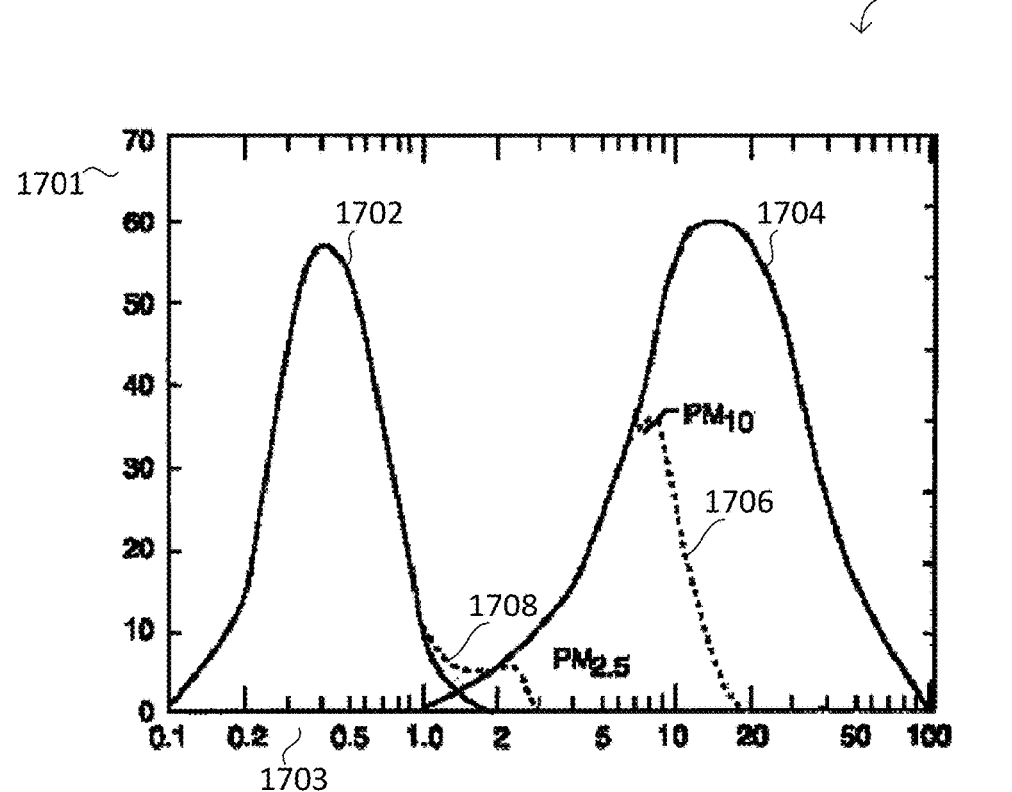
FIG. 17B shows a diagram according to various embodiments.

FIG. 17B illustrates a particle characteristic 1700b in a schematic diagram. The diagram represents a particle rate 1701 over a particle size 1703 (e.g. in micrometer). The particle rate 1701 may represent a rate of a particle recognition, e.g. by at least one of a particle desorption (e.g. event), a particle adsorption (e.g. event) and a particle approaching (e.g. event). The particle rate 1701 may optionally represent or be converted into a density of the particles, e.g. number of particles per volume.

A first particle characteristic 1702 of a first particle sort may represent a particle size distribution of the first particle sort. A second particle characteristic 1704 of a second particle sort may represent a particle size distribution of the second particle sort. A third particle characteristic 1706 of a third particle sort may represent a particle size distribution of the third particle sort. A fourth particle characteristic 1706 of a fourth particle sort may represent a particle size distribution of the fourth particle sort. Each particle characteristic 1702, 1704, 1706, 1708 may be characterized by at least one value of: a mean value, a maximum value, a standard deviation value and a full width at half-maximum (FWHM) value. The values of the particle characteristic 1702, 1704, 1706, 1708 may enable to distinguish between the particle sorts of particles detected, e.g. simultaneously. For example, a pollen size distribution 1704 may be in the range from about 10 µm to about 100 µm. The pollen size distribution 1704 may have a greater mean value than a fine dust distribution 1706. Further, a pollen size distribution 1706 of a certain pollen sort (e.g. emitted by a specific plant) may be narrower and can thus be separated from at least one of ambient fine dust of other pollen sorts.

Figure 18:
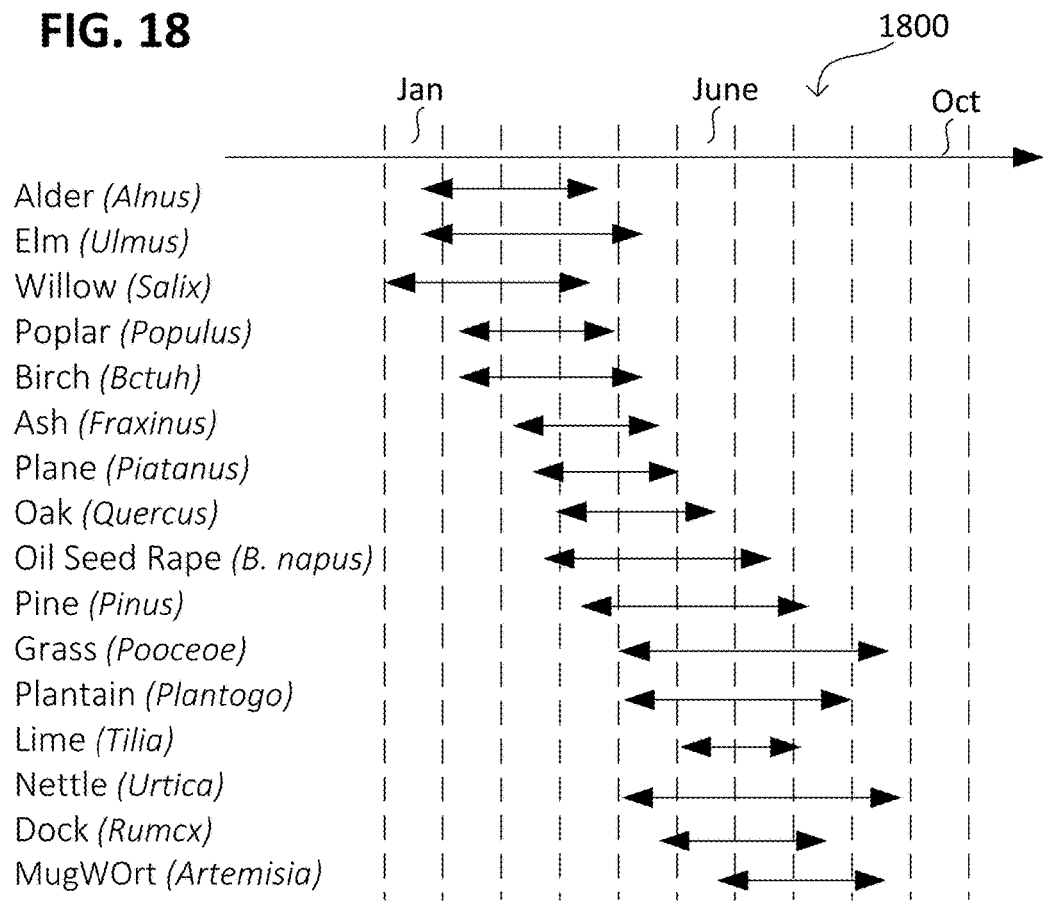
FIG. 18 to FIG. 20 respectively show a particle characteristic according to various embodiments.

FIG. 18 illustrates a particle characteristic 1800 in a schematic diagram. The diagram shows seasonal information for a selection of pollen particle sorts. The arrows may be understood as range representing the temporal occurrence of the particle sort.

Figure 19:
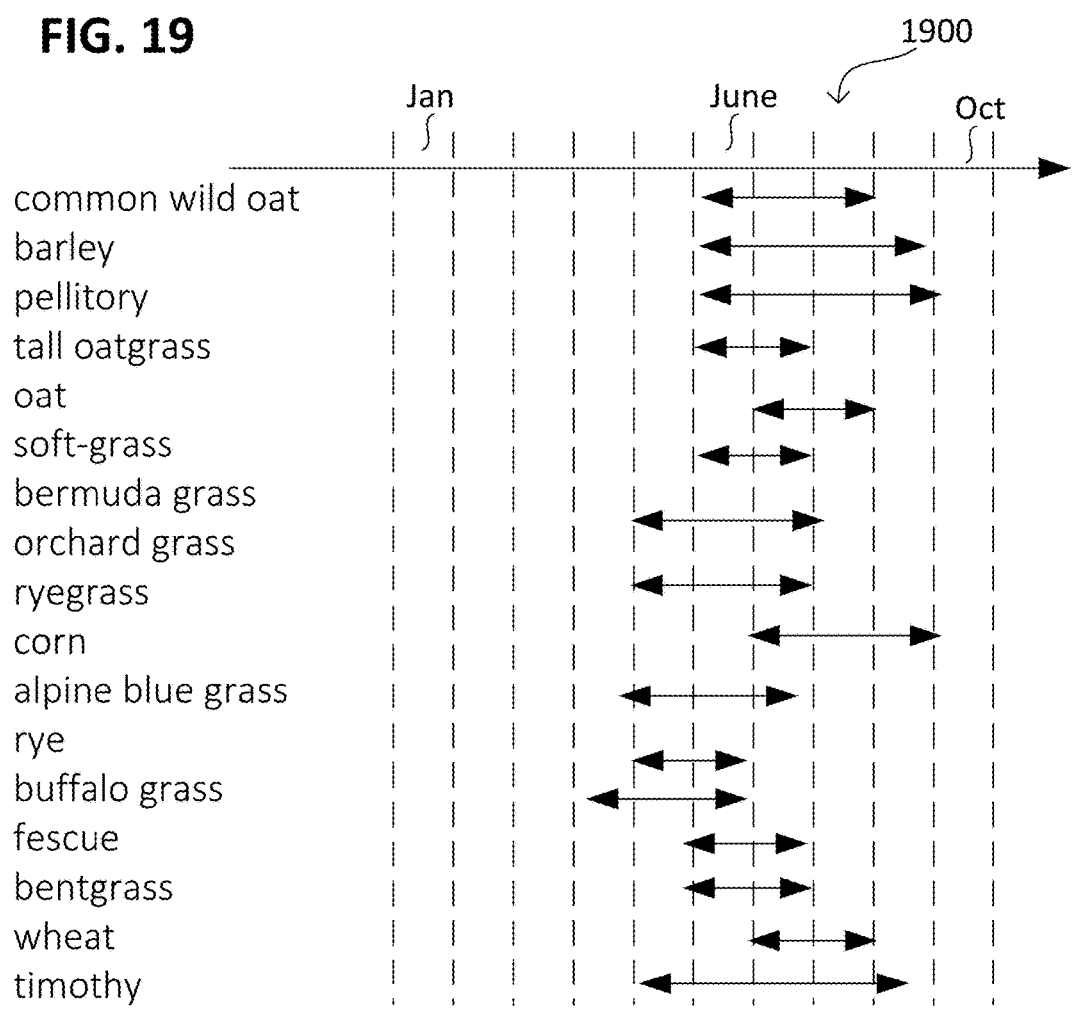

FIG. 19 illustrates a particle characteristic 1900 in a schematic diagram. The diagram shows seasonal information for a selection of pollen particle sorts. The arrows may be understood as range representing the temporal occurrence of the particle sort.

Figure 20:
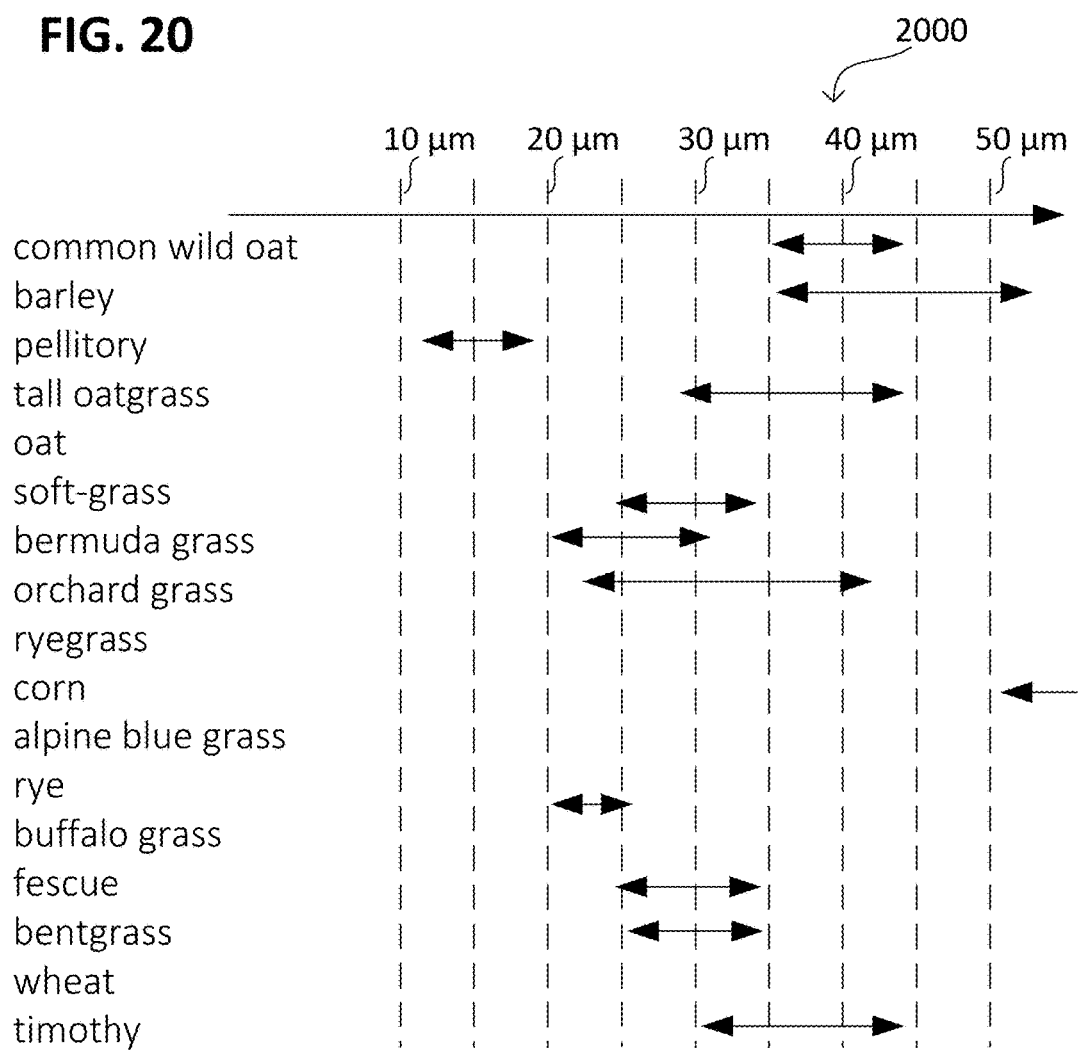

FIG. 20 illustrates a particle characteristic 2000 in a schematic diagram. The diagram shows size information for a selection of pollen particle sorts. The arrows may be understood as range representing a FWHM of the particle size.

Figure 21:
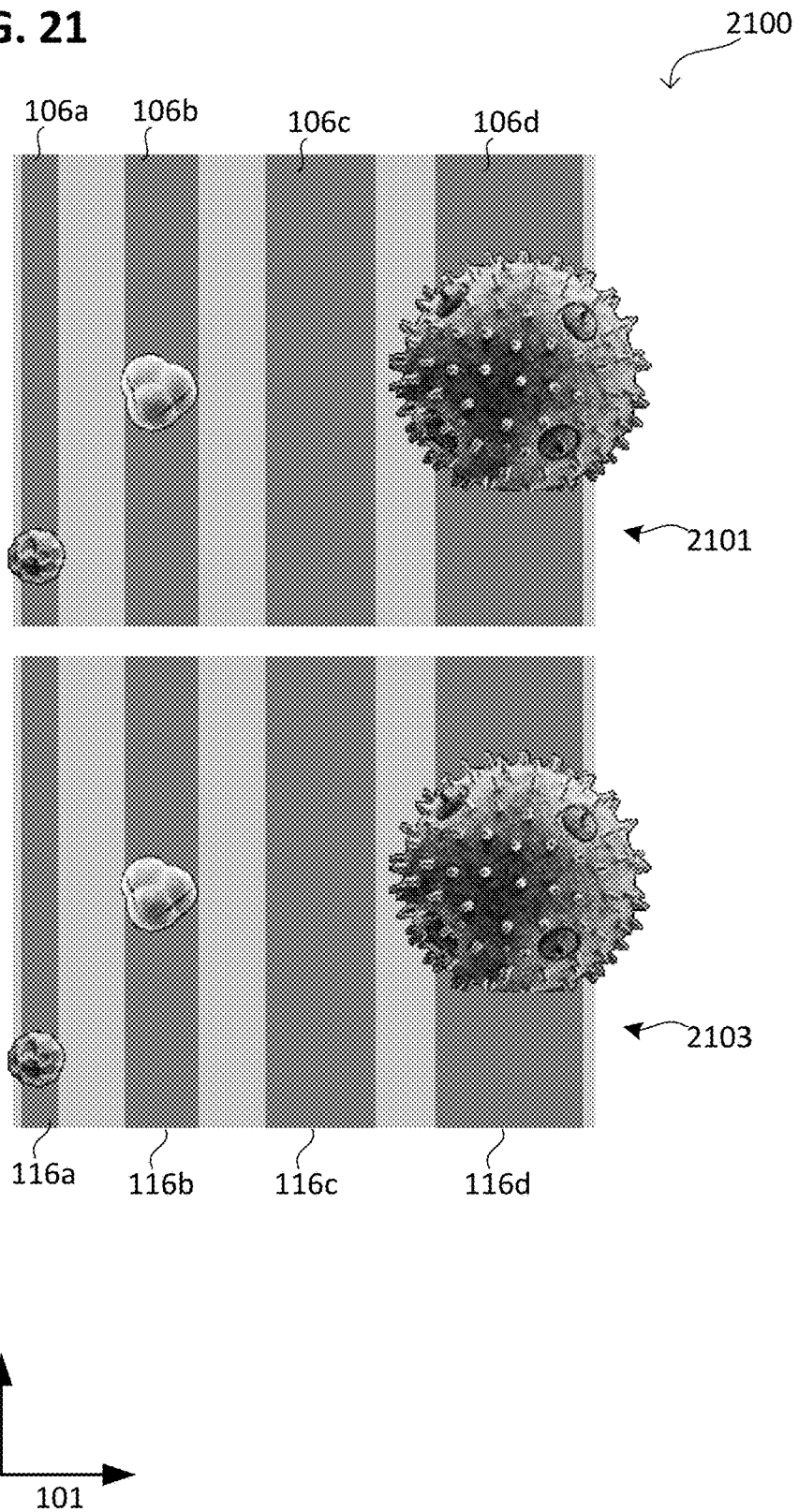

FIG. 21 illustrates a sensor array 2100 in a schematic top view or cross sectional view (e.g. parallel to direction 105). The sensor array 2100 may include a first row 2101 of a first plurality of sensor elements 106a, 106b, 106c, 106d and a second row 2103 of a second plurality of sensor elements 116a, 116b, 116c, 116d. The sensor elements of the sensor array 2100 may be at least one of a photoelectrical sensors 304 and an electrochemical fluid sensors 306. The different sensor areas (illustratively, pixel sizes) may facilitate a discrimination of particle sizes.

Figure 22:
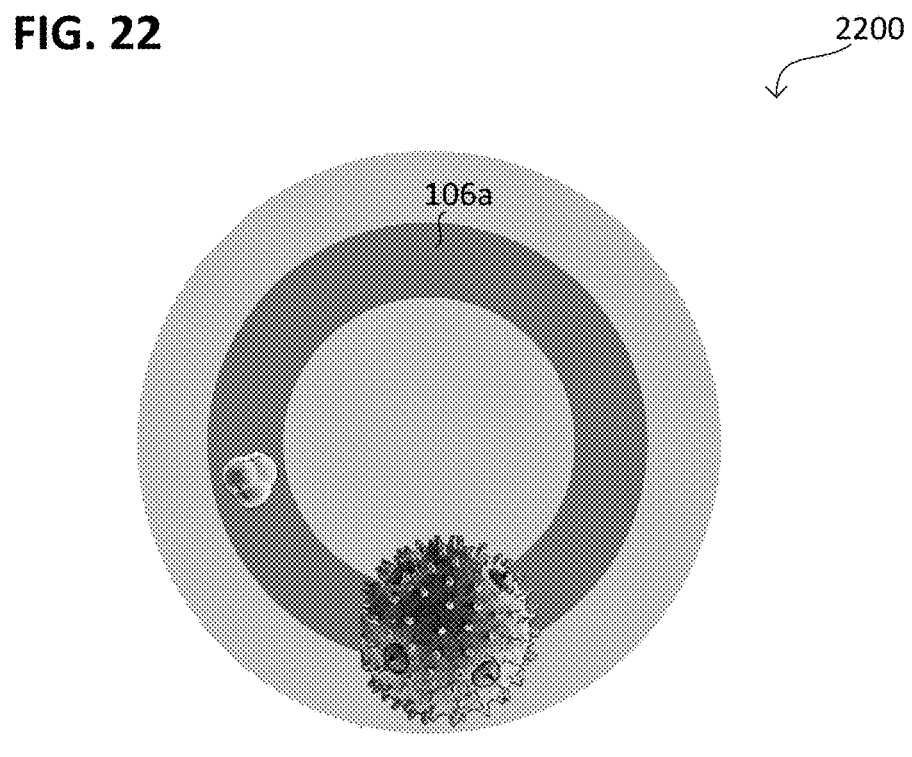

FIG. 22 illustrates a sensor array 2200 in a schematic top view or cross sectional view (e.g. parallel to direction 105). The sensor array 2200 may include a first sensor elements 106a and a second sensor elements 106b. The sensor elements of the sensor array 2200 may include a ring shaped sensing area. At least two sensor elements of the sensor array 2200 may differ in at least one of their extension (e.g. diameter) and their sensing area (e.g. spatially averaged). The sensor elements of the sensor array 2200 may be at least one of a photoelectrical sensors and an electrochemical fluid sensors. The radial distribution of the sensing area (distribution function) around a central pixel may facilitate to determine the particle size.

FIG. 23 illustrates a sensor array 2300 in a schematic top view or cross sectional view (e.g. parallel to direction 105) similar to the sensor array 2100. The sensor elements of the sensor array 2300 may be electrical impedance sensor.

FIG. 24 illustrates a sensor array 2400 in a schematic top view or cross sectional view (e.g. parallel to direction 105) similar to the sensor array 2200. The sensor elements of the sensor array 2400 may be electrical impedance sensor.

Figure 25:
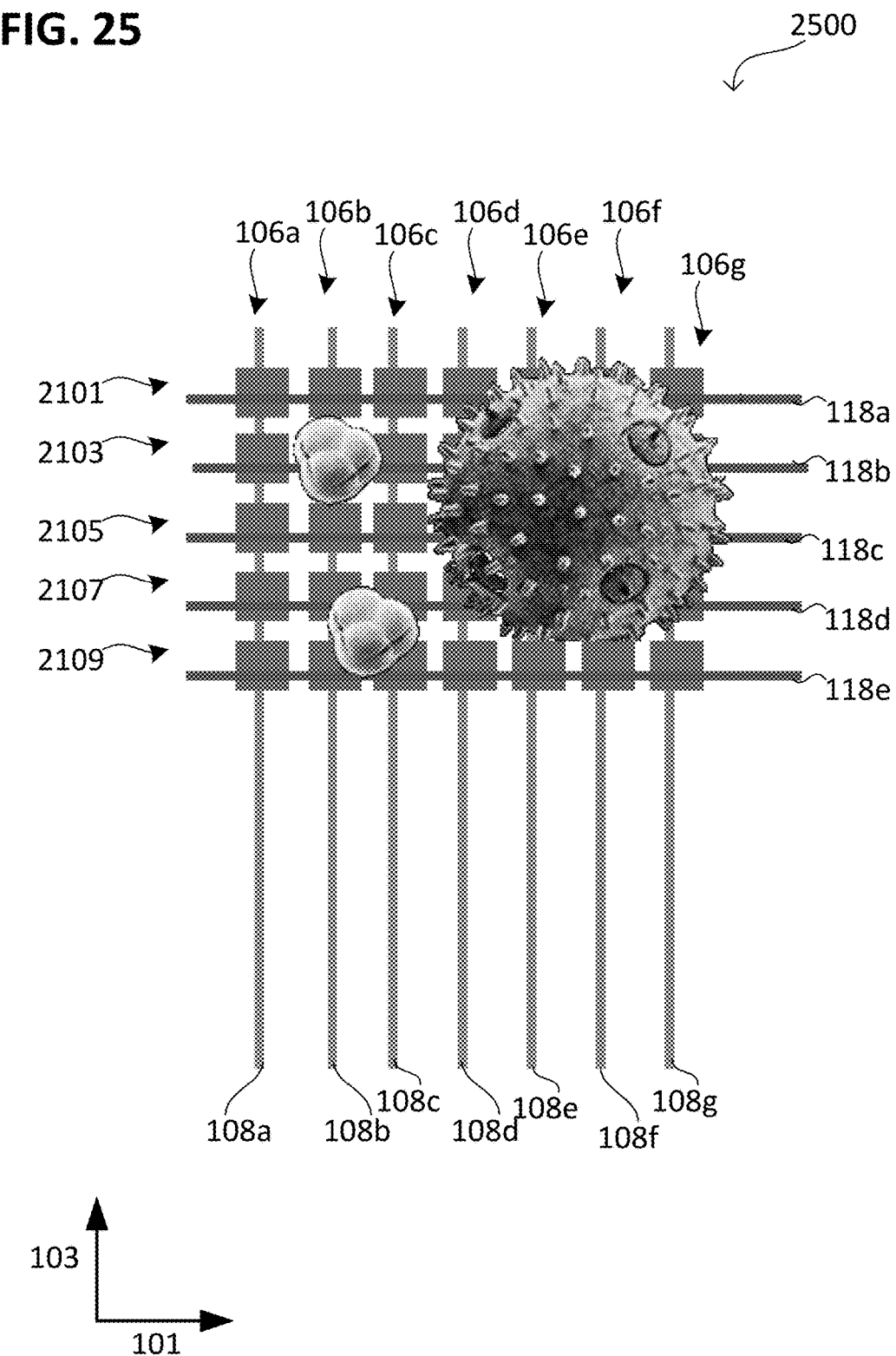

FIG. 25 illustrates a sensor array 2500 in a schematic top view or cross sectional view (e.g. parallel to direction 105) similar to the sensor arrays described before. The sensor array 2500 may include or be formed from an optical matrix (e.g. a charge-coupled device sensor array). In other words, each sensor elements of the sensor array 2500 may include a (e.g. charge-coupled device based) photoelectrical sensor 304. Alternatively, each sensor elements of the sensor array 2500 may include an electrochemical fluid sensor 306.

By way of example, the sensor elements of the sensor array 2500 may include or be formed from at least one of a pn-diode (operated as solar cell), a photo diode and a photo resistance (also referred to as photoresistor).

The sensor array 2500 may include a plurality of rows 2101, 2103, 2105, 2107, 2109 each including a plurality of sensor elements 106a, 106b, 106c, 106d, 106e, 106f, 106g.

The sensor elements of a first row of the plurality of rows 2101, 2103, 2105, 2107, 2109 may be electrically coupled with each other via first contact line 118a of the second plurality of contact lines 118a, 118b, 118c, 118d, 118e. In analogy, the sensor elements of the other rows of the plurality of rows 2101, 2103, 2105, 2107, 2109 may be electrically coupled with each other via a respective contact line of the second plurality of contact lines 118a, 118b, 118c, 118d, 118e.

The first sensor element 106a of each row of the plurality of rows 2101, 2103, 2105, 2107, 2109 may be electrically coupled with each other via a first contact line 118a of the first plurality of contact lines 108a, 108b, 108c, 108d, 108e, 108f, 108g. In analogy, the respective sensor element of the other rows of the plurality of rows 2101, 2103, 2105, 2107, 2109 may be electrically coupled with each other via the respective contact line of the first plurality of contact lines 108a, 108b, 108c, 108d, 108e, 108f, 108g.

Figure 26:
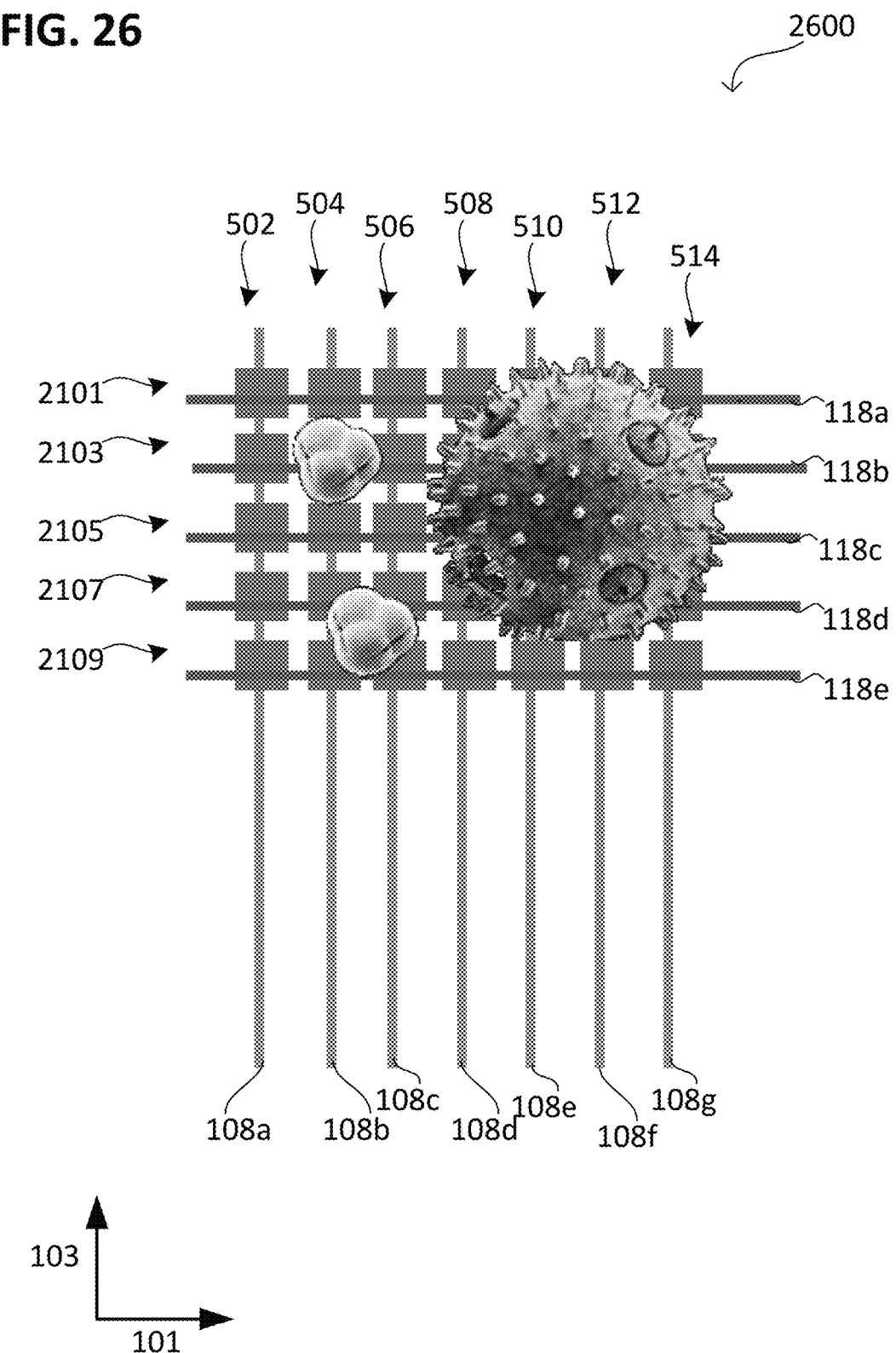

FIG. 26 illustrates a sensor array 2600 in a schematic top view or cross sectional view (e.g. parallel to direction 105) similar to the sensor arrays described before. The sensor array 2600 may include or be formed from a capacitive matrix. In other words, each sensor elements of the sensor array 2600 may include an electrical impedance sensor 302.

The sensor array 2600 may include a plurality of rows 2101, 2103, 2105, 2107, 2109 each including a plurality of electrodes 502, 504, 506, 508, 510, 512, 514. By way of example, between adjacent electrodes of the plurality of electrodes 502, 504, 506, 508, 510, 512, 514 a sensor element of the sensor array 2600 may be formed (see for example, FIG. 7A). In other words, each electrode of the plurality of electrodes 502, 504, 506, 508, 510, 512, 514 may be assigned to more than one sensor element of the sensor array 2600, e.g. to two or more than two sensor elements of the sensor array 2600, e.g. to three or more than three sensor elements of the sensor array 2600, e.g. to four or more than four sensor elements of the sensor array 2600.

The electrodes of a first row of the plurality of rows 2101, 2103, 2105, 2107, 2109 may be electrically coupled with each other via first contact line 118a of the second plurality of contact lines 118a, 118b, 118c, 118d, 118e. In analogy, the electrodes of the other rows of the plurality of rows 2101, 2103, 2105, 2107, 2109 may be electrically coupled with each other via a respective contact line of the second plurality of contact lines 118a, 118b, 118c, 118d, 118e.

The first electrode 502 of each row of the plurality of rows 2101, 2103, 2105, 2107, 2109 may be electrically coupled with each other via a first contact line 118a of the first plurality of contact lines 108a, 108b, 108c, 108d, 108e, 108f, 108g. In analogy, the respective electrodes of the other rows of the plurality of rows 2101, 2103, 2105, 2107, 2109 may be electrically coupled with each other via the respective contact line of the first plurality of contact lines 108a, 108b, 108c, 108d, 108e, 108f, 108g.

Figure 27:
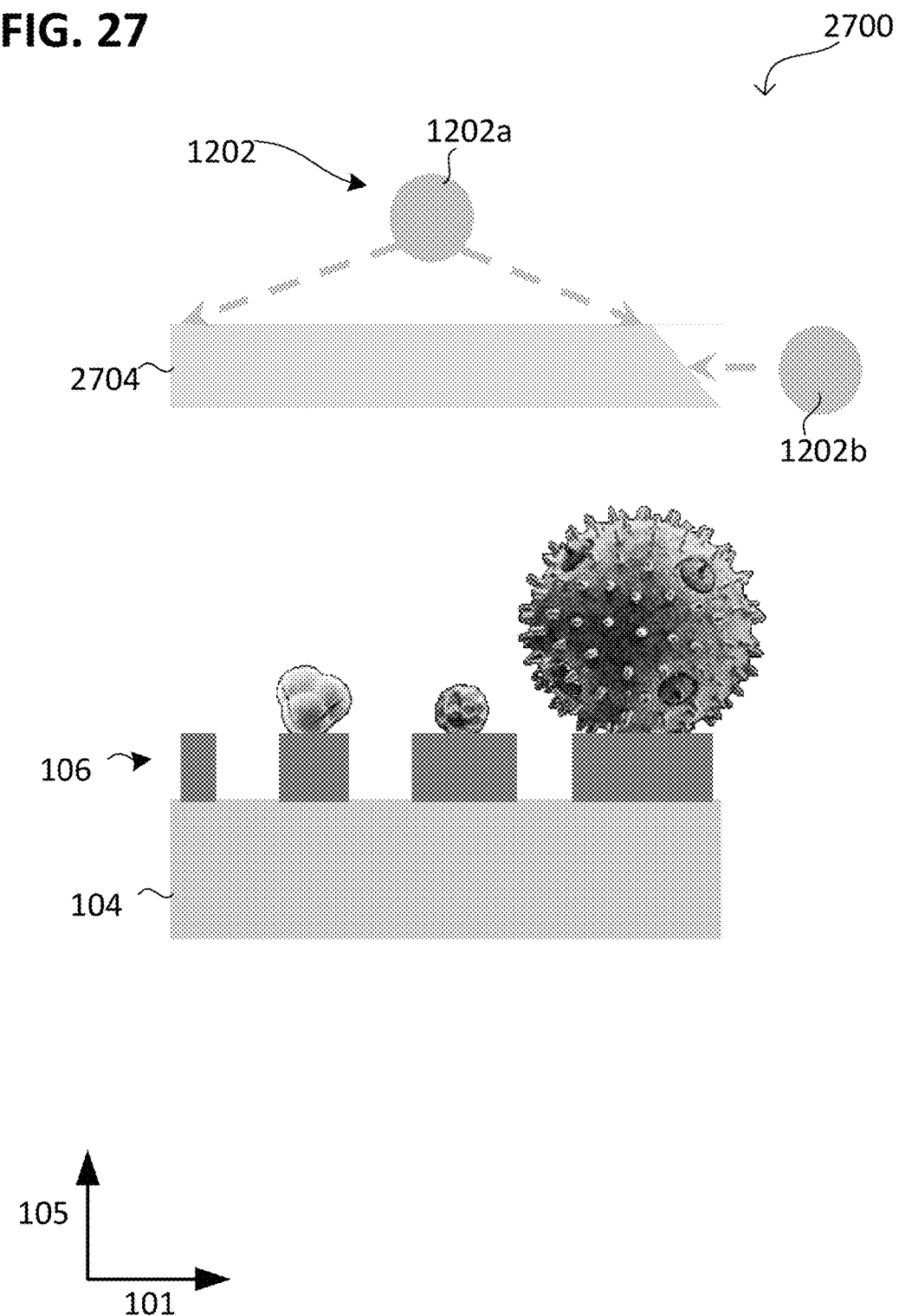
FIG. 27 shows a sensor arrangement according to various embodiments.

FIG. 27 illustrates a sensor arrangement 2700a for particle analysis in a schematic side view or first cross sectional view (e.g. parallel to direction 103).

The sensor arrangement 2700a may include an optical diffusor 2704 disposed over the sensor array 106. The optical diffusor 2704 may homogenize incoming electromagnetic radiation. The optical diffusor 2704 may be configured to spread out or scatter electromagnetic radiation (e.g. light). The optical diffusor 2704 may include or be formed from at least one of a translucent material, a ground glass diffuser, a Teflon diffuser, a holographic diffuser, an opal glass diffuser, and an greyed glass diffuser.

The sensor arrangement 2700a may further include at least one of a first electromagnetic radiation source 1202a and a second electromagnetic radiation source 1202a. The first electromagnetic radiation source 1202a may be configured to emit electromagnetic radiation towards the sensor array 106, e.g. through the optical diffusor 2704. The second electromagnetic radiation source 1202b may be configured to emit electromagnetic radiation into a lateral direction (e.g. passing the sensor array 106) towards the optical diffusor 2704 (e.g. for indirect illumination).

At least one of the first electromagnetic radiation source 1202a and the second electromagnetic radiation source 1202a may be configured to emit at least one of the following electromagnetic radiation: monochromatic light (e.g. LED light); polychromatic light; continuous visible light; infrared light and ultraviolet light. By way of example, at least one of the first electromagnetic radiation source 1202a and the second electromagnetic radiation source 1202a may include or be formed from a solid state electromagnetic radiation source, e.g. a light emitting diode (LED), polymer light-emitting diode (PLED) or an organic light emitting diode (OLED).

Using monochromatic light may enable to detect a particle size based on a degree of attenuation. Using polychromatic light (e.g. visible, infrared, ultraviolet) may enable to detect the particle sort, e.g. based on spectroscopy, e.g. transmission spectroscopy.

The sensor arrangement 2700a may include or be formed from photoelectrical sensor 304, such as integral photoelectrical sensors 304 and spectroscopic integral photoelectrical sensors 304. Using an integral photoelectrical sensor 304 may enable to detect a particle size based on a degree of attenuation. Using a spectroscopic photoelectrical sensor 304 may enable to detect the particle sort based on a spectroscopy (e.g. using a Fabry-Perot filter, spectral tunable photodiode and the like). For example, any of the herein described photoelectrical sensor 304 may be an energy dispersive photoelectrical sensor 304.

Figure 28:
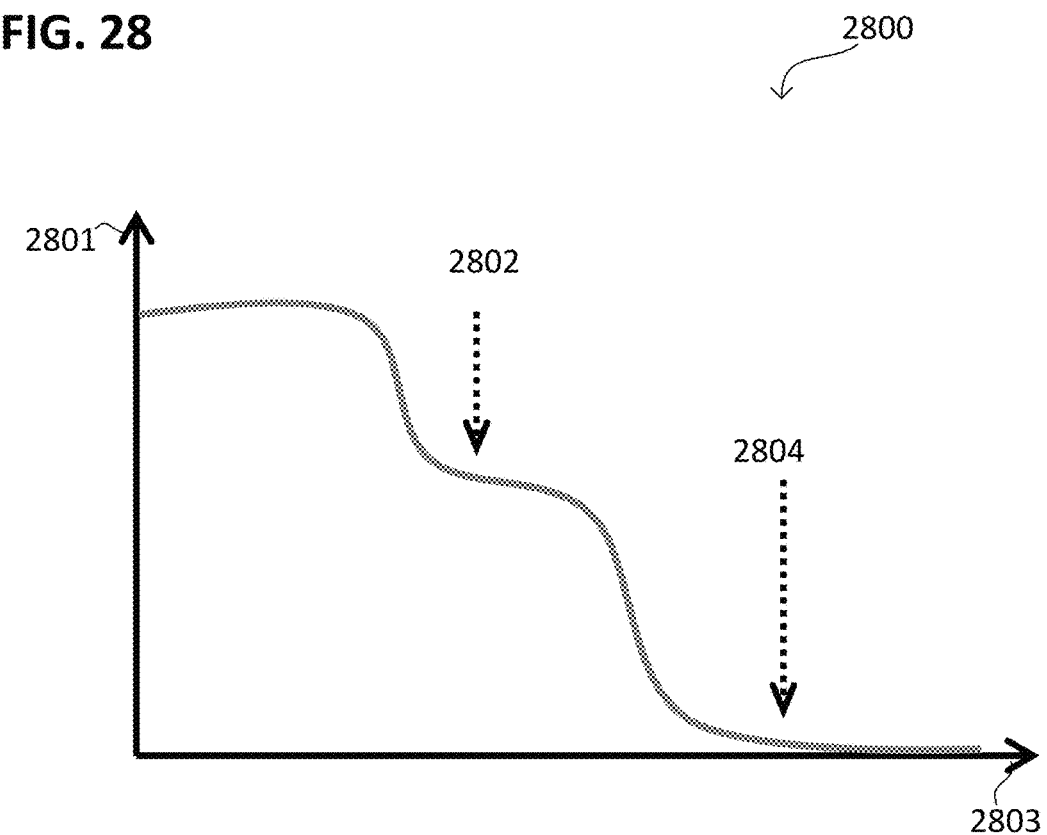
FIG. 28 shows a diagram according to various embodiments.

FIG. 28 illustrates a method according to various embodiments, in a schematic diagram 2800. The diagram may show a particle coverage 2801 (e.g. in percentage) over an electric field strength 1803 (in arbitrary units).

A first desorption event 2802 (e.g. a collective desorption event) may be characterized a first drop in particle coverage 2801 (e.g. detected by the sensor array 106). The first desorption event 2802 may represent a first particle type. The electric field strength of the first desorption event 2802 may represent at least one of the first particle type: a first charge and a first size.

A second desorption event 2804 (e.g. a collective desorption event) may be characterized a second drop in particle coverage 2801 (e.g. detected by the sensor array 106). The second desorption event 2804 may represent a second particle type. The electric field strength of the second desorption event 2804 may represent at least one of the second particle type: a second charge and a second size.

Illustratively, the particle coverage 2801 (e.g. fraction of surface covered by particles) may depend on the applied electrical repulsion field. The particle charge distribution detected from the respective desorption event 2802, 2804 may enable a discrimination of particle by at least one of charge and size. Further, a polarity of the repulsion field may enable a discrimination of particle type. For example, pollen may have at least one of an inherent charge and an inherent polarity.

Figure 29:
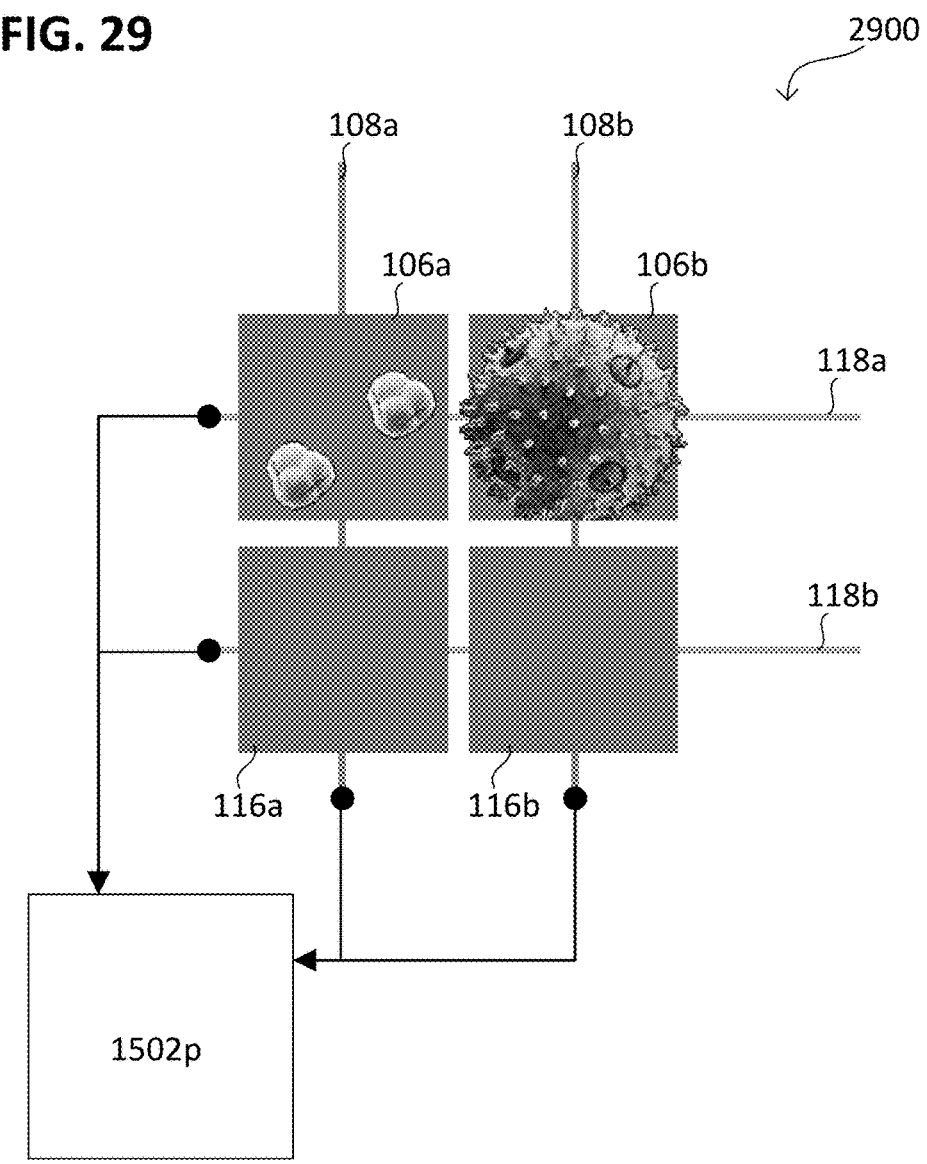
FIG. 29 shows a sensor arrangement according to various embodiments.

FIG. 29 illustrates a sensor array 2900 in a schematic top view or cross sectional view (e.g. parallel to direction 105) similar to the sensor arrays described before. The sensor array 2900 may include or be formed from a plurality of sensor elements 106a, 106b, 116a, 116d. The sensor elements 106a, 106b, 116a, 116d of the sensor array 2900 may be configured to detect a particle coverage, exemplarily illustrated by different particle types. Smaller particles generate a higher amount (or respective rate) of at least one of desorption events and adsorption events per particle coverage. Correlating the rate of events (e.g. at least one of desorption events and adsorption events) with the particle coverage may enable to refine the particle size information.

In the following a first operation sequence is described for an exemplary photoelectrical sensor array 2900, e.g. a photodiode sensor array 2900. The sensor elements of the photoelectrical sensor array 2900 may generate an output signal, e.g. an electrical voltage, representing a fraction of coverage. The processing circuit 1502p may be configured to sense the output signal for each sensor element of the photoelectrical sensor array 2900. By comparing the output signal between the sensor elements of the photoelectrical sensor array 2900, the particle coverage may be determined, e.g. by calculation (e.g., by comparison to at least one reference measurement provided by at least one of a previously made measurement and a measurement using a reference section). For example, the particle coverage may be determined by comparing electrical signals generated or modified by a sensing section of the sensor array 2900 with electrical signals generated or modified by a reference section of the sensor array 2900, e.g., for signal background subtraction (e.g., noise subtraction).

In other words, the comparison of the output signals may provide an indicator representing how much shading is present, and depending on the sensing area size of the sensor elements of the photoelectrical sensor array 2900, a particle coverage may be determined. Based on the particle coverage, a particle size information may be determined. Alternatively or additionally, the output signal may be compared to a predefined criterion. The sensor element of the photoelectrical sensor array 2900 may be determined as "covered" when the output signal fulfills the predefined criterion.

In the following a second operation sequence is described for an exemplary photoelectrical sensor array 2900, e.g. a photodiode sensor array 2900. By determining whether or not adjacent sensor elements of the photoelectrical sensor array 2900 are "covered" and/or by which amount they are covered, particle size information may be revealed, e.g. by calculation. For an ordinary particle density (e.g. per volume), particles may be adsorbed at sensor elements of the photoelectrical sensor array 2900 distant to each other. This result may be obtained by using the Poisson distribution, as exemplarily given in the following: For a sensing area per sensor element of 1 µm and a sensor array area of about 2 Millimeter (mm), the sensor array 2900 may include about 4 million sensor elements (e.g. photodiodes). By adsorbing about 1000 particles, the probability of having particles adsorbed to adjacent sensor elements may be about $\frac{1}{4000}$. If an agglomerate of more than one particle is adsorbed, they may be distinguished by dynamic measurements. For example, the particles adsorbed to the sensor array 2900 may be rearranged by activating a movement of the particles. The activating a movement may use at least one of mechanical vibrations, acoustical vibrations and electrical vibrations. This may enable to refine the at least one of particle size information and particle rate information.

In the following a third operation sequence is described for an exemplary photoelectrical sensor array 2900, e.g. a photodiode sensor array 2900. The sensor elements of the sensor array 2900 (e.g. at least two sensor elements) may differ in their strength of particle attraction, e.g. by differing in at least one of: static or dynamic charging of the sensor elements, surface induced adhesion; surface induced hydrophobia and surface induced hydrophilicity. By way of example, the anti-adhesion layer may include a gradient in its adhesion strength. In other words, the anti-adhesion layer may include or be formed from two region differing in their adhesion strength. For example, the sensor array 2900 may be covered by a hydrophobic anti-adhesion layer having a spatial gradient in hydrophobia. Alternatively or additionally, the sensor array 2900 may be covered by a hydrophilic anti-adhesion layer having a spatial gradient in hydrophilicity.

In the following a third operation sequence is described for an exemplary photoelectrical sensor array 2900, e.g. a photodiode sensor array 2900. The sensor elements of the sensor array 2900 may be configured to sense spectroscopic information of the particles. The spectroscopic information of the particles may be used to refine the particle type information. Illustratively, the color of the particles may be used to determine the particle type. For example, pollen may include spectroscopic information beyond the visible range of light, which may be obtained.

Further, various embodiments will be described in the following.

According to various embodiments, a sensor arrangement for particle analysis may include: a base electrode configured to generate an electrical field for particle attraction; a support layer disposed over the base electrode; a sensor array disposed over the support layer and including or formed from a plurality of sensor elements, wherein each sensor element of the plurality of sensor elements is configured to generate or modify an electrical signal in response to a particle at least one of (e.g. proximate) adsorbed to and approaching the sensor element; and an electrical contact structure may include or be formed from a plurality of contact lines, wherein each contact line of the plurality of contact lines is electrically connected to a respective sensor element of the plurality of sensor elements, such that each sensor element of the plurality of sensor elements is addressable via the contact structure. According to various embodiments, the at least one of the plurality of sensor elements may be an electrical impedance sensor configured to change its electrical impedance in response to a particle at least one of adsorbed to and approaching the electrical impedance sensor. According to various embodiments, the at least one of the plurality of sensor elements may be a photoelectrical sensor is configured to modify an electric charge movement capability in response to receiving electromagnetic radiation energy, such that an electrical output of the photoelectrical sensor changes in response to a particle shading the photoelectrical sensor. According to various embodiments, the at least one of the plurality of sensor elements may be an electrochemical fluid sensor configured to generate or modify an electrical signal in response to sensing a reference fluid.

According to various embodiments, each sensor element of the plurality of sensor elements may include or be formed from at least one sensor type of the following sensor types:

an electrical impedance sensor; a photoelectrical sensor; and/or an electrochemical fluid sensor.

According to various embodiments, the electrical impedance sensor may be configured to change its electrical impedance in response to a particle at least one of adsorbed to and approaching the electrical impedance sensor.

According to various embodiments, the electrical impedance sensor may include or be formed from two electrodes separated from each other and defining an electrical impedance of the electrical impedance sensor, wherein the two electrodes are configured to change the electrical impedance in response to a particle at least one of adsorbed to and approaching the electrical impedance sensor.

According to various embodiments, the electrical impedance may include or be formed from at least one of a resistive impedance (electrical resistance) and a capacitive impedance (capacitive reactance); wherein the electrical impedance sensor may be configured to change the resistive impedance in response to a particle physically contacting the two electrodes; and wherein the electrical impedance sensor may be configured to change the capacitive impedance in response to a particle disposed between the two electrodes.

According to various embodiments, the electrical impedance sensor may include a recess between the two electrodes for receiving a portion of a particle.

According to various embodiments, the electrical impedance sensor may include a further electrode disposed in the recess for providing a three-point contact.

According to various embodiments, the electrical impedance sensor may be configured to change the impedance in response to a particle having a particle size within a first particle size range defined by the electrical impedance sensor (e.g. in response to the particle physically contacting the two electrodes).

According to various embodiments, the first particle size range may be defined by at least one of: a distance of adjacent electrodes of the electrical impedance sensor; a topography of the electrical impedance sensor; and/or a depth of a recess between adjacent electrodes of the electrical impedance sensor.

According to various embodiments, the photoelectrical sensor may be configured to modify an electric charge movement capability in response to receiving electromagnetic radiation energy, such that an electrical output of the photoelectrical sensor changes in response to a particle shading the photoelectrical sensor.

According to various embodiments, the photoelectrical sensor may be configured to convert electromagnetic radiation energy into electrical energy, such that the electrical energy generated by the photoelectrical sensor changes in response to a particle shading the photoelectrical sensor.

According to various embodiments, the sensor arrangement may further include: an electromagnetic radiation source, configured to emit electromagnetic radiation to the photoelectrical sensor.

According to various embodiments, the electrochemical fluid sensor may be configured to generate or modify an electrical signal in response to sensing a reference fluid. According to various embodiments, the electrochemical fluid sensor may be configured to generate or modify an electrical signal in response to sensing a reference fluid, such that the electrical signal changes in response to a particle which may reduce the area of the electrochemical active region exposed to the reference fluid the electrochemical fluid sensor (e.g., a particle approaching (e.g. entering the near field of) the electrochemical fluid sensor may reduce the area of the electrochemical active region exposed to the reference fluid, thereby causing a change in the electric impedance of the electrochemical fluid sensor; in other words, the fraction of a sensing area of the electrochemical fluid sensor, which is exposed to the reference fluid, may be reduced due to the particle).

According to various embodiments, the electrochemical fluid sensor may be configured to sense at least one of a presence, a concentration, and a partial pressure of the reference fluid.

According to various embodiments, at least two sensor elements of the plurality of sensor elements differ in at least one of: a cross sectional area configured to sense particles; a sensor type; a number of electrodes; a particle size-sensing characteristic; a coverage by a filter layer; a permeability of a filter layer covering the two sensor elements, and/or a topography.

According to various embodiments, the sensor arrangement may further include a filter layer covering a section of the sensor array and configured to filter particle adsorption to the section of the sensor array by particle size.

According to various embodiments, the filter layer may include or be formed from a first filter region covering a first reference section of the sensor array, wherein the first filter region is fluid-permeable and non-particle-permeable.

According to various embodiments, the filter layer may include or be formed from a second filter region covering a second reference section of the sensor array and defining a second particle size range, wherein the second filter region is permeable (perforated region) for particles having a particle size within a second particle size range.

According to various embodiments, filter layer may be configured for filtering particles attracted to the section of the sensor array by at least one of particle size and particle shape.

According to various embodiments, the sensor arrangement may further include a cleaning device, configured for removing particles from the sensor array in a cleaning operation mode.

According to various embodiments, the cleaning device may include or be formed from at least one of: a cleaning fluid source; an electromechanical vibrator; a heat source; a repulsion electrode (e.g. the base electrode); a mechanical wiper; and/or a radiation source.

According to various embodiments, the cleaning device may further include a repulsion electrode controller unit.

According to various embodiments, the repulsion electrode controller unit may be configured to provide an electrical potential to the repulsion electrode for repulsing particles from the sensor array by electrostatic force.

According to various embodiments, the repulsion electrode controller unit may be configured to provide an alternating electrical potential to the repulsion electrode for at least one of repulsing and moving particles from the sensor array by electrical induced vibrations.

According to various embodiments, the cleaning fluid source may be configured to transfer at least one of a gaseous cleaning fluid and a liquid cleaning fluid to the sensor array for releasing a particle from the sensor array by purging.

According to various embodiments, the cleaning fluid source may include or be formed from a microfluidic pump.

According to various embodiments, the electromechanical vibrator may be configured transform electrical energy into mechanical vibration energy, wherein the electromechanical vibrator may be coupled to the sensor array for releasing a particle from the sensor array by mechanical vibration.

According to various embodiments, the sensor arrangement may further include: an actuator configured to actuate the mechanical wiper over the sensor array for releasing a particle from the sensor array by mechanical force.

According to various embodiments, the radiation source may be configured to expose the sensor array to radiation for releasing a particle from the sensor array by at least one of radiation induced weakening and radiation induced breaking of a chemical bonding between the particle and the sensor array.

According to various embodiments, the heat source may be configured to transfer thermal energy to the sensor array for releasing a particle from the sensor array by at least one of thermal weakening and thermal breaking of a chemical bonding between the particle and the sensor array.

According to various embodiments, the sensor arrangement may further include an anti-adhesion layer disposed over the sensor array for reducing an adhesion force of a particle to the sensor array.

According to various embodiments, the anti-adhesion layer may include or be formed from a first region and a second region differing in their adhesion strength to a particle.

According to various embodiments, the sensor arrangement may further include: a processing circuit electrically coupled to the sensor array via the contact structure and configured for processing at least one electrical signal generated or modified by the sensor array, wherein the processing circuit may be configured for identifying individual sensor elements of the plurality of sensor elements via the contact structure.

According to various embodiments, the processing circuit may be configured for determining a set of particle information by processing the at least one electrical signal.

According to various embodiments, the set of particle information may include or be formed from at least one of (e.g. a combination of at least two, e.g. tree, e.g. four) the following types of information: electrostatic charge information; particle size information; particle shape information; and/or particle material information.

According to various embodiments, the processing circuit may be configured for comparing the set of (determined) particle information with a plurality of predefined particle characteristics each representing a particle sort so as to determine the presence of at least one particle sort.

According to various embodiments, the processing circuit may be configured so as to determine the presence of at least one particle sort (e.g. for assigning the set of particle information to at least one particle sort) by comparing the set of particle information with a plurality of predefined particle characteristics each representing a particle sort.

According to various embodiments, the processing circuit may include an acquiring unit configured to acquire the at least one electrical signal generated or modified by a sensor element of the sensor array and provide signal data representing the at least one electrical signal.

According to various embodiments, at least one of the signal data and the set of particle information may include or be formed from at least one of temporal information (temporal information) and spatial information (spatial information) of the at least one electrical signal.

According to various embodiments, at least one of the signal data and the set of particle information may include or be formed from identification data representing a sensor element of the sensor array which generated or modified the at least one electrical signal.

According to various embodiments, the processing circuit may include or be formed from an identification unit configured to provide the identification data.

According to various embodiments, the sensor arrangement may further include a first memory storing a size-sensing characteristic for each sensor element of the plurality of sensor elements, wherein the processing circuit may be configured to determine particle information using the size-sensing characteristic stored in the first memory.

According to various embodiments, the size-sensing characteristic of each sensor element of the plurality of sensor elements may include or be formed from at least one of: at least one first particle size range defined by the sensor element, and a particle size range defined by a filter layer covering the sensor element.

According to various embodiments, the at least one first particle size range and the second particle range may overlap.

According to various embodiments, the processing circuit may include a base electrode controller unit coupled to the base electrode, wherein the base electrode controller unit may be configured to control an electrical potential provided to the base electrode in dependency to an operation mode.

According to various embodiments, the base electrode controller unit may be configured to provide a first electrical potential to the base electrode during a sensing operation mode for attracting particles to the sensor array.

According to various embodiments, the base electrode controller unit may be configured to provide a second electrical potential different to the first electrical potential to the base electrode in a cleaning operation mode for repulsing particles from the sensor array.

According to various embodiments, the processing circuit may be configured to determine electrostatic charge information by sensing at least one of a desorption event and an adsorption event (e.g. for an identified sensor) in dependency on a strength of the electrical potential provided to the base electrode.

According to various embodiments, the desorption event may represent an adhesion strength.

According to various embodiments, the adsorption event may represent an adhesion strength.

According to various embodiments, the processing circuit may be configured to determine at least one of particle size information, particle shape information and electrostatic charge information by correlating electrical signals generated or modified by adjacent sensor elements.

According to various embodiments, the processing circuit may be configured to determine particle material information by sensing at least one of: a change in the capacitive impedance of the sensor element (e.g. in response to a particle at least one of approaching and adsorbed to the sensor array); and a spectral characteristic of a particle (e.g. at least one of approaching and adsorbed to the sensor array).

According to various embodiments, the particle material information represent a dielectric characteristic (of a particle), e.g. a dielectric permittivity.

According to various embodiments, the particle material information represent an electrical conductivity characteristic (of a particle).

According to various embodiments, the particle material information represent an electrical resistivity characteristic (of a particle).

According to various embodiments, the processing circuit may be configured to determine particle material information by sensing a change in the resistive impedance of the sensor element in response to a particle at least one of approaching and adsorbed to the sensor array.

According to various embodiments, the processing circuit may be configured to determine a particle size information from at least one electrical signal generated or modified by a sensor element of the sensor array based on a size-sensing characteristic of the sensor element.

According to various embodiments, the processing circuit may be configured to determine particle shape information based on a change in resistive impedance of the sensor element in response to a particle at least one of approaching and adsorbed to the sensor array.

According to various embodiments, the particle shape information may represent a topography characteristic of a particle (e.g. spikes or tricolpate protrusions).

According to various embodiments, the processing circuit may be configured to assign the set of particle information to at least one particle sort by comparing the set of particle information with a plurality of predefined particle characteristics each representing a particle sort (illustratively, a fingerprint).

According to various embodiments, the tagging unit may be configured to assign a time stamp (also referred to as time tag) to the at least one electrical signal.

According to various embodiments, the processing circuit may be further configured to compare a time stamp of the at least one electrical signal to seasonal information so as to determine the presence of at least one particle sort (e.g. for assigning the set of particle information to at least one particle sort).

According to various embodiments, the tagging unit may be configured to assign a location stamp (also referred to as geotag) to the at least one electrical signal.

According to various embodiments, the processing circuit may be further configured to compare the location stamp to regional information so as to determine the presence of at least one particle sort (e.g. for assigning the set of particle information to at least one particle sort).

According to various embodiments, the processing circuit may include a second memory configured to store at least one of the plurality of predefined particle characteristics, the regional information, and the seasonal information.

According to various embodiments, the processing circuit may be configured to determine particle density information by sensing at least one of the desorption event and an adsorption event.

According to various embodiments, the processing circuit may be configured for array signal processing for correlating electrical signals generated or modified by more than one sensor element of the sensor array.

According to various embodiments, a method for particle analysis may include: acquiring at least one electrical signal generated or modified by a sensor array in response to a particle at least one of approaching and adsorbed to the sensor array; determining a set of particle information based on the plurality of electrical signals, wherein the set of particle information may include or be formed from at least one of (e.g. a combination of at least two, e.g. tree, e.g. four) the following types of information: electrostatic charge information; particle size information; particle shape information; and/or particle material information; and comparing the set of (determined) particle information with a plurality of predefined particle characteristics each representing a particle sort so as to determine the presence of at least one particle sort.

According to various embodiments, the method may further include assigning the set of particle information to at least one particle sort by comparing the set of particle information with a plurality of predefined particle characteristics each representing a particle sort.

According to various embodiments, the method may further include forming an electrical field for at least one of attracting particles to the sensor array and repulsing particles from the sensor array.

According to various embodiments, determining the electrostatic charge information may include or be formed from sensing of at least one of a desorption event and an adsorption event in dependency of a strength of the electrical potential.

According to various embodiments, the method may further include assigning an electrical signal of the plurality of electrical signals to a sensor element of the sensor array which generated or modified the electrical signal (e.g. by using identification data); wherein the determining the set of particle information may include or be formed from correlating a size-sensing characteristic of the sensor element with the electrical signal assigned thereto.

According to various embodiments, the size-sensing characteristic may include or be formed from on at least one of: a particle size range defined by the sensor element; a particle size range defined by a filter layer covering the sensor element.

According to various embodiments, the method may further include assigning at least two electrical signal of the plurality of electrical signals to adjacent sensor elements of the sensor array which generated or modified the at least two electrical signal (e.g. by using identification information); wherein the determining the set of particle information may include or be formed from correlating the at least two electrical signals with each other and with spatial information of the adjacent sensor elements assigned thereto.

According to various embodiments, at least one of particle size information, particle shape information and electrostatic charge information are determined by correlating the at least two electrical signals with each other.

According to various embodiments, correlating the at least two electrical signals with each other may include or be formed from using a size-sensing characteristic spatial of the adjacent sensor elements.

According to various embodiments, correlating the at least two electrical signals with each other may include or be formed from using temporal information of the two electrical signals.

According to various embodiments, the method may further include assigning an electrical signal of the plurality of electrical signals to one sensor element of the sensor array which generated or modified the electrical signal; wherein the determining a set of particle information may include or be formed from correlating the electrical signal with spatial information of the sensor element.

According to various embodiments, the method may further include forming a time stamp representing a time of the acquiring of the plurality of electrical signal.

According to various embodiments, assigning the set of particle information to at least one particle sort may include or be formed from comparing the time stamp to seasonal information of the particle sort.

According to various embodiments, the method may further include forming a location stamp representing a location of the acquiring of the plurality of electrical signal.

According to various embodiments, assigning the set of particle information to at least one particle sort may include or be formed from comparing the location stamp to regional information of the particle sort.

According to various embodiments, determining the particle material information may include or be formed from determining at least one of: a dielectric characteristic of the particle based on a change in capacitive impedance of the sensor array; and/or an electrical conductivity characteristic of the particle based on a change in a resistive impedance of the sensor array.

According to various embodiments, determining the particle size information may include or be formed from determining at least one of: an extension of the particle based on a distance of two electrodes; an extension of the particle based on a topography of the sensor element; a cross sectional area of the particle based on a cross sectional area of the sensor element configured to sense particles; a cross sectional area of the particle based on a correlating electrical signals of adjacent sensor elements; a cross sectional area of the particle based on a shading fraction of the sensor element; and/or an extension of the particle based on a depth of a recess of the sensor element.

According to various embodiments, determining the particle shape information may include or be formed from determining a curvature of the particle based on a topography of the sensor element;

According to various embodiments, determining the particle shape information may include or be formed from determining a contour of the particle based on a cross sectional area of the sensor element configured to sense particles.

According to various embodiments, determining the particle shape information may include or be formed from determining a contour of the particle based on a correlating electrical signals of adjacent sensor elements.

According to various embodiments, determining the particle shape information may include or be formed from determining a contour of the particle based on a shading of the sensor element.

According to various embodiments, determining the particle shape information may include or be formed from determining a curvature of the particle based on a depth of a recess of the sensor element.

According to various embodiments, determining the particle shape information may include or be formed from determining a topography characteristic of a particle based on a contact area with the sensor element.

According to various embodiments, the method may further include determining a particle density information based on a particle adhesion rate.

According to various embodiments, the method may further include removing particles from the sensor array in a cleaning operation mode.

According to various embodiments, the method may further include determining a reference characteristic of the sensor array after the removing particles; wherein determining the set of particle information based on the plurality of electrical signals may include or be formed from correlating the reference characteristic with the plurality of electrical signals for signal background subtraction.

According to various embodiments, the method may further include determining a set of particle information by comparing electrical signals generated or modified by a sensing section of the sensor array with electrical signals generated or modified by a reference section of the sensor array for signal background subtraction.

According to various embodiments, a sensor arrangement for particle analysis may include: a sensor array configured to generate or modify at least one electrical signal in response to a particle at least one of approaching and adsorbed to the sensor array; a processing circuit configured to sense the at least one electrical signal and determine a set of particle information based on the at least one electrical signal, wherein the set of particle information may include or be formed from at least one of (e.g. a combination of at least two, e.g. tree, e.g. four) the following types of information: electrostatic charge information; particle size information; particle shape information; and/or particle material information; and wherein the processing circuit may be configured for comparing the set of (determined) particle information with a plurality of predefined particle characteristics each representing a particle sort so as to determine the presence of at least one particle sort.

According to various embodiments, the processing circuit may be configured to assign the set of particle information to at least one particle sort by comparing the set of particle information with a plurality of predefined particle characteristics each representing a particle sort.

According to various embodiments, the sensor arrangement may further include a base electrode; a base electrode controller unit configured to provide an electrical potential to the base electrode for forming an electrical field for at least one of attracting of repulsing particles to the sensor array.

According to various embodiments, the processing circuit may be configured to sense at least one of a desorption event and an adsorption event in dependency of a strength of the electrical potential for determining the electrostatic charge information.

According to various embodiments, the processing circuit may be configured to assign an electrical signal of the plurality of electrical signals to a sensor element of the sensor array which generated or modified the electrical signal (e.g. by using identification data).

According to various embodiments, the processing circuit may be configured to correlate a size-sensing characteristic of the sensor element with the electrical signal assigned thereto for determining the set of particle information.

According to various embodiments, the size-sensing characteristic may include or be formed from on at least one of: a particle size range defined by the sensor element; a maximum particle size defined by a particle filter covering the sensor element.

According to various embodiments, the processing circuit may be configured to assign at least two electrical signal of the plurality of electrical signals to adjacent sensor elements of the sensor array which generated or modified the at least two electrical signal (e.g. by using identification information).

According to various embodiments, the processing circuit may be configured to correlate the at least two electrical signals with each other for determining the set of particle information.

According to various embodiments, the processing circuit may be configured to correlate the at least two electrical signals with each other for determining at least one of particle size information, particle shape information and adhesion strength information.

According to various embodiments, the processing circuit may be configured to use spatial information of the adjacent sensor elements for correlating the at least two electrical signals with each other.

According to various embodiments, the processing circuit may be configured to use temporal information of the acquiring of the two electrical signals for correlating the at least two electrical signals with each other.

According to various embodiments, the processing circuit may be configured to assign an electrical signal of the plurality of electrical signals to one sensor element of the sensor array which generated or modified the electrical signal; wherein the processing circuit may be configured to correlate the electrical signal with spatial information of the sensor element for determining a set of particle information.

According to various embodiments, the processing circuit may be configured to form a time stamp representing a time of the acquiring of the plurality of electrical signal.

According to various embodiments, the processing circuit may be configured to compare the time stamp to seasonal information of the particle sort so as to determine the presence of at least one particle sort (e.g. for assigning the set of particle information to at least one particle sort).

According to various embodiments, the processing circuit may be configured to form a location of the acquiring of the plurality of electrical signal.

According to various embodiments, the processing circuit may be configured to compare the location stamp to regional information of the particle sort so as to determine the presence of at least one particle sort (e.g. for assigning the set of particle information to at least one particle sort).

According to various embodiments, the processing circuit may be configured to determine at least one of the following particle material information: a dielectric characteristic of the particle based on a change in capacitive impedance of the sensor array; and/or an electrical conductivity characteristic of the particle based on a change in a resistive impedance of the sensor array.

According to various embodiments, the processing circuit may be configured to determine at least one of the following particle size information: an extension of the particle based on a distance of two electrodes; an extension of the particle based on a topography of the sensor element; a cross sectional area of the particle based on a cross sectional area of the sensor element configured to sense particles; a cross sectional area of the particle based on a correlating electrical signals of adjacent sensor elements; a cross sectional area of the particle based on a shading fraction of the sensor element; and/or an extension of the particle based on a depth of a recess of the sensor element.

According to various embodiments, the processing circuit may be configured to determine at least one of the following particle shape information: a curvature of the particle based on a topography of the sensor element; a contour of the particle based on a cross sectional area of the sensor element configured to sense particles; a contour of the particle based on a correlating electrical signals of adjacent sensor elements; a contour of the particle based on a shading of the sensor element and/or a curvature of the particle based on a depth of a recess of the sensor element; a topography characteristic of a particle based on a contact area with the sensor element.

According to various embodiments, the processing circuit may be configured to determine a particle density information based on a particle adhesion rate.

According to various embodiments, the sensor arrangement may further include a cleaning device, configured for removing particles from the sensor array in a cleaning operation mode.

According to various embodiments, the processing circuit may be configured to determine a reference characteristic of the sensor array in a reference operation mode after the cleaning operation mode According to various embodiments, the processing circuit may be configured to correlate the reference characteristic with the plurality of electrical signals for signal background subtraction for determining the set of particle information in a sensing operation mode after the reference operation mode.

According to various embodiments, the processing circuit may be configured to compare electrical signals generated or modified by a sensing section of the sensor array with electrical signals generated or modified by a reference section of the sensor array for signal background subtraction.

According to various embodiments, a particle size may be less than 100 µm, e.g. less than 50 µm, e.g. less than 10 µm, e.g. less than 1 µm.

According to various embodiments, the at least one of the method and the sensor arrangement may be used for determining properties of an aerosol. The aerosol may include or be formed from a fluid (e.g. the reference fluid) and particles (the particles to detect).

According to various embodiments, a particle may be understood as made from a solid material, such as for example, organic material, polymers, and combustion residues. The particle may be airborne. The particle may include an inherent charge, e.g. in case of pollen.

According to various embodiments, a mobile device may include a sensor arrangement according to various embodiments.

According to various embodiments, the mobile device may include or be formed from a handheld computer or a tablet computer.

According to various embodiments, the mobile device may further include a transceiver and a transceiver circuit configured to provide a physical access to radio resources in accordance with at least one of a cellular wide area radio communication technology and a short range radio communication technology.

According to various embodiments, the mobile device may further include an application processor, configured to support one or more applications running in a mobile operating system environment.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes, which come within the meaning and range of equivalency of the claims are therefore intended to be embraced.

What is claimed is:

1. A sensor arrangement for particle analysis, comprising:
 a base electrode configured to generate an electrical field for solid particle attraction;
 a support layer disposed over the base electrode;
 a sensor array disposed over the support layer and comprising a plurality of sensor elements, wherein each sensor element of the plurality of sensor elements is configured to generate or modify an electrical signal in response to a solid particle at least one of adsorbed to and approaching the sensor element; and
 an electrical contact structure comprising a plurality of contact lines, wherein each contact line of the plurality of contact lines is electrically connected to a respective sensor element of the plurality of sensor elements, such that each sensor element of the plurality of sensor elements is addressable via the contact structure.

2. The sensor arrangement of claim 1,
wherein each sensor element of the plurality of sensor elements comprises at least one sensor type of the following sensor types:
an electrical impedance sensor;
a photoelectrical sensor; and/or
an electrochemical fluid sensor.

3. The sensor arrangement of claim 2,
wherein the electrical impedance sensor is configured to change its electrical impedance in response to a solid particle at least one of adsorbed to and approaching the electrical impedance sensor.

4. The sensor arrangement of claim 2,
wherein the photoelectrical sensor is configured to modify an electric charge movement capability in response to receiving electromagnetic radiation energy, such that an electrical output of the photoelectrical sensor changes in response to a solid particle shading the photoelectrical sensor.

5. The sensor arrangement of claim 2, further comprising:
an electromagnetic radiation source, configured to emit electromagnetic radiation to the photoelectrical sensor.

6. The sensor arrangement of claim 2,
wherein the electrochemical fluid sensor is configured to generate or modify an electrical signal in response to sensing a reference fluid.

7. The sensor arrangement of claim 1, further comprising:
a filter layer covering a section of the sensor array and configured to filter solid particle adsorption to the section of the sensor array by at least one of particle size and particle shape.

8. The sensor arrangement of claim 7,
wherein the filter layer comprises a first filter region covering a first reference section of the sensor array, wherein the first filter region is fluid-permeable and non-particle-permeable.

9. The sensor arrangement of claim 7,
wherein the filter layer comprises a second filter region covering a second reference section of the sensor array and defining a solid particle size range,
wherein the second filter region is permeable for solid particles having a particle size within the particle size range.

10. The sensor arrangement of claim 1, further comprising:
a cleaning device, configured for removing solid particles from the sensor array in a cleaning operation mode.

11. The sensor arrangement of claim 10,
wherein the cleaning device comprises at least one of:
a cleaning fluid source;
an electromechanical vibrator;
a heat source;
a repulsion electrode;
a mechanical wiper; and/or
a radiation source.

12. The sensor arrangement of claim 1, further comprising:
an anti-adhesion layer disposed over the sensor array for reducing an adhesion force of a solid particle to the sensor array.

13. The sensor arrangement of claim 12,
wherein the anti-adhesion layer comprises a first region and a second region differing in their adhesion strength to a solid particle.

14. The sensor arrangement of claim 1, further comprising:
a processing circuit electrically coupled to the sensor array via the contact structure and configured for processing at least one electrical signal generated or modified by the sensor array, wherein the processing circuit is configured for identifying individual sensor elements of the plurality of sensor elements via the contact structure.

15. The sensor arrangement of claim 14,
wherein the processing circuit is configured for determining a set of particle information by processing the at least one electrical signal.

16. The sensor arrangement of claim 15,
wherein the set of particle information comprises at least one of the following types of information:
electrostatic charge information;
particle size information;
particle shape information; and/or
particle material information.

17. The sensor arrangement of claim 14,
wherein the processing circuit is configured to determine electrostatic charge information by sensing at least one of a desorption event and an adsorption event in dependency on a strength of an electrical potential provided to the base electrode.

18. The sensor arrangement of claim 14,
wherein the processing circuit is configured to determine particle material information by sensing at least one of:
a change in the capacitive impedance of the sensor element; and
a spectral characteristic of a particle.

19. The sensor arrangement of claim 14,
wherein the processing circuit comprises a tagging unit configured to assign a time stamp to the at least one electrical signal, and
wherein the processing circuit is further configured to compare the time stamp of the at least one electrical signal to a seasonal information so as to determine the presence of at least one particle sort.

20. The sensor arrangement of claim 14,
wherein the processing circuit comprises a tagging unit configured to assign a location stamp to the at least one electrical signal, and
wherein the processing circuit is further configured to compare the location stamp to a regional information so as to determine the presence of at least one particle sort.

21. A method for particle analysis, comprising:
acquiring at least one electrical signal generated or modified by a sensor array in response to a solid particle at least one of approaching and adsorbed to the sensor array;
determining a set of particle information based on the plurality of electrical signals, wherein the set of particle information comprises at least one of the following types of information:
electrostatic charge information;
particle size information;
particle shape information; and/or
particle material information; and
comparing the set of particle information with a plurality of predefined particle characteristics each representing a particle sort so as to determine the presence of at least one particle sort.

22. A sensor arrangement for particle analysis, comprising:
- a sensor array configured to generate or modify at least one electrical signal in response to a solid particle at least one of approaching and adsorbed to the sensor array;
- a processing circuit configured to sense the at least one electrical signal and determine a set of particle information based on the at least one electrical signal, wherein the set of particle information comprises at least one of the following types of information:
- electrostatic charge information;
- particle size information;
- particle shape information; and/or
- particle material information; and
- wherein the processing circuit is configured for comparing the set of particle information with a plurality of predefined particle characteristics each representing a particle sort so as to determine the presence of at least one particle sort.

* * * * *